United States Patent
Bottomley et al.

(10) Patent No.: US 10,392,424 B2
(45) Date of Patent: Aug. 27, 2019

(54) MODIFIED MENINGOCOCCAL FHBP POLYPEPTIDES

(71) Applicant: GLAXOSMITHKLINE BIOLOGICALS SA, Rixensart (BE)

(72) Inventors: Matthew Bottomley, Siena (IT); Enrico Malito, Siena (IT); Manuele Martinelli, Siena (IT); Maria Scarselli, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/120,674

(22) PCT Filed: Feb. 27, 2015

(86) PCT No.: PCT/EP2015/054174
§ 371 (c)(1),
(2) Date: Aug. 22, 2016

(87) PCT Pub. No.: WO2015/128480
PCT Pub. Date: Sep. 3, 2015

(65) Prior Publication Data
US 2017/0008933 A1 Jan. 12, 2017

(30) Foreign Application Priority Data

Feb. 28, 2014 (EP) .................................. 14157399
Jul. 17, 2014 (EP) .................................. 14177566

(51) Int. Cl.
*A61K 39/095* (2006.01)
*C07K 14/22* (2006.01)
*A61K 39/00* (2006.01)

(52) U.S. Cl.
CPC ............ *C07K 14/22* (2013.01); *A61K 39/095* (2013.01); *A61K 2039/523* (2013.01); *A61K 2039/55511* (2013.01); *A61K 2039/70* (2013.01)

(58) Field of Classification Search
None
See application file for complete search history.

(56) References Cited

FOREIGN PATENT DOCUMENTS

| WO | WO 2004/048404 | 6/2004 |
|---|---|---|
| WO | WO 2007/060548 | 5/2007 |
| WO | WO 2008/079372 | 7/2008 |
| WO | WO 2011/126863 | 10/2011 |
| WO | WO 2014/030003 | 2/2014 |

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252.*
Bork (Genome Research, 2000,10: 398-400).*
Greenspan et al. (Nature Biotechnology 17: 936-937, 1999).*
Murphy, E. sequence entitled "Factor H binding protein variant A93_001" published as UniProtKB Accession No. G9I6U8, dated Feb. 22, 2012, available at http://www.uniprot.org/uniprot/G9I6U8.txt?version=1.
Zlotnick, G. W.; sequence described as "Neisseria ORF2086 subfamily A protein" corresponding to SEQ ID No. 6 of international patent application publication WO2008079372; sequence published as Geneseq Accession No. ASQ06840, dated Sep. 4, 2008.
Pajon et al., *Design of Meningococcal Factor H Binding Protein Mutant Vaccines That Do Not Bind Human Complement Factor H*, 2012 Inf. & Imm. 80(8):2667-2677.
Johnson et al., *Design and Evaluation of Meningococcal Vaccines through Structure-Based Modification of Host and Pathogen Molecules*, 2012 PLOS Path. 8(10): e1002981, 13 total pages.
Romanelli, et al. sequence entitled "Factor H binding protein" published as UniProtKB Accession No. L0GGE0, dated Mar. 6, 2013, available at http://www.uniprot.org/uniprot/L0GGE0.txt?version=1.
Lucidarme, J. sequence entitled "Factor H-binding protein" published as UniProtKB Accession No. D3JZH2, dated Mar. 23, 2010, available at http://www.uniprot.org/uniprot/D3JZH2.txt?version=1.
Lucidarme, J. sequence entitled "Factor H-binding protein" published as UniProtKB Accession No. D3JZI3, dated Mar. 23, 2010, available at http://www.uniprot.org/uniprot/D3JZI3.txt?version=1.
Romanelli, et al. sequence entitled "Factor H binding protein" published as UniProtKB Accession No. L0GFA3, dated Mar. 6, 2013, available at http://www.uniprot.org/uniprot/L0GFA3.txt?version=1.
Schneider, MC, et al., *Neisseria meningitidis recruits factor H using protein mimicry of host carbohydrates*, 2009 Nature 458(7240): 890-893.
Beernink et al., *Impaired immunogenicity of a meningococcal factor H-binding protein vaccine engineered to eliminate factor h binding*, 2010 Clin. Vaccine Immunol. 17(7):1074-1078.
Granoff, et al., *Does binding of complement factor H to the meningococcal vaccine antigen, factor H binding protein, decrease protective serum antibody responses?*, 2013 Clin. Vaccine Immunol. 20(8):1099-1107.
Beernink, et al., *A meningococcal factor H binding protein mutant that eliminates factor H binding enhances protective antibody responses to vaccination*, 2011 J. Immunol. 186(6):3606-3614.
Rossi, et al., *Meningococcal factor H-binding protein vaccines with decreased binding to human complement factor H have enhanced immunogenicity in human factor H transgenic mice.*, 2013 Vaccine 31(46):5451-5457.
Van Der Veen et al., *Nonfunctional Variant 3 Factor H Binding Proteins as Meningococcal Vaccine Candidates*, 2014 Infect. Immun. 82(3):1157-1163.
European Patent Office, office action received for corresponding EP Appl. No. 15 707 351.1 (published as EP3110442), dated Aug. 8, 2017, 5 total pages.
European Patent Office, priority search results and written opinion received for corresponding EP Appl. No. 14 15 7399, dated Sep. 28, 2016, 24 total pages.

(Continued)

*Primary Examiner* — Jennifer E Graser

(57) ABSTRACT

Modified meningococcal fHbp polypeptides with increased stability.

12 Claims, 5 Drawing Sheets

Specification includes a Sequence Listing.

(56) References Cited

OTHER PUBLICATIONS

European Patent Office as International Searching Authority, International Search Report and Written Opinion for International Appl. No. PCT/EP2015/054174 (published as WO 2015128480), dated Sep. 3, 2015, 11 total pages.
Johnson et al., *Design and Evaluation of Meningococcal Vaccines through Structure-based Modification of Host and Pathogen Molecules*, 2012 PLOS Pathogens 8(10): e1002981 (Table S4 included, 15 total pages).
Beernink et al., *Rapid Genetic Grouping of Factor H-Binding Protein (Genome-Derived Neisserial Antigen 1870), a Promising Group B Meningococcal Vaccine Candidate*, 2006 Clin. & Vaccine Immunol. 13(7): 758-763.
Brehony et al., *Variation of the factor H-binding protein of Neisseria meningitidis*, 2009 Microbiology 155:4155-4169 at p. 4161.
Beernink & Granoff, *The modular architecture of meningococcal factor H-binding protein*, 2009 Microbiology 155:2873-2883.

\* cited by examiner

MODIFIED MENINGOCOCCAL FHBP POLYPEPTIDES

This application is filed pursuant to 35 U.S.C. § 371 as a United States National Phase Application of International Patent Application Serial No. PCT/EP2015/054174 filed Feb. 27, 2015, which claims priority to European Application No. 14157399.8 filed Feb. 28, 2014, and to European Application No. 14177566.8 filed Jul. 17, 2014, and the entire contents of each of the foregoing applications are hereby incorporated by reference.

TECHNICAL FIELD

This invention is in the field of protein engineering, relating in particular to the meningococcal factor H binding protein (fHbp), which is known to be a useful vaccine immunogen.

BACKGROUND ART

*Neisseria meningitidis* is a Gram-negative encapsulated bacterium which colonises the upper respiratory tract of approximately 10% of human population. Conjugate vaccines are available against serogroups A, C, W135 and Y, but the only vaccine which is available for protecting against serogroup B in a two-dose regimen is the BEXSERO™ product which was approved in 2013.

One of the protective immunogens in BEXSERO™ is fHbp, which has also been known as protein '741' (SEQ ID NO: 2536 in ref. 1; SEQ ID 1 herein), 'NMB1870', 'GNA1870' [2-4, 'P2086', 'LP2086' or 'ORF2086' [5-7]. The 3D structure of this protein is known [8,9], and the protein has two β-barrels connected by a short linker. Many publications have reported on the protective efficacy of this protein in meningococcal vaccines e.g. see references 10-14. The fHbp lipoprotein is expressed in various strains across all serogroups. fHbp sequences have been grouped into three variants [2] (referred to herein as v1, v2 and v3), and it has been found in general that serum raised against a given variant is bactericidal against strains which express that variant, but is not active against strains which express one of the other two variants i.e. there is intra-variant cross-protection, but not inter-variant cross-protection (except for some v2 and v3 cross-reactivity).

To increase inter-family cross-reactivity the fHbp sequence has been engineered to contain specificities for all three variants [15]. Protein engineering has also been used to remove fHbp's interaction with siderophores [16] and with factor H [17-25]. Disruption of the interaction with fH has been reported for all three variants and is postulated to provide a superior vaccine immunogen [22,26]. For v2 polypeptides, however, references 23 and 24 report an inherent instability which is also seen in mutants with disrupted fH-binding. The instability appears to arise from the N-terminal β-barrel domain, and reference 23 warns that any substitutions in this barrel might promote instability.

It is an object of the invention to provide further fHbp v2 and v3 mutants, but having enhanced stability.

DISCLOSURE OF THE INVENTION

Full-length fHbp from strain 2996 in v2 has the following amino acid sequence (SEQ ID NO: 2):

```
MNRTAFCCLSLTAALILTACSSGGGGVAADIGAGLADALTAPLDHKDKSL
QSLILDQSVRKNEKLKLAAQGAEKTYGNGDSLNIGKLKNDKVSREDFIRQ
```

-continued

```
IEVDGQLITLESGEFQIYKQDHSAVVALQIEKINNPDKIDSLINQRSELV
SGLGGEHTAFNQLPDGKAEYHGKAFSSDDAGGKLTYTIDFAAKQGHGKIE
HLKTPEQNVELAAAELKADEKSHAVILGDTRYGSEEKGTYHLALFGDRAQ
EIAGSATVKIGEKVHEIGIAGKQ
```

The mature lipoprotein lacks the first 19 amino acids of SEQ ID NO: 2 (underlined; provides SEQ ID NO: 4), and the ΔG form of SEQ ID NO: 2 lacks the first 26 amino acids (SEQ ID NO: 5).

Full-length fHbp from strain M1239 in v3 has the following amino acid sequence (SEQ ID NO: 3):

```
MNRTAFCCLSLTTALILTACSSGGGGSGGGGVAADIGTGLADALTAPLDH
KDKGLKSLTLEDSIPQNGTLTLSAQGAEKTFKAGDKDNSLNTGKLKNDKI
SREDEVQKIEVDGQTITLASGEFQIYKQNHSAVVALQIEKINNPDKTDSL
INQRSFLVSGLGGEHTAFNQLPGGKAEYHGKAFSSDDPNGRLHYSIDFTK
KQGYGRIEHLKTLEQNVELAAAELKADEKSHAVILGDTRYGSEEKGTYHL
ALFGDRAQEIAGSATVKIGEKVHEIGIAGKQ
```

The mature lipoprotein lacks the first 19 amino acids of SEQ ID NO: 3 (underlined; provides SEQ ID NO: 40), and the ΔG form of SEQ ID NO: 3 lacks the first 31 amino acids (SEQ ID NO: 17).

The inventors have identified residues within SEQ ID NO: 2 and SEQ ID NO: 3 which can be modified to increase the polypeptide's stability. These residues are generally present across v2 and v3 sequences and so their modification can provide v2 and v3 fHbp sequences with enhanced stability. Moreover, the inventors have shown that, as well as increasing stability, mutation of these residues can advantageously decrease binding to human factor H (fH). In addition, however, the mutations disclosed herein can be combined with other mutations e.g. to decrease binding to human factor H (fH), for which several mutations are already known in the art.

Thus, in general the invention provides a mutant v2 or v3 fHbp which has increased stability relative to a wild-type fHbp (e.g. relative to SEQ ID NOs: 2 or 3) and which, optionally, has lower affinity for human factor H than a wild-type fHbp (e.g. relative to SEQ ID NOs: 2 or 3). The increase in stability and the optional reduction in fH affinity preferably result from the same mutation(s), but in some embodiments they may be due to the separate effect of combined mutations. Mutant fHbp proteins with both increased stability and reduced fH affinity are preferred.

In a first embodiment the invention provides a polypeptide comprising a mutant fHbp v2 amino acid sequence, wherein: (a) the amino acid sequence has at least k % sequence identity to SEQ ID NO: 5, and/or comprises a fragment of SEQ ID NO: 5; but (b) the amino acid sequence differs from SEQ ID NO: 5 at one or more of the following residues: S32, V33, L39, L41, F69, V100, I113, F122, L123, V124, S125, G126, L127, G128, S151, H239, and/or E240.

Where feature (a) relates to a fragment, the fragment will include at least one of the residues listed in (b), but that residue will differ when compared to that residue in SEQ ID NO: 5. A fragment of (a) will generally be at least 7 amino acids long e.g. 8, 10, 12, 14, 16, 18, 20, 22, 24, 26, 28, 30, 32, 24, 26, 28, 40, 45, 50, 55, 60 contiguous amino acids or more from SEQ ID NO: 5. The fragment will typically include at least one epitope from SEQ ID NO: 5. Epitope identification and mapping is established for fHbp [11; 27-31]. Sharing at least 30 contiguous amino acids with SEQ ID NO: 5 will be typical, and usually a mutant fHbp v2 amino acid sequence will include several (e.g. 2, 3, 4, 5 or more) fragments from SEQ ID NO: 5. Overall, a mutant fHbp v2 amino acid sequence can have at least k % sequence identity to and include several fragments of SEQ ID NO: 5.

The value of k may be selected from 80, 85, 86, 87, 88, 89, 90, 91, 92, 93, 94, 95, 96, 97, 98, 99 or more. It is preferably 90 (i.e. the mutant fHbp v2 amino acid sequence has at least 90% identity to SEQ ID NO: 5) and is more preferably 95.

The polypeptide can, after administration to a host animal, elicit antibodies which can recognise a wild-type meningococcal polypeptide consisting of SEQ ID NO: 4. These antibodies are ideally bactericidal (see below). These antibodies can include some antibodies which do not recognise a v1 or a v3 polypeptide (e.g. a wild-type meningococcal polypeptide consisting of SEQ ID NO: 46 and a wild-type meningococcal polypeptide consisting of SEQ ID NO: 40), although they may also include some antibodies which cross-react with v1 and/or v3 polypeptides.

The polypeptide has, under the same experimental conditions, a higher stability than the same polypeptide but without the sequence difference/s of (b) e.g. higher stability than a wild-type meningococcal polypeptide consisting of SEQ ID NO: 4. The stability enhancement can be assessed using differential scanning calorimetry (DSC) e.g. as discussed in references 32 & 33. DSC has previously been used to assess the stability of v2 fHbp [24]. Suitable conditions for DSC to assess stability can use 20 µM of polypeptide in a buffered solution (e.g. 25 mM Tris) with a pH between 6 and 8 (e.g. 7-7.5) with 100-200 mM NaCl (e.g. 150 mM).

In some embodiments, the polypeptide of the invention is truncated relative to SEQ ID NO: 5. Compared to the wild-type mature sequence, SEQ ID NO: 5 is already truncated at the N-terminus up to and including the polyglycine sequence (compare SEQ ID NOs: 4 and 5), but SEQ ID NO: 5 can be truncated at the C-terminus and/or further truncated at the N-terminus.

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur even below 40° C. with wild-type v2 sequences [24] (whereas C-terminal domains can have a Tm of 80° C. or more). Thus the mutant fHbp v2 amino acid sequence of the invention preferably has a N-terminal domain with a Tm of at least 45° C. e.g. ≥50° C., ≥55° C., ≥60° C., ≥65° C., ≥70° C., ≥75° C., or even ≥80° C.

In a second embodiment, the invention provides a polypeptide comprising a mutant fHbp v3 amino acid sequence, wherein: (a) the amino acid sequence has at least j % sequence identity to SEQ ID NO: 17, and/or comprises a fragment of SEQ ID NO: 17; but (b) the amino acid sequence differs from SEQ ID NO: 17 at one or more of the following residues: S32, I33, L39, L41, F72, V103, T116, F125, L126, V127, S128, G129, L130, G131, S154, H242, and/or E243.

Where feature (a) relates to a fragment, the fragment will include at least one of the residues listed in (b), but that residue will differ when compared to that residue in SEQ ID NO: 17. A fragment of (a) will generally be at least 7 amino acids long e.g. 8, 10, 12, 14, 16, 18, 20, 22, 24, 26, 28, 30, 32, 24, 26, 28, 40, 45, 50, 55, 60 contiguous amino acids or more from SEQ ID NO: 17. The fragment will typically include at least one epitope from SEQ ID NO: 17. Epitope identification and mapping is established for fHbp [11; 27-31]. Sharing at least 30 contiguous amino acids with SEQ ID NO: 17 will be typical, and usually a mutant fHbp v3 amino acid sequence will include several (e.g. 2, 3, 4, 5 or more) fragments from SEQ ID NO: 17. Overall, a mutant fHbp v3 amino acid sequence can have at least j % sequence identity to and include several fragments of SEQ ID NO: 17.

The value of j may be selected from 80, 85, 86, 87, 88, 89, 90, 91, 92, 93, 94, 95, 96, 97, 98, 99 or more. It is preferably 90 (i.e. the mutant fHbp v3 amino acid sequence has at least 90% identity to SEQ ID NO: 17) and is more preferably 95.

The polypeptide can, after administration to a host animal, elicit antibodies which can recognise a wild-type meningococcal polypeptide consisting of SEQ ID NO: 40. These antibodies are ideally bactericidal (see below). These antibodies can include some antibodies which do not recognise a v1 or a v2 polypeptide (e.g. a wild-type meningococcal polypeptide consisting of SEQ ID NO: 46 and a wild-type meningococcal polypeptide consisting of SEQ ID NO: 4), although they may also include some antibodies which cross-react with v1 and/or v2 polypeptides.

The polypeptide has, under the same experimental conditions, a higher stability than the same polypeptide but without the sequence difference/s of (b) e.g. higher stability than a wild-type meningococcal polypeptide consisting of SEQ ID NO: 40. The stability enhancement can be assessed using differential scanning calorimetry (DSC) e.g. as discussed in references 32 & 33 DSC has previously been used to assess the stability of v3 fHbp [23]. Suitable conditions for DSC to assess stability can use 20 µM of polypeptide in a buffered solution (e.g. 25 mM Tris) with a pH between 6 and 8 (e.g. 7-7.5) with 100-200 mM NaCl (e.g. 150 mM).

In some embodiments, the polypeptide of the invention is truncated relative to SEQ ID NO: 17. Compared to the wild-type mature sequence, SEQ ID NO: 17 is already truncated at the N-terminus up to and including the polyglycine sequence (compare SEQ ID NOs: 40 and 17), but SEQ ID NO: 17 can be truncated at the C-terminus and/or further truncated at the N-terminus.

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur at around 60° C. or less with wild-type v3 sequences [24] (whereas C-terminal domains can have a Tm of 80° C. or more). Thus the mutant fHbp v3 amino acid sequence of the invention preferably has a N-terminal domain with a Tm of at least 65° C. e.g. ≥70° C., ≥75° C., or even ≥80° C.

Mutations Relative to SEQ ID NO: 5

Polypeptides of the first embodiment of the invention comprise an amino acid sequence which has at least k % identity to SEQ ID NO: 5, and/or comprise a fragment of SEQ ID NO: 5. In comparison to SEQ ID NO: 5, however, this amino sequence has a modification at one or more of amino acid residues S32, V33, L39, L41, F69, V100, I113, F122, L123, V124, S125, G126, L127, G128, S151, H239, and/or E240 e.g. at 2, 3, 4, 5 or more of these 17 residues. These residues are numbered according to SEQ ID NO: 5; to match the nascent wild-type sequence (SEQ ID NO: 2), the numbering should change +26 (i.e. Ser-32 of SEQ ID NO: 5 is Ser-58 of SEQ ID NO: 2), and to match the mature wild-type sequence (SEQ ID NO: 4) the numbering should change +7 (which also permits easy comparison with ref. 25).

Preferred residues for mutation are S32, V100, L123, V124, S125, G126, L127, G128, H239, and/or E240. Mutations at these residues give proteins having good stability compared to wild-type v2. Within this subset, preferred residues are S32, L123, V124, S125, G126, L127, and/or G128. The most preferred positions are S32, L123, V124, S125, G126, L127, and/or G128, with residues S32 and/or L123 being particularly preferred e.g. S32V and/or L123R. Where one or more of V100, S125, and/or G126 is mutated, it is preferred to mutate also a residue outside this trio.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative. In some embodiments the substitution does not use alanine.

Preferred substitutions at the specified residues are as follows: S32V; V33C; L39C; L41C; F69C; V100T; I113S; F122C; L123R; V124I; S125G or S125T; G126D; L127I; G128A; S151C; H239R; E240H.

Where the mutant fHbp v2 amino acid sequence includes a substitution at E240, this substitution will not be with alanine if only E240 is mutated, although it can be alanine if a further amino acid listed in (b) is substituted e.g. if residues E240 and H239 are both mutated. Ideally, E240 is not mutated on its own, and so a mutant fHbp v2 amino acid sequence with a substitution at E240 should also include a substitution at a second residue e.g. at both E240 and H239 (see mutants #1 and #11).

Where the mutant fHbp v2 amino acid sequence includes a substitution at F122, this substitution will not be with alanine if only F122 is mutated, although it can be alanine if a further amino acid listed in (b) is substituted e.g. if residues F122 and S151 are both mutated. Ideally, F122 is not mutated on its own, and so a mutant fHbp v2 amino acid sequence with a substitution at F122 should also include a substitution at a second residue. When F122 is substituted it is preferred that S151 is also substituted e.g. both are substituted with cysteine, to permit formation of a disulfide bridge (see mutant #10).

Where the mutant fHbp v2 amino acid sequence includes a substitution at L123, this substitution will not be with alanine if only L123 is mutated, although it can be alanine if a further amino acid listed in (b) is substituted e.g. if residues L123 and S32 are both mutated. If L123 is mutated on its own, substitution with arginine is preferred (e.g. see mutant #4). In some embodiments, however, L123 is not mutated on its own, and so a mutant fHbp v2 amino acid sequence with a substitution at L123 can also include a substitution at a second residue. When L123 is substituted it can be preferred that: (i) S32 is also substituted, as seen in mutant #3, and optionally S125 is also substituted, as seen in mutants #20 and #22; or (ii) one or more of residues 124-128 is/are also substituted e.g. as seen in mutant #12.

Where the mutant fHbp v2 amino acid sequence includes a substitution at V124, it is preferred that this substitution will not be with alanine if only V124 is mutated, although it can be alanine if a further amino acid listed in (b) is substituted e.g. if one or more of residues 123-128 are also mutated. If V124 is mutated on its own, substitution with isoleucine is preferred. Ideally, however, V124 is not mutated on its own, and so a mutant fHbp v2 amino acid sequence with a substitution at V124 should also include a substitution at a second residue. When V124 is substituted it is preferred that one or more of residues 124-128 is/are also substituted e.g. as seen in mutant #12.

Where the mutant fHbp v2 amino acid sequence includes a substitution at L127, it is preferred that this substitution will not be with alanine if only L127 is mutated, although it can be alanine if a further amino acid listed in (b) is substituted e.g. if one or more of residues 123-128 are also mutated. If L127 is mutated on its own, substitution with isoleucine is preferred. Ideally, however, L127 is not mutated on its own, and so a mutant fHbp v2 amino acid sequence with a substitution at L127 should also include a substitution at a second residue. When L127 is substituted it is preferred that one or more of residues 124-128 is/are also substituted e.g. as seen in mutant #12.

Where the mutant fHbp v2 amino acid sequence includes a substitution at S32, it is preferred that this substitution will not be with alanine if only S32 is mutated, although it can be alanine if a further amino acid listed in (b) is substituted e.g. if residues L123 and S32 are both mutated. If S32 is mutated on its own, substitution with valine is preferred. Ideally, however, S32 is not mutated on its own, and so a mutant fHbp v2 amino acid sequence with a substitution at S32 should also include a substitution at a second residue. When S32 is substituted it is preferred that (i) L123 is also substituted e.g. as seen in mutant #3, and optionally S125 is also substituted, as seen in mutants #20 and #22; or (ii) S125 is also substituted e.g. as seen in mutants #19 and #21.

Where the mutant fHbp v2 amino acid sequence includes a substitution at I113, this substitution will not be with alanine if only I113 is mutated, although it can be alanine if a further amino acid listed in (b) is substituted. If I113 is mutated on its own, substitution with serine is preferred e.g. as seen in mutant #7.

Where the mutant fHbp v2 amino acid sequence includes a substitution at V33, this preferably is not with isoleucine. Where the mutant fHbp v2 amino acid sequence includes a substitution at I113, this preferably is not with threonine or with alanine. Where the mutant fHbp v2 amino acid sequence includes a substitution at S151, this preferably is not with phenylalanine. Where the mutant fHbp v2 amino acid sequence includes a substitution at both H239 and E240, this preferably is not to R239 and Q240.

Where more than one substitution is made, these may be selected from groups 2A to 2O as follows:
2A: residues 239 and 240 e.g. mutant #1.
2B: residues 32 and 123 e.g. mutant #3.
2C: residues 125 and 126 e.g. mutant #5.
2D: residues 100, 125 and 126 e.g. mutant #6.
2E: residues 33 and 39 e.g. mutant #8.
2F: residues 41 and 69 e.g. mutant #9.
2G: residues 122 and 151 e.g. mutant #10.

2H: residues 100, 125, 126, 239 and 240 e.g. mutant #11.
2I: residues 32 and 125 e.g. mutants #19 and #21.
2J: residues 32, 123 and 125 e.g. mutants #20 and #22.
2K: residues 33 and 39, both substituted by Cys e.g. mutant #8.
2L: residues 41 and 69, both substituted by Cys e.g. mutant #9.
2M: residues 122 and 151, both substituted by Cys e.g. mutant #10.
2N: residues 123, 124, 125, 126, 127 and 128 e.g. mutant #12.
2O: residues 32, 123, 124, 125, 126, 127 and 128.

Thus, for example, if residue 239 is to be substituted then a preferred second residue for substitution is 240 (i.e. group 2A); moreover, residues 100, 125 and 126 might also be modified (i.e. group 2H, which is a combination of groups 2A and 2D). Within groups 2A to 2N & 2O, preferred substitutions at the specified positions are those listed above. For groups 2K, 2L & 2M, the intention is to introduce a disulfide bridge. Within groups 2A to 2N, preferred mutants are 2A, 2B, 2C, 2D, 2I, 2J, and 2N. More preferred are 2C, 2I, and 2N, with 2N being particularly preferred. Group 2B provides the most preferred mutations, and in particular S32V and L123R (e.g. SEQ ID NOs: 20 and 45). Group 2O is another preferred set of mutations, which combines 2B, 2C and three further mutations (e.g. to give SEQ ID NO: 58).

The amino acid residues noted for mutation in a v2 sequence are numbered relative to SEQ ID NO: 5 which is from strain 2996. The corresponding amino acid residues in a v2 fHbp from any other strain can be readily identified by sequence alignment e.g. being the amino acid which, when aligned to SEQ ID NO: 5 using a pairwise alignment algorithm (e.g. the Needleman-Wunsch global alignment algorithm, as detailed below), aligns with the amino acid mentioned herein. Often the amino acid will be the same as seen in SEQ ID NO: 5 (e.g. residue 32 will be serine), but the alignment will easily identify if this is not the case.

In addition to the mutation(s) noted above, which aim to increase stability, a polypeptide of the invention can include one or more further mutation(s) e.g. to disrupt the polypeptide's interaction with siderophores or, more preferably, to disrupt the polypeptide's ability to bind to fH.

References 19 and 25 report that the interaction between fH and v2 fHbp can be disrupted by mutations at residues R80, D211, E218, E248, T220+H222 (double mutation), and G236. Numbered according to SEQ ID NO: 5, these residues are R73, D203, E210, E240, T213+H215, and G228. Of these positions, polypeptides mutated at D203, E210 or T213+H215 are preferred because reference 25 reports no impairment of important epitopes in these mutants. The specific substitutions studied in reference 25 were R73A, D203A, E210A, T213A+H215A, G228I, and E240A; these substitutions are suitable for use according to the invention.

Reference 24 reports that the interaction between fH and v2 fHbp can be disrupted by mutations at residues R145, S193, F194, L195, A265, E267, K268, V272, I273, L274, E283, T286, H288, F292, T304, and E313 and E283+T304 (double mutation). Numbered according to SEQ ID NO: 5, these residues are R73, S121, F122, L123, A192, E194, K195, V199, I200, L201, E210, T213, H215, F219, T231, and E240 and E210+T231. Four of these overlap with reference 25 (E210, T213, H215, E240). The specific substitutions studied in reference 24 used alanine (except for A265P and T304E), and these substitutions are suitable for use according to the invention.

Reference 24 reports that certain substitutions in v2 can increase affinity for fH, and these should be avoided if the intention is to disrupt binding to fH e.g. E85 in SEQ ID NO: 5 (residue 157 in ref. 24).

Residues which interact with siderophores can be mutated, using the guidance in references 16 and 34 e.g. by aligning SEQ ID NO: 5 herein with SEQ ID NO: 4 of reference 16 to identify residues which can interact with siderophores e.g. with catecholates, hydroxamates or carboxylates.

Further residues which can be mutated include, but are not limited to, S23, L24, D30, Q31, R34, D95, and/or L102 e.g. using the mutations suggested in reference 35.

The polypeptide of the first embodiment can comprise any of SEQ ID NOs: 18 to 36. Similarly, taking into account the 'ΔG' mutation (i.e. truncation of the nascent N-terminus up to and including the native poly-Gly sequence), the polypeptide of the first embodiment can comprise any of SEQ ID NOs: 18 to 36 excluding amino acids 1-26 thereof. For example, the polypeptide of the first embodiment can comprise SEQ ID NO: 45, or can comprise SEQ ID NO: 58.

Considering the possibility of further point mutations (e.g. to disrupt interactions with siderophores and/or fH) the polypeptide of the first embodiment can comprise any of SEQ ID NOs: 18 to 36 (or any of SEQ ID NOs: 18 to 36 excluding amino acids 1-26 thereof, such as SEQ ID NO: 45) but modified by up to 5 single amino acid changes (i.e. 1, 2, 3, 4 or 5 single amino acid substitutions, deletions and/or insertions) provided that the modified sequence can, after administration to a host animal, elicit antibodies which bind to a meningococcal fHbp polypeptide consisting of the amino acid sequence of SEQ ID NO: 46. Such amino acid changes should not reverse the mutations in these sequences relative to the wild-type sequence e.g. SEQ ID NO: 45 should not be mutated at residue V32 or R123.

The invention also provides a polypeptide comprising a fHbp v2 amino acid sequence, wherein the v2 amino acid sequence is identical to a v2 wild-type amino acid sequence except for a mutation at the amino acid position corresponding to Leu-123 of SEQ ID NO: 5, provided that the mutation is not a substitution to alanine (e.g. wherein the mutation is a substitution to arginine). For instance, the polypeptide can comprise SEQ ID NO: 5, but with a mutation (other than L123A) at L123.

SEQ ID NOs: 59 and 60 are two further examples of v2 mutants, namely the mature form of mutants #3 & #4 for strain 8047.

Mutations Relative to SEQ ID NO: 17

Polypeptides of the second embodiment of the invention comprise an amino acid sequence which has at least j % identity to SEQ ID NO: 17, and/or comprise a fragment of SEQ ID NO: 17. In comparison to SEQ ID NO: 17, however, this amino sequence has a modification at one or more of amino acid residues S32, I33, L39, L41, F72, V103, T116, F125, L126, V127, S128, G129, L130, G131, S154, H242, and/or E243 e.g. at 2, 3, 4, 5 or more of these 17 residues. These residues are numbered according to SEQ ID NO: 17; to match the nascent wild-type sequence (SEQ ID NO: 3), the numbering should change +31 (i.e. Ser-32 of SEQ ID NO: 17 is Ser-63 of SEQ ID NO: 3), and to match the mature wild-type sequence (SEQ ID NO: 40) the numbering should change +12.

Preferred residues for mutation are S32, V103, L126, V127, S128, G129, L130, G131, H242, and/or E243. Within this subset, preferred residues are S32, L126, V127, S128, G129, L130, and/or G131. The most preferred positions are S32, L126, V127, S128, G129, L130, and/or G131, with residues S32 and/or L126 being particularly preferred e.g. S32V and/or L126R.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative. In some embodiments the substitution does not use alanine.

Preferred substitutions at the specified residues are as follows: S32V; I33C; L39C; L41C; F72C; V103T; T116S; F125C; L126R; V127I; S128G or S128T; G129D; L130I; G131A; S154C; H242R; E243H.

Where the mutant fHbp v3 amino acid sequence includes a substitution at E243, this substitution will not be with alanine if only E243 is mutated, although it can be alanine if a further amino acid listed in (b) is substituted e.g. if residues E243 and H242 are both mutated. Ideally, E243 is not mutated on its own, and so a mutant fHbp v3 amino acid sequence with a substitution at E243 should also include a substitution at a second residue e.g. at both E243 and H242.

Where the mutant fHbp v3 amino acid sequence includes a substitution at F125, this substitution will not be with alanine if only F125 is mutated, although it can be alanine if a further amino acid listed in (b) is substituted e.g. if residues F125 and S154 are both mutated. Ideally, F125 is not mutated on its own, and so a mutant fHbp v3 amino acid sequence with a substitution at F125 should also include a substitution at a second residue. When F125 is substituted it is preferred that S154 is also substituted e.g. both are substituted with cysteine, to permit formation of a disulfide bridge.

Where the mutant fHbp v3 amino acid sequence includes a substitution at L126, this substitution will not be with alanine if only L126 is mutated, although it can be alanine if a further amino acid listed in (b) is substituted e.g. if residues L126 and S32 are both mutated. If L126 is mutated on its own, substitution with arginine is preferred. In some embodiments, however, L126 is not mutated on its own, and so a mutant fHbp v3 amino acid sequence with a substitution at L126 can also include a substitution at a second residue. When L126 is substituted it can be preferred that: (i) S32 is also substituted, and optionally S128 is also substituted; or (ii) one or more of residues 127-131 is/are also substituted.

Where the mutant fHbp v3 amino acid sequence includes a substitution at V127, it is preferred that this substitution will not be with alanine if only V127 is mutated, although it can be alanine if a further amino acid listed in (b) is substituted e.g. if one or more of residues 126-131 are also mutated. If V127 is mutated on its own, substitution with isoleucine is preferred. Ideally, however, V127 is not mutated on its own, and so a mutant fHbp v3 amino acid sequence with a substitution at V127 should also include a substitution at a second residue. When V127 is substituted it is preferred that one or more of residues 127-131 is/are also substituted.

Where the mutant fHbp v3 amino acid sequence includes a substitution at L130, it is preferred that this substitution will not be with alanine if only L130 is mutated, although it can be alanine if a further amino acid listed in (b) is substituted e.g. if one or more of residues 126-131 are also mutated. If L130 is mutated on its own, substitution with isoleucine is preferred. Ideally, however, L130 is not mutated on its own, and so a mutant fHbp v3 amino acid sequence with a substitution at L130 should also include a substitution at a second residue. When L130 is substituted it is preferred that one or more of residues 127-131 is/are also substituted.

Where the mutant fHbp v3 amino acid sequence includes a substitution at S32, it is preferred that this substitution will not be with alanine if only S32 is mutated, although it can be alanine if a further amino acid listed in (b) is substituted e.g. if one or more of residues if residues L126 and S32 are both mutated. If S32 is mutated on its own, substitution with valine is preferred. Ideally, however, S32 is not mutated on its own, and so a mutant fHbp v3 amino acid sequence with a substitution at S32 should also include a substitution at a second residue. When S32 is substituted it is preferred that (i) L126 is also substituted, and optionally S128 us also substituted, or (ii) S128 is also substituted.

Where the mutant fHbp v3 amino acid sequence includes a substitution at T113, this substitution will not be with alanine if only T113 is mutated, although it can be alanine if a further amino acid listed in (b) is substituted. If T113 is mutated on its own, substitution with serine is preferred.

Where the mutant fHbp v3 amino acid sequence includes a substitution at 133, this preferably is not with valine. Where the mutant fHbp v3 amino acid sequence includes a substitution at T116, this preferably is not with isoleucine. Where the mutant fHbp v3 amino acid sequence includes a substitution at G129, this preferably is not with serine. Where the mutant fHbp v3 amino acid sequence includes a substitution at both H242 and E243, this preferably is not to R242 and Q243.

Where more than one substitution is made, these may be selected from groups 3A to 3O as follows:
3A: residues 242 and 243.
3B: residues 32 and 126.
3C: residues 128 and 129.
3D: residues 103, 128 and 129.
3E: residues 33 and 39.
3F: residues 41 and 72.
3G: residues 125 and 154.
3H: residues 103, 128, 129, 242 and 243.
3I: residues 32 and 128.
3J: residues 32, 126 and 128.
3K: residues 33 and 39, both substituted by Cys.
3L: residues 41 and 72, both substituted by Cys.
3M: residues 125 and 154, both substituted by Cys.
3N: residues 126, 127, 128, 129, 130 and 131.
3O: residues 32, 126, 127, 128, 129, 130 and 131.

Thus, for example, if residue 242 is to be substituted then a preferred second residue for substitution is 243 (i.e. group 3A); moreover, residues 103, 128 and 129 might also be modified (i.e. group 3H, which is a combination of groups 3A and 3D). Within groups 3A to 3N & 3O, preferred substitutions at the specified positions are those listed above. For groups 3K, 3L & 3M, the intention is to introduce a disulfide bridge. Within groups 3A to 3N, preferred mutants are 3A, 3B, 3C, 3D, 3I, 3J, and 3N. More preferred are 3C, 3I, and 3N, with 3N being particularly preferred. Group 3B provides the most preferred mutations, and in particular S32V and L126R (e.g. comprising SEQ ID NO: 44). Group 3O is another preferred mutation, which combines 3B, 3C and three further mutations (e.g. to give SEQ ID NO: 61). Mutation L126R alone provides SEQ ID NO: 53.

The amino acid residues noted for mutation in a v3 sequence are numbered relative to SEQ ID NO: 17 which is from strain M1239. The corresponding amino acid residues in a v3 fHbp from any other strain can be readily identified by sequence alignment e.g. being the amino acid which, when aligned to SEQ ID NO: 17 using a pairwise alignment algorithm (e.g. the Needleman-Wunsch global alignment algorithm, as detailed below), aligns with the amino acid mentioned herein. Often the amino acid will be the same as seen in SEQ ID NO: 17 (e.g. residue 32 will be serine), but the alignment will easily identify if this is not the case.

In addition to the mutation(s) noted above, which aim to increase stability, a polypeptide of the invention can include one or more further mutation(s) e.g. to disrupt the polypeptide's interaction with siderophores or, more preferably, to disrupt the polypeptide's ability to bind to fH.

Reference 24 reports that the interaction between fH and v3 fHbp can be disrupted by mutations at residues Q107, I147, L156, A157, L195, V196, V272, E283, T286, T304, V311, E313 and E283+T304 (double mutation). Numbered according to SEQ ID NO: 17, these residues are: Q35, I78, L87, A88, L126, V127, V202, E213, T216, T234, V241, E243 and E213+T234. The specific substitutions studied in reference 24 used alanine (except for A157E and T231E), and these substitutions are suitable for use according to the invention. Residues T216 and E243 are also reported in reference 23. Reference 36 reports that the interaction between fH and v3 fHbp can be disrupted by mutations at residues H288 and G318 (H218 and G248 numbered according to SEQ ID NO: 17), and these substitutions are suitable for use according to the invention e.g. H218R, G248D.

Ref 24 reports that certain substitutions in v3 can increase affinity for fH, and these should be avoided if the intention is to disrupt binding to fH e.g. P44 in SEQ ID NO: 17 (residue 106 in ref. 24).

Residues which interact with siderophores can be mutated, using the guidance in references 16 and 34 e.g. by aligning SEQ ID NO: 17 herein with SEQ ID NO: 4 of reference 16 to identify residues which can interact with siderophores e.g. with catecholates, hydroxamates or carboxylates.

The polypeptide of the second embodiment can comprise any of SEQ ID NOs: 41 to 44. Considering the possibility of further point mutations (e.g. to disrupt interactions with siderophores and/or fH) the polypeptide of the first embodiment can comprise any of SEQ ID NOs: 41 to 44 but modified by up to 5 single amino acid changes (i.e. 1, 2, 3, 4 or 5 single amino acid substitutions, deletions and/or insertions) provided that the modified sequence can, after administration to a host animal, elicit antibodies which bind to a meningococcal fHbp polypeptide consisting of the amino acid sequence of SEQ ID NO: 40. Such amino acid changes should not reverse the mutations in these sequences relative to the wild-type sequence e.g. SEQ ID NO: 44 should not be mutated at residue V32 or R126.

The invention also provides a polypeptide comprising a fHbp v3 amino acid sequence, wherein the v3 amino acid sequence is identical to a v3 wild-type amino acid sequence except for a mutation at the amino acid position corresponding to Leu-126 of SEQ ID NO: 17, provided that the mutation is not a substitution to alanine (e.g. wherein the mutation is a substitution to arginine). For instance, the polypeptide can comprise SEQ ID NO: 17, but with a mutation (other than L126A) at L126.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N. meningitidis* culture), etc. Heterologous expression in an *E. coli* host is a preferred expression route.

Polypeptides of the invention are ideally at least 100 amino acids long e.g. 150aa, 175aa, 200aa, 225aa, or longer. They include a mutant fHbp v2 and/or v3 amino acid sequence, and the mutant fHbp v2 or v3 amino acid sequence should similarly be at least 100 amino acids long e.g. 150aa, 175aa, 200aa, 225aa, or longer.

The fHbp is naturally a lipoprotein in *N. meningitidis*. It has also been found to be lipidated when expressed in *E. coli* with its native leader sequence or with heterologous leader sequences. Polypeptides of the invention may have a N-terminus cysteine residue, which may be lipidated e.g. comprising a palmitoyl group, usually forming tripalmitoyl-S-glyceryl-cysteine. In other embodiments the polypeptides are not lipidated.

Polypeptides are preferably prepared in substantially pure or substantially isolated form (i.e. substantially free from other Neisserial or host cell polypeptides). In general, the polypeptides are provided in a non-naturally occurring environment e.g. they are separated from their naturally-occurring environment. In certain embodiments, the polypeptide is present in a composition that is enriched for the polypeptide as compared to a starting material. Thus purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, glycosylated, non-glycosylated, lipidated, disulfide bridges, etc.).

SEQ ID NOs 4, 5, 17 and 40 do not include a N-terminus methionine. If a polypeptide of the invention is produced by translation in a biological host then a start codon is required, which will provide a N-terminus methionine in most hosts. Thus a polypeptide of the invention will, at least at a nascent stage, include a methionine residue upstream of said SEQ ID NO sequence.

Cleavage of nascent sequences means that the mutant fHbp v2 or v3 amino acid sequence might itself provide the polypeptide's N-terminus. In other embodiments, however, a polypeptide of the invention can include a N-terminal sequence upstream of the mutant fHbp v2 or v3 amino acid sequence. In some embodiments the polypeptide has a single methionine at the N-terminus immediately followed by the mutant fHbp v2 or v3 amino acid sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. His where n=4, 5, 6, 7, 8, 9, 10 or more). Other suitable N-terminal amino acid sequences will be apparent to those skilled in the art e.g. the native upstream sequences present in SEQ ID NO: 2 or SEQ ID NO: 3.

A polypeptide of the invention may also include amino acids downstream of the final amino acid of the mutant fHbp v2 or v3 amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. His where n=4, 5, 6, 7, 8, 9, 10 or more), or sequences which enhance polypeptide stability. Other suitable C-terminal amino acid sequences will be apparent to those skilled in the art.

In some embodiments, the invention excludes polypeptides which include a histidine tag (cf. refs. 24 & 25), and in particular a hexahistidine tag at the C-terminus.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention may be attached or immobilised to a solid support.

Polypeptides of the invention may comprise a detectable label e.g. a radioactive label, a fluorescent label, or a biotin label. This is particularly useful in immunoassay techniques.

As disclosed in reference 164, fHbp can be split into three domains, referred to as A, B and C. Taking SEQ ID NO: 1, the three domains are (A) 1-119, (B) 120-183 and (C) 184-274:

MNRTAFCCLSLTTALILTACSSGGGGVAADIGAGLADALTAPLDHKDKGL

QSLTLDQSVRKNEKLKLAAQGAEKTYGNGDSLNTGKLKNDKVSRFDFIRQ

IEVDGQLITLESGEFQVYK<u>QSHSALTAFQTEQIQDSEHSGKMVAKRQFRI</u>

<u>GDIAGEHTSFDKLPEGGRATYRGTAFGSDDAGG</u>KLTYTIDFAAKQGNGKI

EHLKSPELNVDLAAADIKPDGKRHAVISGSVLYNQAEKGSYSLGIFGGKA

QEVAGSAEVKTVNGIRHIGLAAKQ

The mature form of domain 'A', from Cys-20 at its N-terminus to Lys-119, is called '$A_{mature}$'.

Multiple fHbp sequences are known and these can readily be aligned using standard methods. By such alignments the skilled person can identify (a) domains 'A' (and '$A_{mature}$'), 'B' and 'C' in any given fHbp sequence by comparison to the coordinates in the MC58 sequence, and (b) single residues in multiple fHbp sequences e.g. for identifying substitutions. For ease of reference, however, the domains are defined below:

Domain 'A' in a given fHbp sequence is the fragment of that sequence which, when aligned to SEQ ID NO: 1 using a pairwise alignment algorithm, starts with the amino acid aligned to Met-1 of SEQ ID NO: 1 and ends with the amino acid aligned to Lys-119 of SEQ ID NO: 1.

Domain '$A_{mature}$' in a given fHbp sequence is the fragment of that sequence which, when aligned to SEQ ID NO: 1 using a pairwise alignment algorithm, starts with the amino acid aligned to Cys-20 of SEQ ID NO: 1 and ends with the amino acid aligned to Lys-119 of SEQ ID NO: 1.

Domain 'B' in a given fHbp sequence is the fragment of that sequence which, when aligned to SEQ ID NO: 1 using a pairwise alignment algorithm, starts with the amino acid aligned to Gln-120 of SEQ ID NO: 1 and ends with the amino acid aligned to Gly-183 of SEQ ID NO: 1.

Domain 'C' in a given fHbp sequence is the fragment of that sequence which, when aligned to SEQ ID NO: 1 using a pairwise alignment algorithm, starts with the amino acid aligned to Lys-184 of SEQ ID NO: 1 and ends with the amino acid aligned to Gln-274 of SEQ ID NO: 1.

The preferred pairwise alignment algorithm for defining the domains is the Needleman-Wunsch global alignment algorithm [158], using default parameters (e.g. with Gap opening penalty=10.0, and with Gap extension penalty=0.5, using the EBLOSUM62 scoring matrix). This algorithm is conveniently implemented in the needle tool in the EMBOSS package [159].

In some embodiments, a mutant fHbp v2 or v3 amino acid sequence of the invention is truncated to remove its domain A. In general, however, it is preferred that the mutant fHbp v2 or v3 amino acid sequence should include both a N-terminal β-barrel and a C-terminal β-barrel.

In some embodiments, a polypeptide comprises an amino acid sequence as described above, except that up to 10 amino acids (i.e. 1, 2, 3, 4, 5, 6, 7, 8, 9 or 10) at the N-terminus and/or up to 10 amino acids (i.e. 1, 2, 3, 4, 5, 6, 7, 8, 9 or 10) at the C-terminus are deleted.

Polypeptides of the invention typically consist of an artificial amino acid sequence, namely a sequence which is not present in any naturally-occurring meningococci.

Affinity for factor H can be quantitatively assessed using surface plasmon resonance e.g. as disclosed in references 18 and 21-24 with immobilised human fH. Mutations which provide an affinity reduction (i.e. an increase in the dissociation constant, $K_D$) of at least 10-fold, and ideally at least 100-fold, is preferred (when measured under the same experimental conditions relative to the same polypeptide but without the mutation).

Nucleic Acids

The invention provides nucleic acid encoding a polypeptide of the invention as defined above.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label.

The invention also provides vectors (such as plasmids) comprising nucleotide sequences of the invention (e.g. cloning or expression vectors, such as those suitable for nucleic acid immunisation) and host cells transformed with such vectors.

Bactericidal Responses

Preferred polypeptides of the invention can elicit antibody responses that are bactericidal against meningococci. Bactericidal antibody responses are conveniently measured in mice and are a standard indicator of vaccine efficacy (e.g. see end-note 14 of ref. 37; also ref. 38).

Polypeptides of the first embodiment invention can preferably elicit an antibody response which is bactericidal against a *N. meningitidis* strain which expresses a v2 fHbp sequence e.g. one or more of strains 961-5945, 2996, 96217, 312294, 11327, a22, gb013 (=M01-240013), e32, m1090, m4287, 860800, 599, 95N477, 90-18311, c11, m986, m2671, 1000, m1096, m3279, bz232, dk353, m3697, ngh38, and/or L93/4286. Bactericidal responses can for instance be assessed against var2 strain M2091 (ATCC 13091).

Preferred polypeptides of the first embodiment invention can elicit antibodies in a mouse which are bactericidal against strain M2091 in a serum bactericidal assay.

Polypeptides of the second embodiment invention can preferably elicit an antibody response which is bactericidal against a *N. meningitidis* strain which expresses a v3 fHbp sequence e.g. one or more of strains M1239, 16889, gb355 (=M01-240355), m3369, m3813, ngp165. Bactericidal responses can for instance be assessed against var3 strain M01-240355, which is a *Neisseria* MLST reference strains (id 19265 in ref. 39) which has been fully sequenced (see EMBL ID CP002422 [40])

Preferred polypeptides of the second embodiment invention can elicit antibodies in a mouse which are bactericidal against strain M01-240355 in a serum bactericidal assay.

For example, an immunogenic composition comprising these polypeptides can provide a serum bactericidal titer of ≥1:4 using the Goldschneider assay with human complement [41-43], and/or providing a serum bactericidal titer of ≥1:128 using baby rabbit complement.

Immunisation

Polypeptides of the invention may be used as the active ingredient of immunogenic compositions, and so the invention provides an immunogenic composition (e.g. a vaccine) comprising a polypeptide of the invention.

The invention also provides a method for raising an antibody response in a mammal, comprising administering an immunogenic composition of the invention to the mammal. The antibody response is preferably a protective and/or bactericidal antibody response. The invention also provides polypeptides of the invention for use in such methods.

The invention also provides a method for protecting a mammal against a Neisserial (e.g. meningococcal) infection, comprising administering to the mammal an immunogenic composition of the invention.

The invention provides polypeptides of the invention for use as medicaments (e.g. as immunogenic compositions or as vaccines) or as diagnostic reagents. It also provides the use of nucleic acid or polypeptide of the invention in the manufacture of a medicament for preventing Neisserial (e.g. meningococcal) infection in a mammal.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N. meningitidis* (for example in serogroup B).

Efficacy of therapeutic treatment can be tested by monitoring Neisserial infection after administration of the composition of the invention. Efficacy of prophylactic treatment can be tested by monitoring immune responses against fHbp after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 44.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. Compositions suitable for parenteral injection are most preferred.

The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [45]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. The term "prevention" means that the progression of the disease is reduced and/or eliminated, or that the onset of the disease is eliminated. For example, the immune system of a subject may be primed (e.g by vaccination) to trigger an immune response and repel infection such that the onset of the disease is eliminated. A vaccinated subject may thus get infected, but is better able to repel the infection than a control subject. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of ref. 46.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of ref. 46). The salts can take any suitable form (e.g. gel, crystalline, amorphous, etc.).

Further Antigenic Components

Compositions of the invention include mutant v2 and/or v3 fHbp sequence. It is useful if the composition should not include complex or undefined mixtures of antigens e.g. it is preferred not to include outer membrane vesicles in the composition. Polypeptides of the invention are preferably expressed recombinantly in a heterologous host and then purified.

As well as including a fHbp polypeptide, a composition of the invention may also include one or more further neisserial immunogen(s), as a vaccine which targets more than one immunogen per bacterium decreases the possibility of selecting escape mutants. Thus a composition can include a second polypeptide that, when administered to a mammal, elicits an antibody response that is bactericidal against meningococcus. The second polypeptide can be a meningococcal fHbp, but will often not be a fHbp e.g. it may be a NHBA sequence, a NadA sequence, etc.

Any such further neisserial immunogen may be present as a separate polypeptide to the mutant v2 or v3 fHbp of the invention or may be present as a fusion polypeptide with the modified fHbp. For instance, fusion of meningococcal 936 polypeptide and fHbp polypeptides is known [55,56]. Fusion proteins comprising SEQ ID NO: 44 and/or SEQ ID NO: 45 are particularly preferred, optionally wherein SEQ ID NO: 44 and/or 45 is/are modified by up to 5 single amino acid changes (i.e. 1, 2, 3, 4 or 5 single amino acid substitutions, deletions and/or insertions) as described elsewhere herein.

A composition of the invention may include a NHBA antigen. The NHBA antigen was included in the published genome sequence for meningococcal serogroup B strain MC58 [47] as gene NMB2132 (GenBank accession number GI:7227388; SEQ ID NO: 6 herein). The sequences of NHBA antigen from many strains have been published since then. For example, allelic forms of NHBA can be seen in FIGS. 5 and 15 of reference 48, and in example 13 and FIG. 21 of reference 1 (SEQ IDs 3179 to 3184 therein). Various immunogenic fragments of the NHBA antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most useful NHBA antigens of the invention can elicit antibodies which, after administration to a subject, can bind to a meningococcal polypeptide consisting of amino acid sequence SEQ ID NO: 6. Advantageous NHBA antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [47] as gene NMB1994 (GenBank accession number GI:7227256; SEQ ID NO: 7 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 7. The most useful NadA antigens of the invention can elicit antibodies which, after administration to a subject, can bind to a meningococcal polypeptide consisting of amino acid sequence SEQ ID NO: 7. Advantageous NadA antigens for use with the invention can elicit bactericidal anti-meningococcal antibodies after administration to a subject. SEQ ID NO: 15 is one such fragment.

A composition of the invention may include a NspA antigen. The NspA antigen was included in the published genome sequence for meningococcal serogroup B strain MC58 [47] as gene NMB0663 (GenBank accession number GI:7225888; SEQ ID NO: 8 herein). The antigen was previously known from references 49 & 50. The sequences of NspA antigen from many strains have been published since then. Various immunogenic fragments of NspA have also been reported. Preferred NspA antigens for use with the invention comprise n amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 8. The most useful NspA antigens of the invention can elicit antibodies which, after administration to a subject, can bind to a meningococcal polypeptide consisting of amino acid sequence SEQ ID NO: 8. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [47] as gene NMB1668 (SEQ ID NO: 9 herein). The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 9, where the value of i is 50, 60, 70, 80, 90, 95, 99 or more. In other embodiments a HmbR sequence used according to the invention may comprise a fragment of at least j consecutive amino acids from SEQ ID NO: 9, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 9 and/or (ii) comprising a fragment of at least j consecutive amino acids from SEQ ID NO: 9. Preferred fragments of j amino acids comprise an epitope from SEQ ID NO: 9. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 51. The most useful HmbR antigens of the invention can elicit antibodies which, after administration to a subject, can bind to a meningococcal polypeptide consisting of amino acid sequence SEQ ID NO: 9. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [47] as gene NMB0992 (GenBank accession number GI:7226232; SEQ ID NO: 10 herein). The sequences of NhhA antigen from many strains have been published since e.g. refs 48 & 52, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10. The most useful NhhA antigens of the invention can elicit antibodies which, after administration to a subject, can bind to a meningococcal polypeptide consisting of amino acid sequence SEQ ID NO: 10. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [47] as gene NMB1985 (GenBank accession number GI:7227246; SEQ ID NO: 11 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11. The most useful App antigens of the invention can elicit antibodies which, after administration to a subject, can bind to a meningococcal polypeptide consisting of amino acid sequence SEQ ID NO: 11. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [47] as gene NMB0182 (GenBank accession number GI:7225401; SEQ ID NO: 12 herein). The sequences of Omp85 antigen from many strains have been published since then. Further information on Omp85 can be found in references 53 and 54. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12. The most useful Omp85 antigens of the invention can elicit antibodies which, after administration to a subject, can bind to a meningococcal polypeptide consisting of amino acid sequence SEQ ID NO: 12. Advantageous Omp85 antigens for use with the invention can elicit bactericidal anti-meningococcal antibodies after administration to a subject.

A composition of the invention may include a 936 antigen. The 936 antigen was included in the published genome sequence for meningococcal serogroup B strain MC58 [47] as gene NMB2091 (SEQ ID NO: 13 herein). Preferred 936 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13. The most useful 936 antigens of the invention can elicit antibodies which, after administration to a subject, can bind to a meningococcal polypeptide consisting of amino acid sequence SEQ ID NO: 13. The 936 antigen is a good fusion partner for fHbp (e.g. see references 55 & 56).

A composition may comprise: a polypeptide comprising SEQ ID NO: 14; a polypeptide comprising SEQ ID NO: 15; and a polypeptide of the invention comprising a mutant fHbp v2 amino acid sequence and SEQ ID NO: 13 (cf. refs. 55 & 56).

A composition may comprise: a polypeptide comprising SEQ ID NO: 14; a polypeptide comprising SEQ ID NO: 15; and a polypeptide of the invention comprising a mutant fHbp v3 amino acid sequence and SEQ ID NO: 13 (cf. refs. 55 & 56).

In some embodiments, a polypeptide of the invention is combined with a further meningococcal fHbp sequence. In particular, a v2 polypeptide can be combined with a v1 and/or a v3 polypeptide to increase the spectrum of strain coverage [162]. Thus a composition can comprise: (i) a polypeptide of the invention comprising a mutant fHbp v2 amino acid sequence; and (ii) a v1 fHbp polypeptide and/or a v3 fHbp polypeptide. In other embodiments, a polypeptide of the invention can comprise (i) a mutant fHbp v2 amino acid sequence and (ii) a v1 fHbp amino acid sequence and/or a v3 fHbp amino acid sequence. Thus the v1 and/or v3 sequences can be combined with the mutant v2 sequence as separate entities in a composition, or within a fusion polypeptide.

Similarly, a v3 polypeptide can be combined with a v1 and/or a v2 polypeptide to increase the spectrum of strain coverage [162]. Thus a composition can comprise: (i) a polypeptide of the invention comprising a mutant fHbp v3 amino acid sequence; and (ii) a v1 fHbp polypeptide and/or a v2 fHbp polypeptide. In other embodiments, a polypeptide of the invention can comprise (i) a mutant fHbp v3 amino acid sequence and (ii) a v1 fHbp amino acid sequence and/or a v2 fHbp amino acid sequence. Thus the v1 and/or v2 sequences can be combined with the mutant v3 sequence as separate entities in a composition, or within a fusion polypeptide.

Moreover, mutant v2 and v3 polypeptides can be combined with each other to increase strain coverage. Thus a composition can comprise: (i) a polypeptide of the invention comprising a mutant fHbp v2 amino acid sequence; (ii) a polypeptide of the invention comprising a mutant fHbp v3 amino acid sequence; and (iii) a fHbp v1 polypeptide. In other embodiments, a polypeptide of the invention can comprise (i) a mutant fHbp v2 amino acid sequence (ii) a mutant v3 fHbp amino acid sequence and (iii) a fHbp v1 amino acid sequence. Thus the mutant v2 and v3 sequences can be combined with a v1 sequence as separate entities in a composition, or within a fusion polypeptide. The v1 sequence can be a wild-type sequence or a mutant sequence.

A v1 fHbp can comprise (a) an amino acid sequence which has at least k % identity to SEQ ID NO: 16, and/or (b) a fragment of SEQ ID NO: 16. Information about 'k' and fragments are given above. The fragment will typically include at least one epitope from SEQ ID NO: 16, and the v1 fHbp polypeptide will include at least one epitope which is not present in the v2 or v3 amino acid sequence of the invention, such that antibodies elicited by the v1 fHbp can recognise v1 strains. Ideally, the v1 fHbp can elicit antibodies which are bactericidal against v1 strains e.g. against strain MC58 (available from the ATCC as 'BAA-335'). The v1 fHbp can include an amino acid mutation which disrupts its ability to bind to fH.

A v2 fHbp can comprise (a) an amino acid sequence which has at least k % identity to SEQ ID NO: 5, and/or (b) a fragment of SEQ ID NO: 5. Information about 'k' and fragments are given above. The fragment will typically include at least one epitope from SEQ ID NO: 5, and the v2 fHbp polypeptide will include at least one epitope which is not present in the v3 amino acid sequence of the invention, such that antibodies elicited by the v2 fHbp can recognise v2 strains. Ideally, the v2 fHbp can elicit antibodies which are bactericidal against v2 strains e.g. against strain M2091 (ATCC 13091). The v2 fHbp can be a polypeptide of the first embodiment.

A v3 fHbp can comprise (a) an amino acid sequence which has at least k % identity to SEQ ID NO: 17, and/or (b) a fragment of SEQ ID NO: 17. Information about 'k' and fragments are given above. The fragment will typically include at least one epitope from SEQ ID NO: 17, and the v3 fHbp polypeptide will include at least one epitope which is not present in the v2 amino acid sequence of the invention, such that antibodies elicited by the v3 fHbp can recognise v3 strains. Ideally, the v3 fHbp can elicit antibodies which are bactericidal against v3 strains e.g. against strain M01-240355. The v3 fHbp can be a polypeptide of the second embodiment.

Thus, for instance, the invention provides a polypeptide comprising, within a single polypeptide chain, each of: (i) a fHbp v1 amino acid sequence; (ii) a mutant fHbp v2 amino acid sequence; and (iii) a mutant fHbp v3 amino acid sequence. The polypeptide can, after administration to a host animal, elicit antibodies which bind to each of: a meningococcal fHbp polypeptide consisting of the amino acid sequence of SEQ ID NO: 46; a meningococcal fHbp polypeptide consisting of the amino acid sequence of SEQ ID NO: 4; and a meningococcal fHbp polypeptide consisting of the amino acid sequence of SEQ ID NO: 40. The sequence of (i) can comprise an amino acid sequence which has at least k % identity to SEQ ID NO: 16. The sequence of (ii) can comprise an amino acid sequence which has at least k % identity to SEQ ID NO: 5, but differing from SEQ ID NO: 5 at one or more of the following residues: S32, V33, L39, L41, F69, V100, I113, F122, L123, V124, S125, G126, L127, G128, S151, H239, and/or E240. The sequence of (iii) can comprise an amino acid sequence which has at least k % identity to SEQ ID NO: 17, but differing from SEQ ID NO: 17 at one or more of the following residues: S32, 133, L39, L41, F72, V103, T116, F125, L126, V127, S128, G129, L130, G131, S154, H242, and/or E243. In a preferred embodiment: the sequence of (i) comprises SEQ ID NO: 16, optionally modified by up to 5 single amino acid changes (i.e. 1, 2, 3, 4 or 5 single amino acid substitutions, deletions and/or insertions); the sequence of (ii) comprises SEQ ID NO: 45, optionally modified by up to 5 single amino acid changes (i.e. 1, 2, 3, 4 or 5 single amino acid substitutions, deletions and/or insertions), provided such amino acid changes do not reverse the mutations in these sequences relative to the wild-type sequence; and the sequence of (iii) comprises SEQ ID NO: 44, optionally modified by up to 5 single amino acid changes (i.e. 1, 2, 3, 4 or 5 single amino acid substitutions, deletions and/or insertions e.g. to give SEQ ID NO: 53), provided such amino acid changes do not reverse the mutations in these sequences relative to the wild-type sequence. Amino acid sequences (i), (ii) and (iii) can be arranged in any order from N- to C-terminus in the polypeptide, but are preferably in the order (ii), then (iii), then (i). For instance, the invention provides a polypeptide of formula -A-B-C- wherein: A comprises SEQ ID NO: 45, optionally modified by up to 3 single amino acid substitutions; B comprises SEQ ID NO: 44, optionally modified by up to 3 single amino acid substitutions; and C comprises SEQ ID NO: 16, optionally modified by up to 3 single amino acid substitutions (e.g. substitution(s) to disrupt binding to fH). A preferred C comprises SEQ ID NO: 49, where residue Arg-34 is mutated to Ser as reported for the 'R41S' mutation in ref. 21.

A particularly preferred polypeptide comprises amino acid sequence SEQ ID NO: 47. This sequence includes, from N-terminus to C-terminus: the mutant v2 (SEQ ID NO: 45); the mutant v3 (SEQ ID NO: 44); and the mutant v1 (SEQ ID NO: 49). Between these three mutant fHbp sequences there is in each case a linker sequence, SEQ ID NO: 50. In one embodiment, the polypeptide comprises amino acid sequence SEQ ID NO: 48, which has a N-terminus methionine, then SEQ ID NO: 37, and then SEQ ID NO: 47.

SEQ ID NO: 47 (alone, or within SEQ ID NO: 48) can optionally be modified by up to 5 single amino acid changes (i.e. 1, 2, 3, 4 or 5 single amino acid substitutions, deletions and/or insertions), provided such amino acid changes do not reverse the mutations in the v1, v2, and v3 sequences relative to the wild-type sequence i.e. amino acid residues V32, R123, V285, R379, and S543 of SEQ ID NO: 47 should not be mutated to S32, L123, S285, L379, and R543. In one exceptional embodiment, however, V285 can revert to 5285 and/or V32 can revert to S32.

The mutant fusion can ideally elicit antibodies which bind to each of: a wild-type v1 meningococcal fHbp polypeptide consisting of amino acid sequence SEQ ID NO: 46; a wild-type v2 meningococcal fHbp polypeptide consisting of amino acid sequence SEQ ID NO: 4; and a wild-type v3 meningococcal fHbp polypeptide consisting of amino acid sequence SEQ ID NO: 40.

In addition to Neisserial polypeptide antigens, the composition may include antigens for immunising against other diseases or infections. For example, the composition may include one or more of the following further antigens:

- a saccharide antigen from *N. meningitidis* serogroup A, C, W135 and/or Y, such as the saccharide disclosed in ref. 57 from serogroup C (see also ref. 58) or in ref. 59.
- a saccharide antigen from *Streptococcus pneumoniae* [e.g. 60, 61, 62].
- an antigen from hepatitis A virus, such as inactivated virus [e.g. 63, 64].
- an antigen from hepatitis B virus, such as the surface and/or core antigens [e.g. 64, 65].
- a diphtheria antigen, such as a diphtheria toxoid [e.g. chapter 3 of ref. 66] e.g. the $CRM_{197}$ mutant [e.g. 67].
- a tetanus antigen, such as a tetanus toxoid (e.g. chapter 4 of ref. 66).
- an antigen from *Bordetella pertussis*, such as pertussis holotoxin (PT) and filamentous haemagglutinin (FHA) from *B. pertussis*, optionally also in combination with pertactin and/or agglutinogens 2 and 3 (e.g. refs. 68 & 69).
- a saccharide antigen from *Haemophilus influenzae* B [e.g. 58].
- polio antigen(s) [e.g. 70, 71] such as IPV.
- measles, mumps and/or rubella antigens (e.g. chapters 9, 10 & 11 of ref. 66).
- influenza antigen(s) (e.g. chapter 19 of ref. 66), such as the haemagglutinin and/or neuraminidase surface proteins.
- an antigen from *Moraxella catarrhalis* [e.g. 72].
- an protein antigen from *Streptococcus agalactiae* (group B *streptococcus*) [e.g. 73, 74].
- a saccharide antigen from *Streptococcus agalactiae* (group B *streptococcus*).
- an antigen from *Streptococcus pyogenes* (group A *streptococcus*) [e.g. 74, 75, 76].
- an antigen from *Staphylococcus aureus* [e.g. 77].

The composition may comprise one or more of these further antigens.

Toxic protein antigens may be detoxified where necessary (e.g. detoxification of pertussis toxin by chemical and/or genetic means [69]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 μg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (which could be RNA, such as a self-replicating RNA, or DNA, such as a plasmid) encoding the antigen may be used.

In some embodiments a composition of the invention comprises in addition to the fHbp sequence, conjugated capsular saccharide antigens from 1, 2, 3 or 4 of meningococcus serogroups A, C, W135 and Y. In other embodiments a composition of the invention comprises in addition to the fHbp sequence, at least one conjugated pneumococcal capsular saccharide antigen.

Meningococcus Serogroups Y, W135, C and A

Current serogroup C vaccines (Menjugate™ [57,78], Meningitec™ and NeisVac-C™) include conjugated saccharides. Menjugate™ and Meningitec™ have oligosaccharide antigens conjugated to a $CRM_{197}$ carrier, whereas NeisVac-C™ uses the complete polysaccharide (de-O-acetylated) conjugated to a tetanus toxoid carrier. The Menactra™ vaccine contains conjugated capsular saccharide antigens from each of serogroups Y, W135, C and A.

Compositions of the present invention may include capsular saccharide antigens from one or more of meningococcus serogroups Y, W135, C and A, wherein the antigens are conjugated to carrier protein(s) and/or are oligosaccharides. For example, the composition may include a capsular saccharide antigen from: serogroup C; serogroups A and C;

serogroups A, C and W135; serogroups A, C and Y; serogroups C, W135 and Y; or from all four of serogroups A, C, W135 and Y.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [79].

If hydrolysis is performed, the hydrolysate will generally be sized in order to remove short-length oligosaccharides [58]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 78, as used in Menjugate™.

The saccharide antigen may be chemically modified. This is particularly useful for reducing hydrolysis for serogroup A [80]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [80]. This modification improves resistance to hydrolysis.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique.

Typical carrier proteins are bacterial toxins, such as diphtheria or tetanus toxins, or toxoids or mutants thereof. The $CRM_{197}$ diphtheria toxin mutant [81] is useful, and is the carrier in the PREVNAR™ product. Other suitable carrier proteins include the *N. meningitidis* outer membrane protein complex [82], synthetic peptides [83,84], heat shock proteins [85,86], pertussis proteins [87,88], cytokines [89], lymphokines [89], hormones [89], growth factors [89], artificial proteins comprising multiple human $CD4^+$ T cell epitopes from various pathogen-derived antigens [90] such as N19 [91], protein D from *H. influenzae* [92-94], pneumolysin [95] or its non-toxic derivatives [96], pneumococcal surface protein PspA [97], iron-uptake proteins [98], toxin A or B from *C. difficile* [99], recombinant *P. aeruginosa* exoprotein A (rEPA) [100], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [101,102, etc.]). Other suitable techniques use carbodiimides, hydrazides, active esters, norborane, p-nitrobenzoic acid, N-hydroxysuccinimide, S-NHS, EDC, TSTU, etc.

Linkages via a linker group may be made using any known procedure, for example, the procedures described in references 103 and 104. One type of linkage involves reductive amination of the polysaccharide, coupling the resulting amino group with one end of an adipic acid linker group, and then coupling a protein to the other end of the adipic acid linker group [105,106]. Other linkers include B-propionamido [107], nitrophenyl-ethylamine [108], haloacyl halides [109], glycosidic linkages [110], 6-aminocaproic acid [111], ADH [112], $C_4$ to $C_{12}$ moieties [113] etc. As an alternative to using a linker, direct linkage can be used. Direct linkages to the protein may comprise oxidation of the polysaccharide followed by reductive amination with the protein, as described in, for example, references 114 and 115.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

Outer Membrane Vesicles

Some compositions of the invention do not include complex or undefined mixtures of antigens, which are typical characteristics of OMVs. However, the invention can be used in conjunction with OMVs, as fHbp has been found to enhance their efficacy [4], in particular by over-expressing the polypeptides of the invention in the strains used for OMV preparation. See also below.

This approach may be used in general to improve preparations of *N. meningitidis* serogroup B microvesicles [116], 'native OMVs' [117], blebs or outer membrane vesicles [e.g. refs. 118 to 123, etc.]. These may be prepared from bacteria which have been genetically manipulated [124-127] e.g. to increase immunogenicity (e.g. hyper-express immunogens), to reduce toxicity, to inhibit capsular polysaccharide synthesis, to down-regulate PorA expression, etc. They may be prepared from hyperblebbing strains [128-131]. Vesicles from a non-pathogenic *Neisseria* may be included [132]. OMVs may be prepared without the use of detergents [133,134]. They may express non-Neisserial proteins on their surface [135]. They may be LPS-depleted. They may be mixed with recombinant antigens [118,136]. Vesicles from bacteria with different class I outer membrane protein subtypes may be used e.g. six different subtypes [137,138] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2, 10; P1.12-1,13; P1.7-2,4; P1.22,14; P1.7-1,1; P1.18-1,3,6.

Host Cells

The invention provides a bacterium which expresses a polypeptide of the invention. The bacterium may be a meningococcus or an *E. coli*. The bacterium may constitutively express the polypeptide, but in some embodiments expression may be under the control of an inducible promoter. The bacterium may hyper-express the polypeptide (cf. ref. 139). Expression of the polypeptide is ideally not phase variable.

The invention also provides outer membrane vesicles prepared from a bacterium of the invention (particularly from a meningococcus). It also provides a process for producing vesicles from a bacterium of the invention. Vesicles prepared from these strains preferably include the polypeptide of the invention, which should be in an immunoaccessible form in the vesicles i.e. an antibody which can bind to purified polypeptide of the invention should also be able to bind to the polypeptide which is present in the vesicles.

These outer membrane vesicles include any proteoliposomic vesicle obtained by disruption of or blebbing from a meningococcal outer membrane to form vesicles therefrom that include protein components of the outer membrane. Thus the term includes OMVs (sometimes referred to as 'blebs'), microvesicles (MVs [116]) and 'native OMVs' ('NOMVs' [117]).

MVs and NOMVs are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 130 & 131 describe *Neisseria* with high MV production.

OMVs are prepared artificially from bacteria, and may be prepared using detergent treatment (e.g. with deoxycholate), or by non-detergent means (e.g. see reference 134). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [140 & 141] being preferred for treating *Neisseria*) at a pH sufficiently high not to precipitate the detergent [142]. Other techniques may be performed substantially in the absence of detergent [134] using techniques such as sonication, homogenisation, microfluidisation, cavitation, osmotic shock, grinding, French press, blending, etc. Methods using no or low detergent can retain useful antigens such as NspA and fHbp [134]. Thus a method may use an OMV extraction buffer with about 0.5% deoxycholate or lower e.g. about 0.2%, about 0.1%, <0.05% or zero.

A useful process for OMV preparation is described in reference 143 and involves ultrafiltration on crude OMVs, rather than instead of high speed centrifugation. The process may involve a step of ultracentrifugation after the ultrafiltration takes place. OMVs can also be purified using the two stage size filtration process described in ref. 154.

Vesicles for use with the invention can be prepared from any meningococcal strain. The vesicles will usually be from a serogroup B strain, but it is possible to prepare them from serogroups other than B (e.g. reference 142 discloses a process for serogroup A), such as A, C, W135 or Y. The strain may be of any serotype (e.g. 1, 2a, 2b, 4, 14, 15, 16, etc.), any serosubtype, and any immunotype (e.g. L1; L2; L3; L3,3,7; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3.

Bacteria of the invention may, in addition to encoding a polypeptide of the invention, have one or more further modifications. For instance, they may have a modified fur gene [144]. Expression of nspA expression may be up-regulated with concomitant porA and cps knockout. Further knockout mutants of *N. meningitidis* for OMV production are disclosed e.g. in reference 150. Reference 145 discloses the construction of vesicles from strains modified to express six different PorA subtypes. Mutant *Neisseria* with low endotoxin levels, achieved by knockout of enzymes involved in LPS biosynthesis, may also be used [146,147]. Mutant *Neisseria* engineered to reduce or switch off expression of at least one gene involved in rendering toxic the lipid A portion of LPS, in particular of lpxl1 gene, can be used with the invention [148]. Similarly, mutant *Neisseria* engineered to reduce or switch off expression of at least one gene involved in the capsular polysaccharide synthesis or export, in particular of synX and/or ctrA genes can be used with the invention. These or others mutants can all be used with the invention.

Thus a strain used with the invention may in some embodiments express more than one PorA subtype. 6-valent and 9-valent PorA strains have previously been constructed. The strain may express 2, 3, 4, 5, 6, 7, 8 or 9 of PorA subtypes: P1.7,16; P1.5-1,2-2; P1.19,15-1; P1.5-2,10; P1.12-1,13; P1.7-2,4; P1.22,14; P1.7-1,1 and/or P1.18-1,3,6. In other embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76).

In some embodiments a strain may hyper-express (relative to the corresponding wild-type strain) certain proteins. For instance, strains may hyper-express NspA, protein 287 [118], fHbp [139] (including fHbp of the invention), TbpA and/or TbpB [136], Cu,Zn-superoxide dismutase, HmbR, etc.

A gene encoding a polypeptide of the invention may be integrated into the bacterial chromosome or may be present in episomal form e.g. within a plasmid.

Advantageously for vesicle production, a meningococcus may be genetically engineered to ensure that expression of the polypeptide is not subject to phase variation. Methods for reducing or eliminating phase variability of gene expression in meningococcus are disclosed in reference 149. For example, a gene may be placed under the control of a constitutive or inducible promoter, or by removing or replacing the DNA motif which is responsible for its phase variability.

In some embodiments a strain may include one or more of the knockout and/or hyper-expression mutations disclosed in references 122, 124, 128, and 150. For instance, following the guidance and nomenclature in these four documents, useful genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; or (d) CtrA, CtrB, CtrD, FrpB, OpA, OpC, PilC, PorB, SiaD, SynA, SynB, SynX and/or SynC.

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no α chain.

Depending on the meningococcal strain used for preparing the vesicles, they may or may not include the strain's native fHbp antigen [151].

In one preferred embodiment, a meningococcus does not express a functional MltA protein. As discussed in refs. 152 & 153, knockout of MltA (the membrane-bound lytic transglycosylase, also known as GNA33) in meningococcus provides bacteria which spontaneously release large amounts of membrane vesicles into culture medium, from which they can be readily purified. For instance, the vesicles can be purified using the two stage size filtration process of ref. 154, comprising: (i) a first filtration step in which vesicles are separated from the bacteria based on their different sizes, with the vesicles passing into the filtrate; and (ii) a second filtration step in which the vesicles are retained in the retentate. The MltA mutation (down-regulation or knockout) has been used in 'GMMA' vaccines [155], and can conveniently be combined with further down regulation or knockout of in particular of at least one gene involved in rendering toxic the lipid A portion of LPS, particularly of lpxl1 and/or of at least one gene involved in the capsular polysaccharide synthesis or export, particularly of synX and/or ctrA genes. GMMA (Generalized Modules for Membrane Antigens) are genetically detoxified OMV that are produced from meningococcal strains that have been engineered to release GMMA with reduced reactogenicity and increased immunogenicity. GMMA induce less proinflammatory cytokines than OMV when tested in the monocyte activation test (MAT).

A preferred meningococcal strain for a 'GMMA' vaccine using this approach expresses a mutant v2 fHbp and/or a mutant v3 fHbp of the invention, and expression can be driven by strong promoters. Vesicles released by this strain include the mutant v2 and/or v3 fHbp proteins in immunogenic form, and administration of the vesicles can provide bactericidal antibody response as discussed in reference 155. The strain can also express a v1 fHbp, or a v1 fHbp can instead be provided as a separate recombinant protein in soluble form (and the v1 fHbp can be a wild-type or a mutant sequence e.g. mutated to disrupt its ability to bind to fH, as discussed above). The invention provides such strains, and also provides the vesicles which these strains release e.g. as purified from culture media after growth of the strains. A preferred v2 mutant for expression in these strains has a mutation at S32 and/or L123 as discussed herein, and a preferred v3 mutant for expression in these strains has a mutation at S32 and/or L126 as discussed herein. Thus vesicles prepared from meningococci expressing these v2 and v3 mutant fHbp sequences are particularly preferred immunogens for use in vaccines of the invention. A useful wild-type v2 sequence for mutagenesis in this way comprises SEQ ID NO: 51 or SEQ ID NO: 54 (comprising AG form SEQ ID NO: 55), and a useful wild-type v3 sequence for mutagenesis in this way comprises SEQ ID NO: 52.

Useful promoters for use in such strains include those disclosed in references 156 and 157. For instance, the promoter can be: (a) the promoter from a porin gene, preferably porA or porB, particularly from *N. meningitidis*; or (b) a rRNA gene promoter (such as a 16S rRNA gene), particularly from *N. meningitidis*. Where a meningococcal porin promoter is used, it is preferably from porA, and even more particularly a −10 region from a meningococcal porA gene promoter, and/or a −35 region from a meningococcal porA gene promoter (preferably wherein the −10 region and the −35 region are separated by an intervening sequence of 12-20 nucleotides, and wherein the intervening sequence either contains no poly-G sequence or includes a poly-G sequence having no more than eight consecutive G nucleotides). Where a rRNA gene promoter is used, it can comprise more particularly (i) a −10 region from a meningococcal rRNA gene promoter and/or (ii) a −35 region from a meningococcal rRNA gene promoter. It is also possible to use a hybrid of (a) and (b), for instance to have a −10 region from a porA promoter and a −35 region from a rRNA promoter (which can be a consensus −35 region). A useful promoter can thus be a promoter which includes either (i) a −10 region from a (particularly meningococcal) rRNA gene and a −35 region from a (particularly meningococcal) porA gene, or (ii) a −10 region from a (particularly meningococcal) porA gene and a −35 region from a (particularly meningococcal) rRNA gene.

If LOS is present in a vesicle it is possible to treat the vesicle so as to link its LOS and protein components ("intra-bleb" conjugation [150]).

General

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.). The term "consisting essentially of" limits the scope of a claim to the specified materials or steps "and those that do not materially affect the basic and novel characteristic(s)" of the claimed invention.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

"Sequence identity" can be determined by the Smith-Waterman homology search algorithm as implemented in the MPSRCH program (Oxford Molecular), using an affine gap search with parameters gap open penalty=12 and gap extension penalty=1, but is preferably determined by the Needleman-Wunsch global alignment algorithm [158], using default parameters (e.g. with Gap opening penalty=10.0, and with Gap extension penalty=0.5, using the EBLOSUM62 scoring matrix). This algorithm is conveniently implemented in the needle tool in the EMBOSS package [159]. Where the application refers to sequence identity to a particular SEQ ID, the identity should be calculated over the entire length of that SEQ ID.

The term "fragment" in reference to polypeptide sequences means that the polypeptide is a fraction of a full-length protein. Such fragments may possess qualitative biological activity in common with the full-length protein, for example, a fragment may contain or encode one or more epitopes, such as immunodominant epitopes, that allow similar immune response to be raised to the fragment as to the full length sequence. Polypeptide fragments generally have an amino (N) terminus portion and/or carboxy (C) terminus portion deleted as compared to the native protein, but wherein the remaining amino acid sequence of the fragment is identical to the amino acid sequence of the native protein. Polypeptide fragments may contain, for example: about 8, 10, 12, 14, 16, 18, 20, 22, 24, 26, 28, 30, 32, 24, 26, 28, 40, 45, 50, 55, 60, 70, 80, 90, 100, 150, 200, 240, 241, 242, 243, 244, 245, 246, 247, 248, 249, 250, 251, 252, 253, 254, 255, 256, 257, 258, 259, 260, 261, 262 contiguous amino acids, including all integers in between, of a reference polypeptide sequence, for example between 50 and 260, 50 and 255, 50 and 250, 50 and 200, 50 and 150 contiguous amino acids of a reference polypeptide sequence. The term fragment explicitly excludes full length fHbp polypeptides and mature lipoproteins thereof.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

In general, the invention does not encompass the various fHbp sequences specifically disclosed in references 2, 3, 5, 6, 7, 160, 161, 162, 163, 164, 165, 166, and 167.

SPECIFIC EMBODIMENTS OF THE INVENTION

Figure 1:
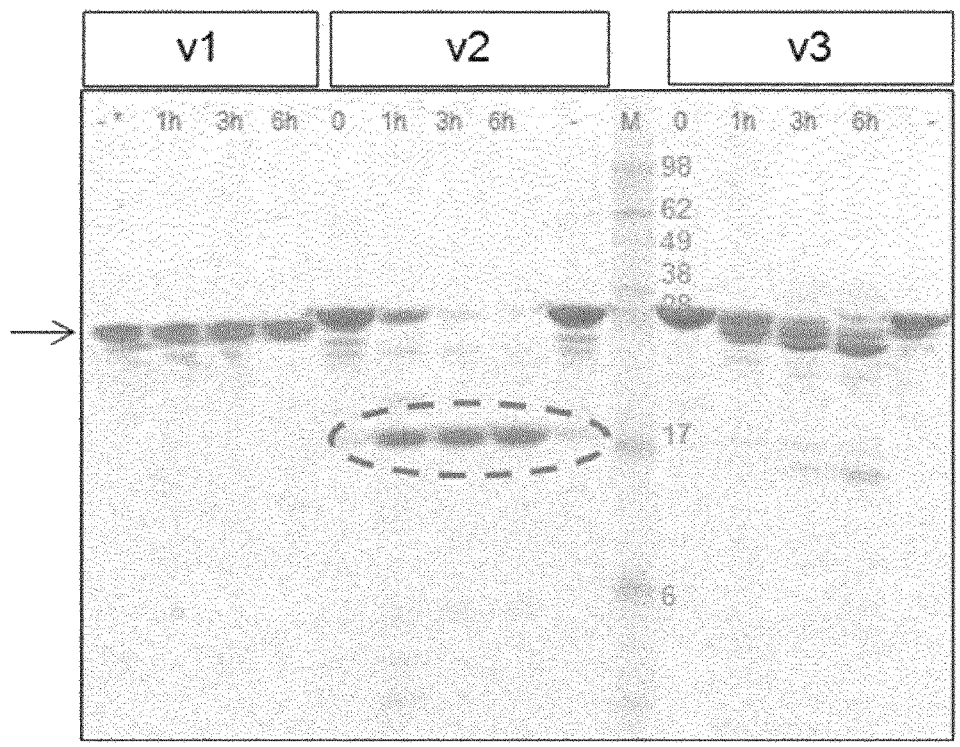
FIG. 1 shows the different sensitivity of fHbp variants to chymotrypsin cleavage. The arrow shows the position of full-length fHbp proteins.

The invention provides the following specific numbered embodiments:
1. A mutant v3 or v2 fHbp which has increased stability relative to a wild-type fHbp and, preferably, also has lower affinity for human factor H than a wild-type fHbp; for instance:
   (A) a polypeptide comprising a mutant fHbp v2 amino acid sequence, wherein: (a) the amino acid sequence has at least 80% sequence identity to SEQ ID NO: 5 and/or comprises a fragment of SEQ ID NO: 5 which is at least 7 amino acids long and contains at least one of the residues listed in (b); but (b) the amino acid sequence differs from SEQ ID NO: 5 at one or more of the following residues: 32, 33, 39, 41, 69, 100, 113, 122, 123, 124, 125, 126, 127, 128, 151, 239, and/or 240; provided that:
      if the mutant fHbp v2 amino acid sequence includes a substitution only at residue 32, either this substitution is not with alanine or at least one further residue listed in (b) is substituted;
      if the mutant fHbp v2 amino acid sequence includes a substitution only at residue 113, either this substitution is not with alanine or at least one further residue listed in (b) is substituted.
      if the mutant fHbp v2 amino acid sequence includes a substitution only at residue 122, either this substitution is not with alanine or at least one further residue listed in (b) is substituted;
      if the mutant fHbp v2 amino acid sequence includes a substitution at residue 123, either this substitution is not with alanine or at least one further residue listed in (b) is substituted;
      if the mutant fHbp v2 amino acid sequence includes a substitution only at residue 124, either this substitution is not with alanine or at least one further residue listed in (b) is substituted;

if the mutant fHbp v2 amino acid sequence includes a substitution only at residue 127, either this substitution is not with alanine or at least one further residue listed in (b) is substituted; and if the mutant fHbp v2 amino acid sequence includes a substitution only at residue 240, either this substitution is not with alanine or at least one further residue listed in (b) is substituted.

or (B) a polypeptide comprising a mutant fHbp v3 amino acid sequence, wherein: (a) the amino acid sequence has at least 80% sequence identity to SEQ ID NO: 17 and/or comprises a fragment of SEQ ID NO: 17 which is at least 7 amino acids long and contains at least one of the residues listed in (b); but (b) the amino acid sequence differs from SEQ ID NO: 17 at one or more of the following residues: 32, 33, 39, 41, 72, 103, 116, 125, 126, 127, 128, 129, 130, 131, 154, 242, and/or 243; provided that:

if the mutant fHbp v3 amino acid sequence includes a substitution at residue 32, either this substitution is not with alanine or at least one further residue listed in (b) is substituted;

if the mutant fHbp v3 amino acid sequence includes a substitution at residue 113, either this substitution is not with alanine or at least one further residue listed in (b) is substituted.

if the mutant fHbp v3 amino acid sequence includes a substitution only at residue 125, either this substitution is not with alanine or at least one further residue listed in (b) is substituted;

if the mutant fHbp v3 amino acid sequence includes a substitution at residue 126, either this substitution is not with alanine or at least one further residue listed in (b) is substituted;

if the mutant fHbp v3 amino acid sequence includes a substitution at residue 127, either this substitution is not with alanine or at least one further residue listed in (b) is substituted;

if the mutant fHbp v3 amino acid sequence includes a substitution at residue 130, either this substitution is not with alanine or at least one further residue listed in (b) is substituted; and if the mutant fHbp v3 amino acid sequence includes a substitution only at residue 243, either this substitution is not with alanine or at least one further residue listed in (b) is substituted.

2. The polypeptide of embodiment 1(B), wherein the amino acid sequence differs from SEQ ID NO: 17 by substitution at one or more of the residues listed in (b); for instance, where the substitution(s) are selected from the group consisting of: S32V; I33C; L39C; L41C; F72C; V103T; T116S; F125C; L126R; V127I; S128G or S128T; G129D; L130I; G131A; S154C; H242R; and E243H.

3. The polypeptide of embodiment 1(B) or embodiment 2, comprising more than one substitution at the residues listed in (b), and selected from groups 3A to 3O as noted above.

4. The polypeptide of embodiment 1(A), wherein the amino acid sequence differs from SEQ ID NO: 5 by substitution at one or more of the residues listed in (b); for instance, where the substitution(s) are selected from the group consisting of: S32V; V33C; L39C; L41C; F69C; V100T; I113S; F122C; L123R; V124I; S125G or S125T; G126D; L127I; G128A; S151C; H239R; and E240H.

5. The polypeptide of embodiment 1(A) or embodiment 4, comprising more than one substitution at the residues listed in (b), and selected from groups 2A to 2O as noted above.

6. The polypeptide of any of embodiments 1-5, also including one or more further mutation(s) which disrupt(s) the polypeptide's ability to bind to human factor H; for instance, in v2 including a substitution at one or more of R73, D203, E210, G228, S121, F122, L123, A192, E194, V199, I200, L201, T213, H215, F219, T231, and E240, or in v3 including a substitution at one or more of Q35, I178, L87, A88, L126, V127, V202, E213, T216, T234, V241, and E243.

7. A polypeptide comprising:
   amino acid sequence SEQ ID NO: 44, optionally with 1, 2, 3, 4, or 5 single amino acid substitutions, deletions and/or insertions, wherein the polypeptide can elicit antibodies which bind to a meningococcal fHbp polypeptide consisting of the amino acid sequence of SEQ ID NO: 40 (for example, comprising amino acid sequence SEQ ID NO: 44 with 1, 2, or 3 single amino acid substitutions), but not mutated at residue V32 or R126;
   amino acid sequence SEQ ID NO: 45, optionally with 1, 2, 3, 4, or 5 single amino acid substitutions, deletions and/or insertions, wherein the polypeptide can elicit antibodies which bind to a meningococcal fHbp polypeptide consisting of the amino acid sequence of SEQ ID NO: 2 (for example, comprising amino acid sequence SEQ ID NO: 45 with 1, 2, or 3 single amino acid substitutions), but not mutated at residue V32 or R123;
   a fHbp v3 amino acid sequence, wherein the v3 amino acid sequence is identical to a v3 wild-type amino acid sequence except for a mutation at the amino acid position corresponding to Leu-126 of SEQ ID NO: 17, provided that the mutation is not a substitution to alanine (e.g. wherein the mutation is a substitution to arginine);
   a fHbp v2 amino acid sequence, wherein the v2 amino acid sequence is identical to a v2 wild-type amino acid sequence except for a mutation at the amino acid position corresponding to Leu-123 of SEQ ID NO: 5, provided that the mutation is not a substitution to alanine (e.g. wherein the mutation is a substitution to arginine); or
   amino acid sequence SEQ ID NO: 47, optionally with 1, 2, 3, 4, or 5 single amino acid substitutions, deletions and/or insertions, wherein the polypeptide can elicit antibodies which bind to each of: a meningococcal fHbp polypeptide consisting of the amino acid sequence of SEQ ID NO: 46; a meningococcal fHbp polypeptide consisting of the amino acid sequence of SEQ ID NO: 4; and a meningococcal fHbp polypeptide consisting of the amino acid sequence of SEQ ID NO: 40 (for instance, consisting of amino acid sequence SEQ ID NO: 48).

8. A plasmid or other nucleic acid comprising a nucleotide sequence encoding the polypeptide of any of embodiment 1 to 7.

9. A host cell transformed with the plasmid of embodiment 8; e.g. wherein the cell is a meningococcal bacterium, such as a meningococcal bacterium having down-regulation or knockout of mltA and also optionally has down-regulation or knockout of: (i) at least one gene involved in rendering the lipid A portion of LPS toxic, particularly of lpxl1; and/or (ii) at least one gene involved in capsular polysaccharide synthesis or export, particularly of synX and/or ctrA.

10. Membrane vesicles prepared from the host cell of embodiment 9, wherein the vesicles include a polypeptide of any one of embodiments 1 to 7.
11. An immunogenic composition comprising a polypeptide of any one of embodiments 1 to 7, or a vesicle of embodiment 10.
12. The composition of embodiment 11, further comprising a second polypeptide that, when administered to a mammal, elicits an antibody response that is bactericidal against meningococcus.
13. The composition of embodiment 11 or 12, further comprising (i) a conjugated capsular saccharide from *N. meningitidis* serogroup A, C, W135 and/or Y and/or (ii) a conjugated capsular saccharide from *S. pneumoniae*
14. A method for raising an antibody response in a mammal, comprising administering an immunogenic composition of any of embodiments 11 to 13.

MODES FOR CARRYING OUT THE INVENTION fHbp Mutations

The v2 fHbp is recognised as being unstable. To analyse the underlying structural reasons for this undesirable property, with a view to engineering the sequence to improve stability, the inventors analysed sequence alignments and 3D structures of fHbp polypeptides. One area of particular interest was the structural interface between the N-terminal and C-terminal domains [168].

The inventors identified the mutations explained in Table 1. Three of the positions identified for mutation overlap with references 24 and 25, but the invention does not encompass the polypeptides reported in the prior art i.e. where the polypeptides include substitutions solely at these positions by alanine. For instance, E240 can be substituted with histidine to match v1, and is ideally paired with substitution at residue H239 (mutants #1 and #11). Similarly, if F122 is substituted then it is preferably paired with substitution at S151, both with cysteine to permit formation of a disulfide bridge (mutant #10). Also, if L123 is substituted then it is can be substituted with arginine (rather than alanine), or it can be paired with substitution at other residues e.g. at S32 (see mutant #3), at S125 (see mutants #20 and #22), or with substitution at residues 124-128 (see mutant #12).

Stability Studies

Unstable proteins tend to be less folded and for this reason prone to cleavage and degradation by proteases. FIG. 1 shows that v2 fHbp is more sensitive to chymotrypsin degradation than v1 and v3, and so this test can be used to assess stability of the mutant proteins.

For FIG. 1, wild-type fHbp v1, v2 and v3 were prepared at 0.5 mg/μL in 50 mM Tris-HCl, 150 mM NaCl, pH 8. Chymotrypsin was added at 1:100 (w/w) ratio. Samples were incubated at 24° C., 50 mL volume, no shaking. Samples were extracted and boiled for 0, 1, 3, or 6 hours; then run on 12% bis-Tris gel (MES buffer). The left-hand lane, marked *, indicates a sample incubated for 6 hours without protease.

Figure 2:
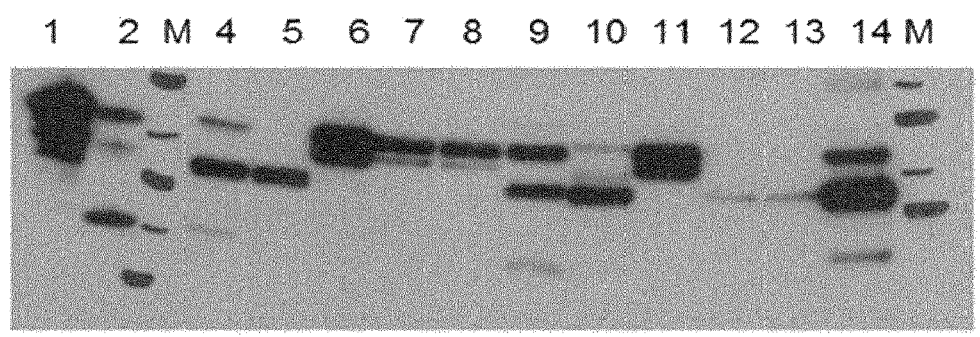
FIG. 2 shows western blot analysis of v2 mutants. Lanes are: (1 & 2) Recombinant purified v2 wild type; (4) v2 wild type lysate; (5) mutant #1; (6) mutant #2; (7) mutant #4; (8) mutant #5; (9) mutant #7; (10) mutant #8; (11) mutant #12; (12) mutant #14 (13) mutant #15; (14) fHbp var2 NAG-trx control i.e. v2 protein where N-terminal sequence GPDSDRLQQRR (SEQ ID NO: 37) is replaced by GSKDISS (SEQ ID NO: 38). Lanes 2-14 included chymotrypsin. M is molecular markers.
Figure 3:
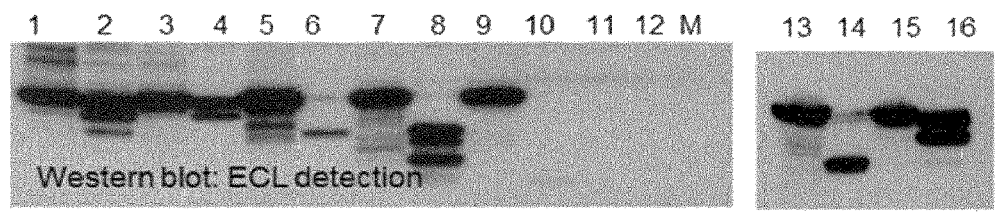
FIG. 3 shows further western blot analysis of v2 mutants. Lanes are: (1&2) mutant #3; (3&4) mutant #6; (5&6) mutant #9; (7&8) mutant #10; (9&10) mutant #13; (11&12) Δgono; (13&14) v2 wildtype; (15&16) mutant #22. Odd-numbered lanes are for proteins which were incubated without chymotrypsin, whereas even-numbered lanes were for proteins incubated with chymotrypsin. The 'Δgono' protein is a recombinant v2 where the N-terminal sequence (SEQ ID NO: 37) has been removed.
Figure 4:
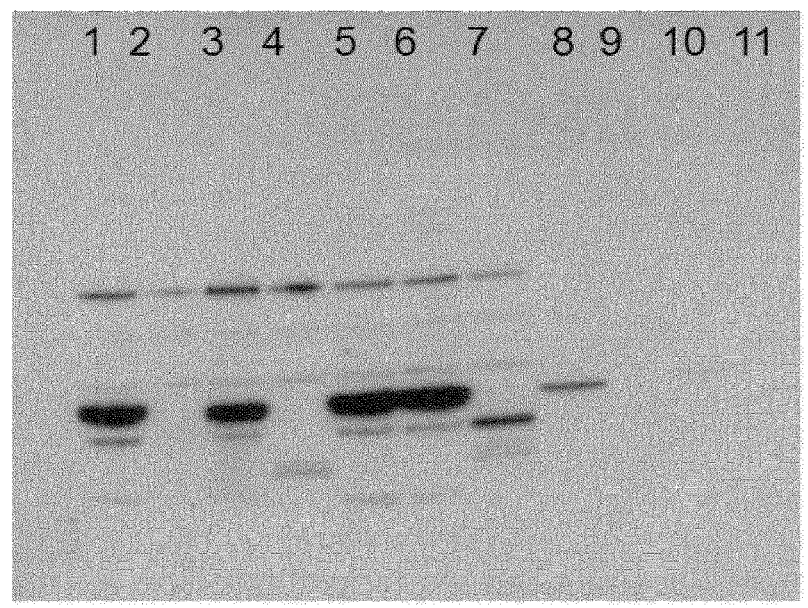
FIG. 4 shows further western blot analysis of v2 mutants. Lanes are: (1&2) mutant #11; (3&4) N-trx; (5-7) mutant #19; (8&9) mutant #20; (10&11) mutant #21. Lanes 2, 4, 7, 9 and 11 proteins which were incubated with chymotrypsin, whereas the other lanes had no chymotrypsin. The 'N-trx' protein is a recombinant v2 where the N-terminal sequence (SEQ ID NO: 37) is replaced by SEQ ID NO: 39.

Cell lysates of *E. coli* expressing the recombinant proteins have been incubated with 1:100 w/w ratio chymotrypsin for 3 hours at 25° C. The degradation pattern has been analysed by Western blotting following the incubation with an immune polyclonal serum elicited in rabbit against all three fHbp variants. The presence of cleavage products at lower apparent molecular weight (FIGS. 2-4) is interpreted as an indication of instability, whereas persistence of a band corresponding to an apparent MW of ~30 kDa is interpreted as an indication of increased stability. Mutants #1-6, #12 and #22 all showed increased resistance to chymotrypsin cleavage compared to the wild type v2.

DSC has been used as an independent approach to assess the effects of mutations on the stability of purified recombinant fHbp v2 proteins. $T_m$ (melting temperature) measured by DSC corresponds to the temperature at which the analysed protein is 50% in the folded state and 50% in the unfolded state. Changes which stabilize the conformation of a protein will increase Tm, whereas destabilizing changes will decrease Tm. As seen in FIG. 3D of ref. 24, the DSC profile of wild-type v2 fHbp shows two Tm values: $T_{m1}$ at ~40° C., which corresponds to the melting temperature of the N-terminal domain, and $T_{m2}$ at ~80° C. corresponding to the melting temperature of the C-terminal domain. Values of $T_{m1}$ and $T_{m2}$ for analyzed mutants are shown in Table 1. Mutants #2, #4, #5, #12, #19 and #21 showed increased $T_m$ of the N-terminal domain relative to the wild-type protein, and this effect was more marked for mutants #2, #4 and #12.

Size-exclusion chromatography (SEC) was used to assess the percentage of monomeric protein, and results are also shown in Table 1.

Mutants #2, #3, and #4

Figure 5:
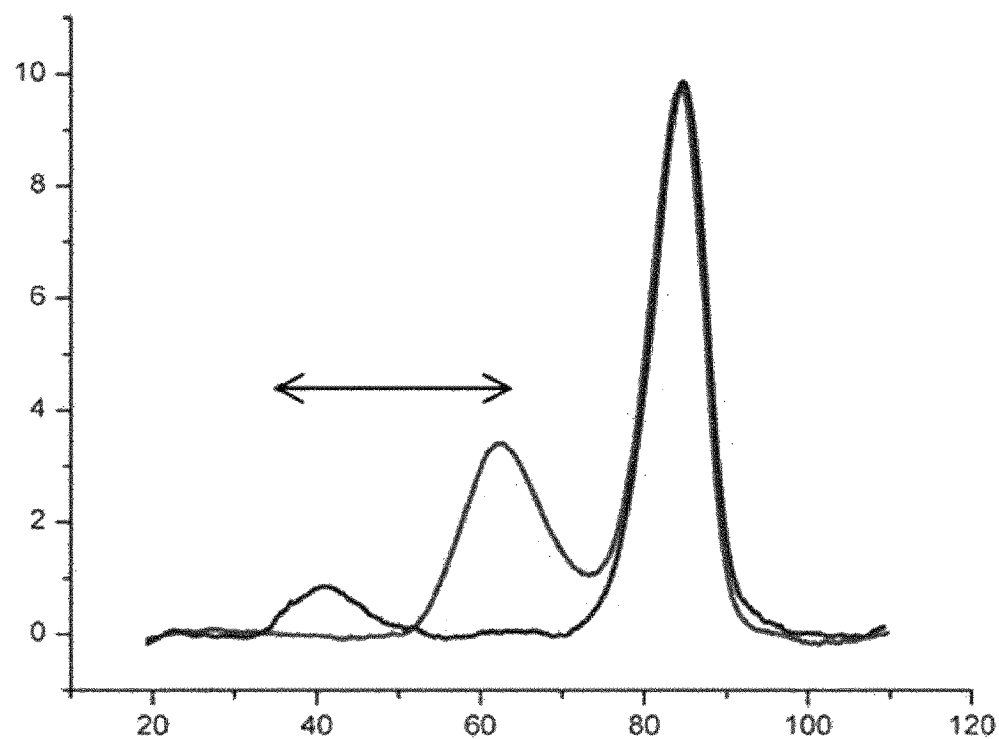
FIG. 5 shows DSC results for wild-type and S58V/L149R mutant v2 fHbp. The C-terminal domain was unaffected by the mutation, but the Tm of the N-terminal domain was increased by >20° C. (marked with the arrow). The y-axis shows Cp (kcal/mol/° C.), and the x-axis show temperature (° C.).

Mutant #3 (group 2B) gave the best overall results in the v2 stability studies. This protein (SEQ ID NO: 20) includes mutations at Ser-58 (S32 in SEQ ID NO: 5) and Leu-149 (L123 in SEQ ID NO: 5), with substitutions by Val and Arg, respectively. The mutant v2 protein (SEQ ID NO: 20, comprising SEQ ID NO: 45) was analysed by DSC and, compared to the wild-type sequence, the $T_m$ of its N-terminus domain is >20° C. higher (FIG. 5).

In a serum bactericidal assay this v2 mutant could compete for binding to human antibodies which had been raised using a wild-type v2 sequence.

Figure 6:
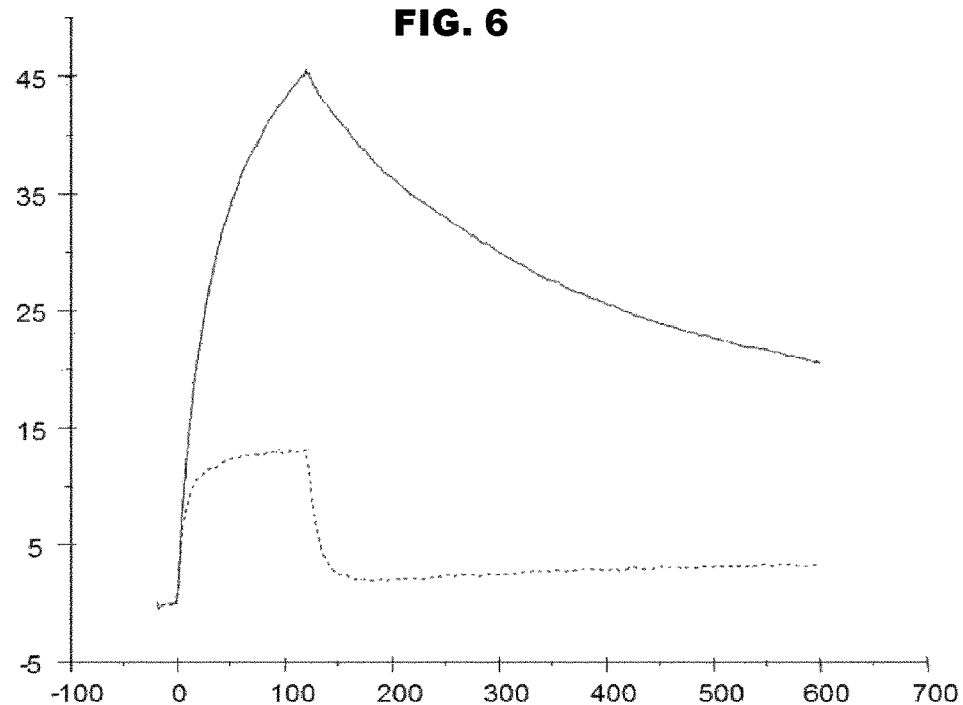
FIG. 6 shows the SPR response of wild-type (solid) and mutant (dashed) v2 fHbp.

Although the S58V and L149R mutations had been introduced to improve stability, and did indeed achieve this goal, FIG. 6 shows that the mutant v2 polypeptide (dotted line) surprisingly showed much reduced binding to fH compared to the wild-type v2 sequence (solid line) when measured by surface plasmon resonance against immobilised fH. The S58V mutation on its own had little impact on fH binding, and the S58V/L149R double mutant showed higher fH binding than fHbp carrying only the L149R mutant.

When mutant #3 was further combined with the 'E313A' mutation in v2 there was a complete loss of fH binding as assessed by SPR.

The equivalent mutations were introduced into a v3 sequence (SEQ ID NO: 17), to give v3 mutant SEQ ID NO: 44. The effects of the individual S58V and L149R mutations on fH binding were studied in v3 (i.e. the v3 equivalents of v2 mutants #2 and #4). Thus, numbered according to SEQ ID NO: 17, mutation S32V or L126R was introduced into the v3 sequence. These two mutants were compared to two different wild-type v3 sequences, and also to the 'E313A' mutant which is known to disrupt fH binding in v3 [23].

Figure 7:
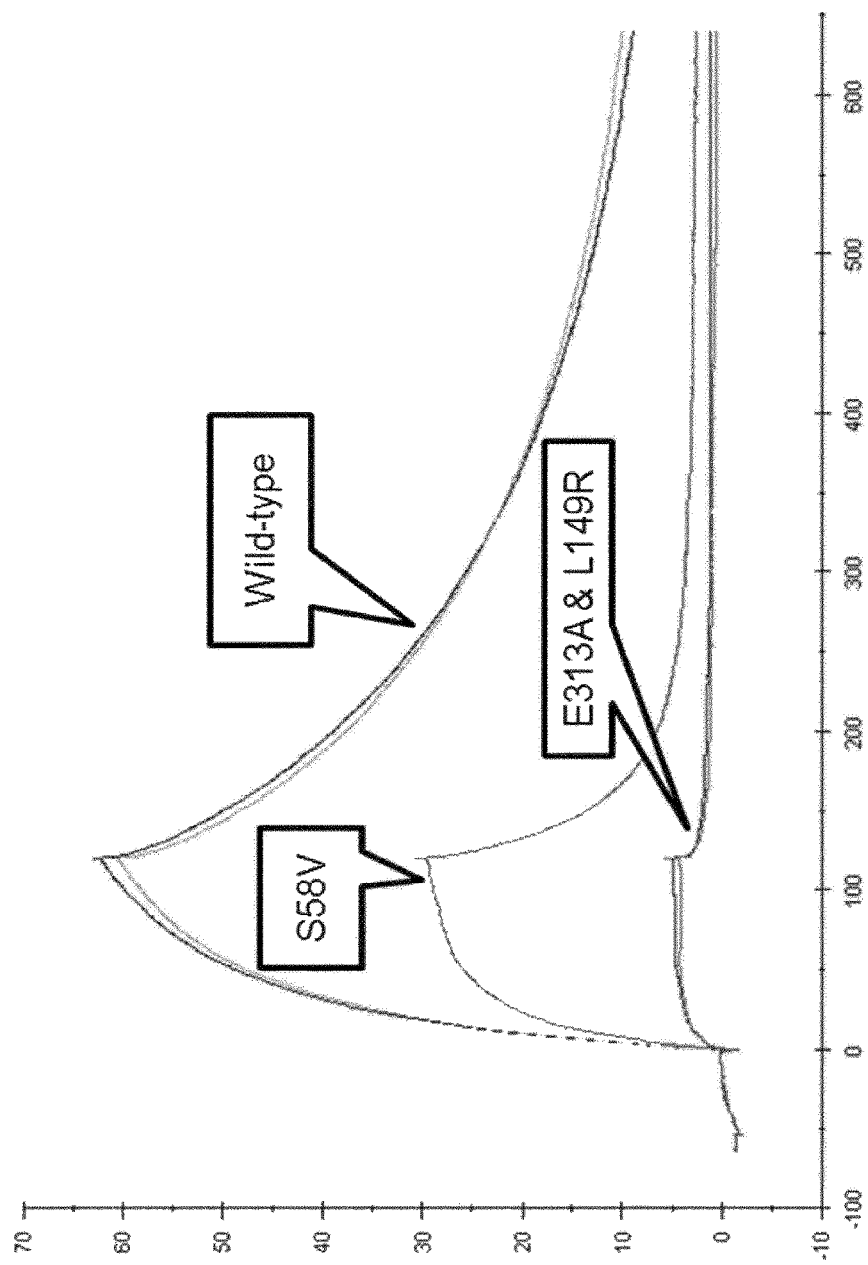
FIG. 7 shows the SPR response of v3 fHbp, either as wild-type (top) or with various mutations.

As shown in FIG. 7, wild-type v3 binds fH (top two lines). The S58V mutation, which was designed to improve stability, reduced the SPR peak value by about 2-fold. Most surprisingly, the L149R mutation (again, designed to improve stability) reduced fH affinity to a similar level to the known E313A mutant (bottom two lines).

The S58V and L149R mutations in v3 were also studied by DSC, and were found to increase the N-terminal $T_m$ by 5.5° C. (S58V) or by 6.7° C. (L149R) relative to wild-type.

The $T_m$ of both mutants was higher than seen in the v2 double mutant (63.5° C.—see Table 1). The L149R v3 mutant also showed a higher $T_m$ value for its C-terminal domain, whereas there was almost no shift here for the S58V v3 mutant. SPR showed that fH binding by mutant #2 was reduced by about a half, but for mutant #4 fH affinity was reduced to a similar level to the known E313A mutant (as also seen with v2). When the two mutations were combined (i.e. mutant #3) the $T_m$ increase compared to wild-type was 11.2° C. When the 'E313A' mutation was added to mutant #3 fH binding was almost completely eliminated, although the $T_m$ of the N-terminal domain also decreased by 2.9° C. when compared to mutant #3 (while remaining 8.3° C. higher than v3 wild-type). The 'E313A' mutation alone was much less stable than wild-type, showing a $T_m$ decrease of 6.3° C.

Thus mutations #2 and #4 can be used alone, or in combination (i.e. mutant #3), optionally with further mutations, to stabilise v2 or v3 fHbp but also to disrupt fH affinity.

A serum bactericidal assay was used for assessing the immunogenic efficacy of mutants #3 and #4 in v2 and v3. In addition, the 'E313A' mutant was also tested in v2 and v3, either alone or in combination with the #3 mutations. Wild-type v2 and v3 fHbp were also tested for comparison. The proteins were administered at 20 µg/dose with an aluminium hydroxide adjuvant and the resulting sera were tested for bactericidal activity against a panel of seven strains (four v2 strains, three v3 strains) including strains which express the same fHbp as the starting wild-type fHbp sequences (i.e. v2 sequence 2.16 and v3 sequence 3.42).

Results for the v2 proteins were as follows (SEQ ID is for the AG form; *=homologous fHbp):

| Protein | SEQ ID | SBA against v2 strains | | | | SBA against v3 strains | | |
|---|---|---|---|---|---|---|---|---|
| | | v2.16* | v2.19 | v2.21 | v2.24 | v3.42* | v3.28 | v3.30 |
| w.t. | 5 | 32768 | 32 | 32 | 1024 | >32768 | <16 | 32 |
| #4 | 21 | 32768 | <16 | <16 | 128 | 1024 | <16 | 16 |
| #3 | 45 | 4096 | 32 | <16 | <16 | >32768 | 128 | <16 |
| #3 + E313A | 57 | 4096 | 16 | <16 | <16 | >32768 | <16 | <16 |
| E313A | 56 | 128 | 16 | <16 | <16 | 4096 | <16 | <16 |

Results for the v3 proteins were as follows:

| Protein | SEQ ID | SBA against v3 strains | | | SBA against v2 strains | | | |
|---|---|---|---|---|---|---|---|---|
| | | v3.42* | v3.28 | v3.30 | v2.16* | v2.19 | v2.21 | v2.24 |
| w.t. | 17 | >32768 | 512 | 1024 | 1024 | 32 | 64 | 256 |
| #4 | 53 | 1024 | <16 | 16 | <16 | 16 | <16 | 128 |
| #3 | 44 | 4096 | 32 | 16 | 4096 | <16 | 16 | 16 |
| #3 + E313A | 43 | 256 | <16 | 16 | 64 | <16 | <16 | 16 |
| E313A | 41 | 4096 | 32 | 256 | 8192 | 32 | 32 | 128 |

Combination of Mutants #2 and #12

Mutants #2 and #12 each showed improvements in v2 stability, so these two mutants were combined into a single fHbp (SEQ ID NO: 58, AG form). Compared to mutant #12 the N-terminal $T_m$ of this combined mutant increased by a further 4.2° C., giving the highest $T_m$ of any of the tested mutant v2 proteins. Furthermore, it showed a strongly reduced fH binding (SPR peak value reduced about 8×).

Mutant Fusion Protein

Mutant v2 and v3 sequences were fused via a GSGGGG linker (SEQ ID NO: 50), also with a mutant v1 sequence, to give SEQ ID NO: 48. This sequence includes the S58V and L149R mutations for both v2 and v3, and the R41S mutation [21] for v1. SEQ ID NO: 47 includes, from N-terminus to C-terminus: v2 mutant #3 (SEQ ID NO: 45); v3 mutant #3 (SEQ ID NO: 44); and v1 'R41S' mutant (SEQ ID NO: 49), connected by the glycine-rich linker sequence, SEQ ID NO: 50. The fusion protein can conveniently be expressed by adding a N-terminus sequence of Met-[SEQ ID NO: 37]-, thus providing a mature protein SEQ ID NO: 48.

This fusion protein thus takes advantage of the observation that mutant #3 provides for both v2 and v3 a large increase in stability ($T_m$) and a large decrease in fH affinity. For v1 the R41S mutation has little effect on thermal stability but strongly reduces fH binding.

Figure 8:
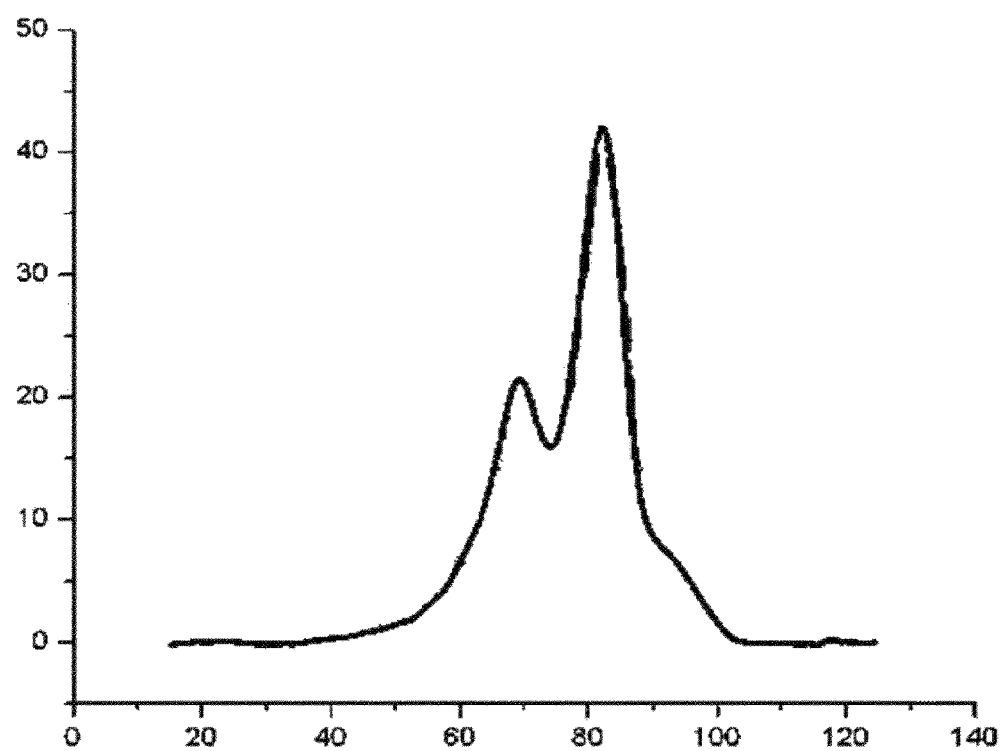
FIG. 8 shows DSC results for the triple fusion protein of SEQ ID NO: 48. The axes are as in FIG. 5.

DSC studies of the triple fusion protein (FIG. 8) show that the three N-terminal transitions fall together in a broad peak centred at 68° C. The three C-termini transitions also fall together. UPLC showed that the protein was 94.9% pure, and HPLC analysis showed <1.5% oligomers.

Mutant Proteins Expressed in 'GMMA' Membrane Vesicles

A v1 meningococcal strain was prepared with knockouts of mltA, lpxL1 and synX to provide a genetic background for hyper-expressing v2 and v3 fHbp lipoproteins under the control of the 'ST2' promoter [157] in a 'GMMA' vaccine. The v2 genes were integrated into the genome at the deleted lpxL1 locus whereas the v3 genes were integrated at the synX locus. In addition, the native v1 fHbp gene was deleted so that v2 and v3 could be studied without interference.

Mutants #3 and #4 were tested for v2, and mutant #4 was tested for v3. In addition, a strain with both of the v2 and v3 #4 mutants was prepared. For these bacteria fHbp expression and fH binding were assessed by FACS.

For strains expressing only v2 fHbp FACS showed that the various proteins were expressed at similar levels, at levels 2 logs higher than the background Δfhbp strain. In terms of fH binding, however, mutants #3 and #4 showed much less binding, with binding in mutant #4 being only slightly above background. These results mirror the SPR data obtained with recombinant v2 proteins.

For the strain expressing v3 mutant #4 FACS showed full expression of fHbp, but its fH binding was abolished (matching the fH binding seen with the 'H222R' mutation [19,25]).

For the strain expressing mutant #4 from v2 and v3, both fHbp proteins could be detected by FACS but fH binding was only slightly above that seen in the background Δfhbp strain.

Western blot analysis was used to test the stability of fHbp expression in these bacteria when growing in liquid culture for 6 days. Expression of mutant v2 proteins remained stable over time, even when v3 was co-expressed. Expression of mutant v3 proteins also remained stable, except in the strain expressing both the v2 and v3 mutant, where v3 expression declined over time.

It will be understood that the invention is described above by way of example only and modifications may be made whilst remaining within the scope and spirit of the invention.

SEQUENCE LISTING

>[MC58, v1]

SEQ ID NO: 1

MNRTAFCCLSLTTALILTACSSGGGGVAADIGAGLADALTAPLDHKDKGLQSLTLDQSVRKNEKLKLAAQGAEKT

YGNGDSLNTGKLKNDKVSRFDFIRQIEVDGQLITLESGEFQVYKQSHSALTAFQTEQIQDSEHSGKMVAKRQFRI

-continued

GDIAGEHTSFDKLPEGGRATYRGTAFGSDDAGGKLTYTIDFAAKQGNGKIEHLKSPELNVDLAAADIKPDGKRHA
VISGSVLYNQAEKGSYSLGIFGGKAQEVAGSAEVKTVNGIRHIGLAAKQ

>[2996, v2]  SEQ ID NO: 2
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQIAGSATVKIGEKVHEIGIAGKQ

>[M1239, v3]  SEQ ID NO: 3
MNRTAFCCLSLTTALILTACSSGGGGSGGGGVAADIGTGLADALTAPLDHKDKGLKSLTLEDSIPQNGTLTLSAQ
GAEKTFKAGDKDNSLNTGKLKNDKISRFDFVQKIEVDGQTITLASGEFQIYKQNHSAVVALQIEKINNPDKTDSL
INQRSFLVSGLGGEHTAFNQLPGGKAEYHGKAFSSDDPNGRLHYSIDFTKKQGYGRIEHLKTLEQNVELAAAELK
ADEKSHAVILGDTRYGSEEKGTYHLALFGDRAQEIAGSATVKIGEKVHEIGIAGKQ

>[2996 mature]  SEQ ID NO: 4
CSSGGGGVAADIGAGLADALTAPLDHKDKSLQSLTLDQSVRKNEKLKLAAQGAEKTYGNGDSLNTGKLKNDKVSR
FDFIRQIEVDGQLITLESGEFQIYKQDHSAVVALQIEKINNPDKIDSLINQRSFLVSGLGGEHTAFNQLPDGKAE
YHGKAFSSDDAGGKLTYTIDFAAKQGHGKIEHLKTPEQNVELAAAELKADEKSHAVILGDTRYGSEEKGTYHLAL
FGDRAQEIAGSATVKIGEKVHEIGIAGKQ >[2996 ΔG]  SEQ ID NO: 5
VAADIGAGLADALTAPLDHKDKSLQSLTLDQSVRKNEKLKLAAQGAEKTYGNGDSLNTGKLKNDKVSRFDFIRQI
EVDGQLITLESGEFQIYKQDHSAVVALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHEIGIAGKQ >[NHBA]  SEQ ID NO: 6
MFKRSVIAMACIFALSACGGGGGGSPDVKSADTLSKPAAPVVSEKETEAKEDAPQAGSGQGAPSAQGSQDMAAV
SEENTGNGGAVTADNPKNEDEVAQNDMPQNAAGTDSSTPNHTPDPNMLAGNMENQATDAGESSQPANQPDMANAA
DGMQGDDPSAGGQNAGNTAAQGANQAGNNQAAGSSDPIPASNPAPANGGSNFGRVDLANGVLIDGPSQNITLTHC
KGDSCSGNNFLDEEVQLKSEFEKLSDADKISNYKKDGKNDKFVGLVADSVQMKGINQYIIFYKPKPTSFARFRRS
ARSRRSLPAEMPLIPVNQADTLIVDGEAVSLTGHSGNIFAPEGNYRYLTYGAEKLPGGSYALRVQGEPAKGEMLA
GAAVYNGEVLHFHTENGRPYPTRGRFAAKVDFGSKSVDGIIDSGDDLHMGTQKFKAAIDGNGFKGTWTENGSGDV
SGKFYGPAGEEVAGKYSYRPTDAEKGGFGVFAGKKEQD >[NadA]  SEQ ID NO: 7
MSMKHFPSKVLTTAILATFCSGALAATSDDDVKKAATVAIVAAYNNGQEINGFKAGETIYDIGEDGTITQKDATA
ADVEADDFKGLGLKKVVTNLTKTVNENKQNVDAKVKAAESEIEKLTTKLADTDAALADTDAALDETTNALNKLGE
NITTFAEETKTNIVKIDEKLEAVADTVDKHAEAFNDIADSLDETNTKADEAVKTANEAKQTAEETKQNVDAKVKA
AETAAGKAEAAAGTANTAADKAEAVAAKVTDIKADIATNKADIAKNSARIDSLDKNVANLRKETRQGLAEQAALS
GLFQPYNVGRFNVTAAVGGYKSESAVAIGTGFRFTENFAAKAGVAVGTSSGSSAAYHVGVNYEW >[NspA]  SEQ ID NO: 8
MKKALATLIALALPAAALAEGASGFYVQADAAHAKASSSLGSAKGFSPRISAGYRINDLRFAVDYTRYKNYKAPS
TDFKLYSIGASAIYDFDTQSPVKPYLGARLSLNRASVDLGGSDSFSQTSIGLGVLTGVSYAVTPNVDLDAGYRYN
YIGKVNTVKNVRSGELSAGVRVKF >[HmbR]
SEQ ID NO: 9

MKPLQMLPIAALVGSIFGNPVLAADEAATETTPVKAEIKAVRVKGQRNAPAAVERVNLNRIKQEMIRDNKDLVRY

STDVGLSDSGRHQKGFAVRGVEGNRVGVSIDGVNLPDSEENSLYARYGNFNSSRLSIDPELVRNIEIVKGADSFN

TGSGALGGGVNYQTLQGRDLLLDDRQFGVMMKNGYSTRNREWTNTLGFGVSNDRVDAALLYSQRRGHETESAGNR

GYAVEGEGSGANIRGSARGIPDSSKHKYNHHALGKIAYQINDNHRIGASLNGQQGHNYTVEESYNLTASSWREAD

DVNRRRNANLFYEWMPDSNWLSSLKADFDYQKTKVAAVNNKGSFPMDYSTWTRNYNQKDLDEIYNRSMDTRFKRF

TLRLDSHPLQLGGGRHRLSFKTFVSRRDFENLNRDDYYFSGRVVRTTSSIQHPVKTTNYGFSLSDQIQWNDVFSS

RAGIRYDHTKMTPQELNAECHACDKTPPAANTYKGWSGFVGLAAQLNQAWRVGYDITSGYRVPNASEVYFTYNHG

SGNWLPNPNLKAERSTTHTLSLQGRSEKGMLDANLYQSNYRNFLSEEQKLTTSGTPGCTEENAYYGICSDPYKEK

LDWQMKNIDKARIRGIELTGRLNVDKVASFVPEGWKLFGSLGYAKSKLSGDNSLLSTQPLKVIAGIDYESPSEKW

GVFSRLTYLGAKKVKDAQYTVYENKGWGTPLQKKVKDYPWLNKSAYVFDMYGFYKPAKNLTLRAGVYNLFNRKYT

TWDSLRGLYSYSTTNAVDRDGKGLDRYRAPGRNYAVSLEWKF

>[NhhA]
SEQ ID NO: 10

MNKIYRIIWNSALNAWVVVSELTRNHTKRASATVKTAVLATLLFATVQASANNEEQEEDLYLDPVQRTVAVLIVN

SDKEGTGEKEKVEENSDWAVYFNEKGVLTAREITLKAGDNLKIKQNGTNFTYSLKKDLTDLTSVGTEKLSFSANG

NKVNITSDTKGLNFAKETAGTNGDTTVHLNGIGSTLTDTLLNTGATTNVTNDNVTDDEKKRAASVKDVLNAGWNI

KGVKPGTTASDNVDFVRTYDTVEFLSADTKTTTVNVESKDNGKKTEVKIGAKTSVIKEKDGKLVTGKDKGENGSS

TDEGEGLVTAKEVIDAVNKAGWRMKTTTANGQTGQADKFETVTSGTNVTFASGKGTTATVSKDDQGNITVMYDVN

VGDALNVNQLQNSGWNLDSKAVAGSSGKVISGNVSPSKGKMDETVNINAGNNIEITRNGKNIDIATSMTPQFSSV

SLGAGADAPTLSVDGDALNVGSKKDNKPVRITNVAPGVKEGDVTNVAQLKGVAQNLNNRIDNVDGNARAGIAQAI

ATAGLVQAYLPGKSMMAIGGGTYRGEAGYAIGYSSISDGGNWIIKGTASGNSRGHFGASASVGYQW

>[App]
SEQ ID NO: 11

MKTTDKRTTETHRKAPKTGRIRFSPAYLAICLSEGILPQAWAGHTYFGINYQYYRDFAENKGKFAVGAKDIEVYN

KKGELVGKSMTKAPMIDFSVVSRNGVAALVGDQYIVSVAHNGGYNNVDFGAEGRNPDQHRFTYKIVKRNNYKAGT

KGHPYGGDYHMPRLHKFVTDAEPVEMTSYMDGRKYIDQNNYPDRVRIGAGRQYWRSDEDEPNNRESSYHIASAYS

WLVGGNTFAQNGSGGGTVNLGSEKIKHSPYGFLPTGGSFGDSGSPMFIYDAQKQKWLINGVLQTGNPYIGKSNGF

QLVRKDWFYDEIFAGDTHSVFYEPRQNGKYSFNDDNNGTGKINAKHEHNSLPNRLKTRTVQLFNVSLSETAREPV

YHAAGGVNSYRPRLNNGENISFIDEGKGELILTSNINQGAGGLYFQGDFTVSPENNETWQGAGVHISEDSTVTWK

VNGVANDRLSKIGKGTLHVQAKGENQGSISVGDGTVILDQQADDKGKKQAFSEIGLVSGRGTVQLNADNQFNPDK

LYFGERGGRLDLNGHSLSEHRIQNTDEGAMIVNHNQDKESTVTITGNKDIATTGNNNSLDSKKETAYNGWEGEKD

TTKTNGRLNLVYQPAAEDRTLLLSGGTNLNGNITQTNGKLFFSGRPTPHAYNHLNDHWSQKEGIPRGEIVWDNDW

INRTFKAENFQIKGGQAVVSRNVAKVKGDWHLSNHAQAVFGVAPHQSHTICTRSDWTGLTNCVEKTITDDKVIAS

LTKTDISGNVDLADHAHLNLTGLATLNGNLSANGDTRYTVSHNATQNGNLSLVGNAQATFNQATLNGNTSASGNA

SFNLSDHAVQNGSLTLSGNAKANVSHSALNGNVSLADKAVFHFESSRFTGQISGGKDTALHLKDSEWTLPSGTEL

GNLNLDNATITLNSAYRHDAAGAQTGSATDAPRRRSRRSRRSLLSVTPPTSVESRENTLTVNGKLNGQGTFREMS

ELFGYRSDKLKLAESSEGTYTLAVNNTGNEPASLEQLTVVEGKDNKPLSENLNFTLQNEHVDAGAWRYQLIRKDG

EFRLHNPVKEQELSDKLGKAEAKKQAEKDNAQSLDALIAAGRDAVEKTESVAEPARQAGGENVGIMQAEEEKKRV

QADKDTALAKQREAETRPATTAFPRARRARRDLPQLQPQPQPQPQRDLISRYANSGLSEFSATLNSVFAVQDELD

RVFAEDRRNAVWTSGIRDTKHYRSQDFRAYRQQTDLRQIGMQKNLGSGRVGILFSHNRTENTFDDGIGNSARLAH

-continued

```
GAVFGQYGIDRFYIGISAGAGFSSGSLSDGIGGKIRRRVLHYGIQARYRAGEGGEGIEPHIGATRYFVQKADYRY

ENVNIATPGLAFNRYRAGIKADYSFKPAQHISITPYLSLSYTDAASGKVRTRVNTAVLAQDFGKTRSAEWGVNAE

IKGFTLSLHAAAAKGPQLEAQHSAGIKLGYRW
```

>[Omp85]

SEQ ID NO: 12

```
MKLKQIASALMMLGISPLALADFTIQDIRVEGLQRTEPSTVFNYLPVKVGDTYNDTHGSAIIKSLYATGEFDDVR

VETADGQLLLTVIERPTIGSLNITGAKMLQNDAIKKNLESFGLAQSQYFNQATLNQAVAGLKEEYLGRGKLNIQI

TPKVTKLARNRVDIDITIDEGKSAKITDIEFEGNQVYSDRKLMRQMSLTEGGIWTWLTRSNQFNEQKFAQDMEKV

TDFYQNNGYFDFRILDTDIQTNEDKTKQTIKITVHEGGRFRWGKVSIEGDTNEVPKAELEKLLTMKPGKWYERQQ

MTAVLGEIQNRMGSAGYAYSEISVQPLPNAETKTVDFVLHIEPGRKIYVNEIHITGNNKTRDEVVRRELRQMESA

PYDTSKLQRSKERVELLGYFDNVQFDAVPLAGTPDKVDLNMSLTERSTGSLDLSAGWVQDTGLVMSAGVSQDNLF

GTGKSAALRASRSKTTLNGSLSFTDPYFTADGVSLGYDVYGKAFDPRKASTSIKQYKTTTAGAGIRMSVPVTEYD

RVNEGLVAEHLTVNTYNKAPKHYADFIKKYGKTDGTDGSFKGWLYKGTVGWGRNKTDSALWPTRGYLTGVNAEIA

LPGSKLQYYSATHNQTWFFPLSKTFTLMLGGEVGIAGGYGRTKEIPFFENFYGGGLGSVRGYESGTLGPKVYDEY

GEKISYGGNKKANVSAELLFPMPGAKDARTVRLSLFADAGSVWDGKTYDDNSSSATGGRVQNIYGAGNTHKSTFT

NELRYSAGGAVTWLSPLGPMKFSYAYPLKKKPEDEIQRFQFQLGTTF
```

>[NMB2091]

SEQ ID NO: 13

```
MVSAVIGSAAVGAKSAVDRRTTGAQTDDNVMALRIETTARSYLRQNNQTKGYTPQISVVGYDRHLLLLGQVATEG

EKQFVGQIARSEQAAEGVYNYITVASLPRTAGDIAGDTWNTSKVRATLLGISPATRARVKIVTYGNVTYVMGILT

PEEQAQITQKVSTTVGVQKVITLYQNYVQR
```

>[NHBA fusion]

SEQ ID NO: 14

```
MASPDVKSADTLSKPAAPVVSEKETEAKEDAPQAGSQGQGAPSAQGGQDMAAVSEENTGNGGAAATDKPKNEDEG

AQNDMPQNAADTDSLTPNHTPASNMPAGNMENQAPDAGESEQPANQPDMANTADGMQGDDPSAGGENAGNTAAQG

TNQAENNQTAGSQNPASSTNPSATNSGGDFGRTNVGNSVVIDGPSQNITLTHCKGDSCSGNNFLDEEVQLKSEFE

KLSDADKISNYKKDGKNDGKNDKFVGLVADSVQMKGINQYIIFYKPKPTSFARFRRSARSRRSLPAEMPLIPVNQ

ADTLIVDGEAVSLTGHSGNIFAPEGNYRYLTYGAEKLPGGSYALRVQGEPSKGEMLAGTAVYNGEVLHFHTENGR

PSPSRGRFAAKVDFGSKSVDGIIDSGDGLHMGTQKFKAAIDGNGFKGTWTENGGGDVSGKFYGPAGEEVAGKYSY

RPTDAEKGGFGVFAGKKEQDGSGGGATYKVDEYHANARFAIDHFNTSTNVGGFYGLTGSVEFDQAKRDGKIDIT

IPVANLQSGSQHFTDHLKSADIFDAAQYPDIRFVSTKENENGKKLVSVDGNLTMHGKTAPVKLKAEKENCYQSPM

AKTEVCGGDFSTTIDRTKWGVDYLVNVGMTKSVRIDIQIEAAKQ
```

>[NadA fragment]

SEQ ID NO: 15

```
ATNDDDVKKAATVAIAAAYNNGQEINGFKAGETIYDIDEDGTITKKDATAADVEADDFKGLGLKKVVTNLTKTVN

ENKQNVDAKVKAAESEIEKLTTKLADTDAALADTDAALDATTNALNKLGENITTFAEETKTNIVKIDEKLEAVAD

TVDKHAEAFNDTADSLDETNTKADEAVKTANEAKQTAEETKQNVDAKVKAAETAAGKAEAAAGTANTAADKAEAV

AAKVTDIKADIATNKDNTAKKANSADVYTREESDSKEVRIDGLNATTEKLDTRLASAEKSIADHDTRLNGLDKTV

SDLRKETRQGLAEQAALSGLFQPYNVG
```

>[MC58, ΔG]

SEQ ID NO: 16

```
VAADIGAGLADALTAPLDHKDKGLQSLTLDQSVRKNEKLKLAAQGAEKTYGNGDSLNTGKLKNDKVSRFDFIRQI

EVDGQLITLESGEFQVYKQSHSALTAFQTEQIQDSEHSGKMVAKRQFRIGDIAGEHTSFDKLPEGGRATYRGTAF

GSDDAGGKLTYTIDFAAKQGNGKIEHLKSPELNVDLAAADIKPDGKRHAVISGSVLYNQAEKGSYSLGIFGGKAQ

EVAGSAEVKTVNGIRHIGLAAKQ
```

```
>[M1239, ΔG]
                                                              SEQ ID NO: 17
VAADIGTGLADALTAPLDHKDKGLKSLTLEDSIPQNGTLTLSAQGAEKTFKAGDKDNSLNTGKLKNDKISRFDFV

QKIEVDGQTITLASGEFQIYKQNHSAVVALQIEKINNPDKTDSLINQRSFLVSGLGGEHTAFNQLPGGKAEYHGK

AFSSDDPNGRLHYSIDFTKKQGYGRIEHLKTLEQNVELAAAELKADEKSHAVILGDTRYGSEEKGTYHLALFGDR

AQEIAGSATVKIGEKVHEIGIAGKQ

>[MUTANT #1]
                                                              SEQ ID NO: 18
MNRTAFCCLSLTAALILTACSSGGGGVAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSAVVALQIEKINNPDKIDSLINQRSFLV

SGLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVRHIGIAGKQ

>[MUTANT #2]
                                                              SEQ ID NO: 19
MNRTAFCCLSLTAALILTACSSGGGGVAADIGAGLADALTAPLDHKDKSLQSLTLDQVVRKNEKLKLAAQGAEKT

YGNGDSLNTGKLKNDKVSRFDFIRQIEVDGQLITLESGEFQIYKQDHSAVVALQIEKINNPDKIDSLINQRSFLV

SGLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVRHIGIAGKQ

>[MUTANT #3]
                                                              SEQ ID NO: 20
MNRTAFCCLSLTAALILTACSSGGGGVAADIGAGLADALTAPLDHKDKSLQSLTLDQVVRKNEKLKLAAQGAEKT

YGNGDSLNTGKLKNDKVSRFDFIRQIEVDGQLITLESGEFQIYKQDHSAVVALQIEKINNPDKIDSLINQRSFRV

SGLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVHEIGIAGKQ

>[MUTANT #4]
                                                              SEQ ID NO: 21
MNRTAFCCLSLTAALILTACSSGGGGVAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSAVVALQIEKINNPDKIDSLINQRSFRV

SGLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVHEIGIAGKQ

>[MUTANT #5]
                                                              SEQ ID NO: 22
MNRTAFCCLSLTAALILTACSSGGGGVAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSAVVALQIEKINNPDKIDSLINQRSFLV

GDLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVHEIGIAGKQ

>[MUTANT #6]
                                                              SEQ ID NO: 23
MNRTAFCCLSLTAALILTACSSGGGGVAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSAVTALQIEKINNPDKIDSLINQRSFLV

GDLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVHEIGIAGKQ

>[MUTANT #7]
                                                              SEQ ID NO: 24
MNRTAFCCLSLTAALILTACSSGGGGVAADIGAGLADALTAPLDHKDKSLQSLTLDQSVRKNEKLKLAAQGAEKT

YGNGDSLNTGKLKNDKVSRFDFIRQIEVDGQLITLESGEFQIYKQDHSAVVALQIEKINNPDKSDSLINQRSFLV

SGLGGEHTAFNQLPDGKAEYHGKAFSSDDAGGKLTYTIDFAAKQGHGKIEHLKTPEQNVELAAAELKADEKSHAV

ILGDTRYGSEEKGTYHLALFGDRAQEIAGSATVKIGEKVHEIGIAGKQ
```

-continued

>[MUTANT #8]
SEQ ID NO: 25
MNRTAFCCLSLTAALILTACSSGGGGVAADIGAGLADALTAPLDHKDKSLQSLTLDQSCRKNEKCKLAAQGAEKT
YGNGDSLNTGKLKNDKVSRFDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #9]
SEQ ID NO: 26
MNRTAFCCLSLTAALILTACSSGGGGVAADIGAGLADALTAPLDHKDKSLQSLTLDQSVRKNEKLKCAAQGAEKT
YGNGDSLNTGKLKNDKVSRCDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #10]
SEQ ID NO: 27
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSCLV
SGLGGEHTAFNQLPDGKAEYHGKAFSCDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #11]
SEQ ID NO: 28
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVTALQIEKINNPDKIDSLINQRSFLV
GDLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVRHIGIAGKQ

>[MUTANT #12]
SEQ ID NO: 29
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSFRI
GDIAGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #13]
SEQ ID NO: 30
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVTALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #14]
SEQ ID NO: 31
MNRTAFCCLSLTAALILTACSSGGGGVAADIGAGLADALTAPLDHKDKSLQSLTLDQSVRKNEKLKCAAQGAEKT
YGNGDSLNTGKLKNDKVSRFDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #15]
SEQ ID NO: 32
MNRTAFCCLSLTAALILTACSSGGGGVAADIGAGLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSCLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

-continued

>[MUTANT #19]
SEQ ID NO: 33
MNRTAFCCLSLTAALILTACSSGGGGVAADIGAGLADALTAPLDHKDKSLQSLTLDQVVRKNEKLKLAAQGAEKT
YGNGDSLNTGKLKNDKVSRFDFIRQIEVDGQLITLESGEFQIYKQDHSAVVALQIEKINNPDKIDSLINQRSFLV
TGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #20]
SEQ ID NO: 34
MNRTAFCCLSLTAALILTACSSGGGGVAADIGAGLADALTAPLDHKDKSLQSLTLDQVVRKNEKLKLAAQGAEKT
YGNGDSLNTGKLKNDKVSRFDFIRQIEVDGQLITLESGEFQIYKQDHSAVVALQIEKINNPDKIDSLINQRSFRV
TGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #21]
SEQ ID NO: 35
MNRTAFCCLSLTAALILTACSSGGGGVAADIGAGLADALTAPLDHKDKSLQSLTLDQVVRKNEKLKLAAQGAEKT
YGNGDSLNTGKLKNDKVSRFDFIRQIEVDGQLITLESGEFQIYKQDHSAVVALQIEKINNPDKIDSLINQRSFLV
GGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>[MUTANT #22]
SEQ ID NO: 36
MNRTAFCCLSLTAALILTACSSGGGGVAADIGAGLADALTAPLDHKDKSLQSLTLDQVVRKNEKLKLAAQGAEKT
YGNGDSLNTGKLKNDKVSRFDFIRQIEVDGQLITLESGEFQIYKQDHSAVVALQIEKINNPDKIDSLINQRSFRV
GGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ

>
SEQ ID NO: 37
GPDSDRLQQRR

>
SEQ ID NO: 38
GSKDISS

>
SEQ ID NO: 39
GSKDISSGGGG

>[M1239, mature]
SEQ ID NO: 40
CSSGGGGSGGGGVAADIGTGLADALTAPLDHKDKGLKSLTLEDSIPQNGTLTLSAQGAEKTFKAGDKDNSLNTGK
LKNDKISREDFVQKIEVDGQTITLASGEFQIYKQNHSAVVALQIEKINNPDKTDSLINQRSFLVSGLGGEHTAFN
QLPGGKAEYHGKAFSSDDPNGRLHYSIDFTKKQGYGRIEHLKTLEQNVELAAAELKADEKSHAVILGDTRYGSEE
KGTYHLALFGDRAQEIAGSATVKIGEKVHEIGIAGKQ >[v3(M1239), E243A, ΔG]
SEQ ID NO: 41
VAADIGTGLADALTAPLDHKDKGLKSLTLEDSIPQNGTLTLSAQGAEKTFKAGDKDNSLNTGKLKNDKISRFDFV
QKIEVDGQTITLASGEFQIYKQNHSAVVALQIEKINNPDKTDSLINQRSFLVSGLGGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHAIGIAGKQ >[v3(M1239), S32V + E243A, ΔG]
SEQ ID NO: 42
VAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFLVSGLGGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHAIGIAGKQ >[v3(M1239), S32V + L126R + E243A, ΔG]
SEQ ID NO: 43
VAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHAIGIAGKQ >[v3, S32V + L126R, ΔG]
SEQ ID NO: 44
VAADIGTGLADALTAPLDHKDKGLKSLTLEDVIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHEIGIAGKQ >[v2 MUTANT #3 S32V + L123R, ΔG]
SEQ ID NO: 45
VAADIGAGLADALTAPLDHKDKSLQSLTLDQVVRKNEKLKLAAQGAEKTYGNGDSLNTGKLKNDKVSRFDFIRQI
EVDGQL -continued IGAGLADALTAPLDHKDKGLQSLTLDQSVSKNEKLKLAAQGAEKTYGNGDSLNTGKLKNDKVSREDFIRQIEVDG
QLITLESGEFQVYKQSHSALTAFQTEQIQDSEHSGKMVAKRQFRIGDIAGEHTSFDKLPEGGRATYRGTAFGSDD
AGGKLTYTIDFAAKQGNGKIEHLKSPELNVDLAAADIKPDGKRHAVISGSVLYNQAEKGSYSLGIFGGKAQEVAG
SAEVKTVNGIRHIGLAAKQ >[MC58, ΔG, 'R41S' mutation]
SEQ ID NO: 49
VAADIGAGLADALTAPLDHKDKGLQSLTLDQSVSKNEKLKLAAQGAEKTYGNGDSLNTGKLKNDKVSRFDFIRQI
EVDGQLITLESGEFQVYKQSHSALTAFQTEQIQDSEHSGKMVAKRQFRIGDIAGEHTSFDKLPEGGRATYRGTAF
GSDDAGGKLTYTIDFAAKQGNGKIEHLKSPELNVDLAAADIKPDGKRHAVISGSVLYNQAEKGSYSLGIFGGKAQ
EVAGSAEVKTVNGIRHIGLAAKQ >[linker]
SEQ ID NO: 50
GSGGGG >[wild-type v2 sequence e.g. for GMMA approach]
SEQ ID NO: 51
VAADIGARLADALTAPLDHKDKSLQSLTLDQSVRKNEKLKLAAQGAEKTYGNGDSLNTGKLKNDKVSRFDFIRQI
EVDGQLITLESGEFQIYKQDHSAVVALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHEIGIAGKQ >[wild-type v3 sequence e.g. for GMMA approach]
SEQ ID NO: 52
VAADIGAGLADALTAPLDHKDKGLQSLTLDQSVRKNEKLKLAAQGAEKTYGNGDSLNTGKLKNDKVSRFDFIRQI
EVDGKLITLESGEFQVYKQSHSALTALQTEQVQDSEDSGKMVAKRQFRIGDIAGEHTSFDKLPKGGSATYRGTAF
GSDDAGGKLTYTIDFAAKQGHGKIEHLKSPELNVELATAELKADEKSHAVILGDTRYGGEEKGTYHLALFGDRAQ
EIAGSATVKIREKVHEIGIAGKQ >[m1239, L126R mutation]
SEQ ID NO: 53
VAADIGTGLADALTAPLDHKDKGLKSLTLEDSIPQNGTLTLSAQGAEKTFKAGDKDNSLNTGKLKNDKISRFDFV
QKIEVDGQTITLASGEFQIYKQNHSAVVALQIEKINNPDKTDSLINQRSFRVSGLGGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHEIGIAGKQ >[v2, 8047 strain, wild-type]
SEQ ID NO: 54
MNRTAFCCLSLTTALILTACSSGGGGVAADIGARLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ >[v2, 8047 strain, ΔG]
SEQ ID NO: 55
VAADIGARLADALTAPLDHKDKSLQSLTLDQSVRKNEKLKLAAQGAEKTYGNGDSLNTGKLKNDKVSRFDFIRQI
EVDGQLITLESGEFQIYKQDHSAVVALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHEIGIAGKQ >[v2, 'E313A' mutant, ΔG]
SEQ ID NO: 56
VAADIGAGLADALTAPLDHKDKSLQSLTLDQSVRKNEKLKLAAQGAEKTYGNGDSLNTGKLKNDKVSRFDFIRQI
EVDGQLITLESGEFQIYKQDHSAVVALQIEKINNPDKIDSLINQRSFLVSGLGGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHAIGIAGKQ >[v2, mutant #3 + 'E313A', ΔG]
SEQ ID NO: 57
VAADIGAGLADALTAPLDHKDKSLQSLTLDQVVRKNEKLKLAAQGAEKTYGNGDSLNTGKLKNDKVSRFDFIRQI
EVDGQLITLESGEFQIYKQDHSAVVALQIEKINNPDKIDSLINQRSFRVSGLGGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHAIGIAGKQ >[MUTANT #2 + #12]
SEQ ID NO: 58
VAADIGAGLADALTAPLDHKDKSLQSLTLDQVVRKNEKLKLAAQGAEKTYGNGDSLNTGKLKNDKVSRFDFIRQI
EVDGQLITLESGEFQIYKQDHSAVVALQIEKINNPDKIDSLINQRSFRIGDIAGEHTAFNQLPDGKAEYHGKAFS
SDDAGGKLTYTIDFAAKQGHGKIEHLKTPEQNVELAAAELKADEKSHAVILGDTRYGSEEKGTYHLALFGDRAQE
IAGSATVKIGEKVHEIGIAGKQ >[v2, strain 8047 strain, mutant #4, mature
MNRTAFCCLSLTTALILTACSSGGGGVAADIGARLADALTAPLDHKDKSLQSLTLDQSVRKNEKLKLAAQGAEKT
YGNGDSLNTGKLKNDKVSRFDFIRQIEVDGQLITLESGEFQIYKQDHSAVVALQIEKINNPDKIDSLINQRSFLV
SGLGGEHTAFNQLPDGKAEYHGKAFSSDDAGGKLTYTIDFAAKQGHGKIEHLKTPEQNVELAAAELKADEKSHAV
ILGDTRYGSEEKGTYHLALFGDRAQEIAGSATVKIGEKVHEIGIAGKQ SEQ ID NO: 59
CSSGGGGVAADIGARLADALTAPLDHKDKSLQSLTLDQSVRKNEKLKLAAQGAEKTYGNGDSLNTGKLKNDKVSR
FDFIRQIEVDGQLITLESGEFQIYKQDHSAVVALQIEKINNPDKIDSLINQRSFRVSGLGGEHTAFNQLPDGKAE
YHGKAFSSDDAGGKLTYTIDFAAKQGHGKIEHLKTPEQNVELAAAELKADEKSHAVILGDTRYGSEEKGTYHLAL
FGDRAQEIAGSATVKIGEKVHEIGIAGKQ >[v2, strain 8047 strain, mutant #3, mature}
SEQ ID NO: 60
CSSGGGGVAADIGARLADALTAPLDHKDKSLQSLTLDQVVRKNEKLKLAAQGAEKTYGNGDSLNTGKLKNDKVSR
FDFIRQIEVDGQLITLESGEFQIYKQDHSAVVALQIEKINNPDKIDSLINQRSFRVSGLGGEHTAFNQLPDGKAE
YHGKAFSSDDAGGKLTYTIDFAAKQGHGKIEHLKTPEQNVELAAAELKADEKSHAVILGDTRYGSEEKGTYHLAL
FGDRAQEIAGSATVKIGEKVHEIGIAGKQ >[v3, mutant #2 + #12, ΔG]
SEQ ID NO: 61
VAADIGTGLADALTAPLDHKDKGLKSLTLEDVIPQNGTLTLSAQGAEKTFKAGDKDNSLNTGKLKNDKISREDEV
QKIEVDGQTITLASGEFQIYKQNHSAVVALQIEKINNPDKTDSLINQRSFRIGDIAGEHTAFNQLPGGKAEYHGK
AFSSDDPNGRLHYSIDFTKKQGYGRIEHLKTLEQNVELAAAELKADEKSHAVILGDTRYGSEEKGTYHLALFGDR
AQEIAGSATVKIGEKVHEIGIAGKQ

REFERENCES

[1] WO99/57280.
[2] Masignani et al. (2003) *J Exp Med* 197:789-799.
[3] Welsch et al. (2004) *J Immunol* 172:5605-15.
[4] Hou et al. (2005) *J Infect Dis* 192(4):580-90.
[5] WO03/063766.
[6] Fletcher et al. (2004) *Infect Immun* 72:2088-2100.
[7] Zhu et al. (2005) *Infect Immun* 73(10):6838-45.
[8] Cendron et al. (2011) *Acta Crystallogr Sect F Struct Biol Cryst Commun.* 67:531-5.
[9] Mascioni et al. (2009) *J Biol Chem* 284:8738-46.
[10] Pizza et al. (2008) *Vaccine* 26 Suppl 8:146-8.
[11] Malito et al. (2013) *PNAS USA* 110:3304-9.
[12] Marshall et al. (2012) *Pediatr Infect Dis J* 31:1061-8.
[13] McNeil et al. (2013) *Microbiol Mol Biol Rev* 77:234-52.
[14] Serruto et al. (2012) *Vaccine* 30 Suppl 2: B87-97.
[15] Scarselli et al. (2011) *Sci Transl Med* 3:91ra62.
[16] WO2011/051893.
[17] WO2010/046715.
[18] Schneider et al. (2009) *Nature* 458:890-5.
[19] WO2011/126863.
[20] Beernink et al. (2010) *Clin Vaccine Immunol* 17:1074-8.
[21] Beernink et al. (2011) *J Immunol* 186:3606-14.
[22] Rossi et al. (2013) *Vaccine* 31:5451-7.
[23] van der Veen et al. (2014) *Infect Immun* PMID 24379280.
[24] Johnson et al. (2012) *PLoS Pathogen* 8:e1002981.
[25] Pajon et al. (2012) *Infect Immun* 80:2667-77.
[26] Granoff et al. (2013) *Clin Vaccine Immunol* 20:1099-107.
[27] Beernink et al. (2008) *Infect Immun* 76:4232-40.
[28] Scarselli et al. (2009) *J Mol Biol* 386:97-108.
[29] Giuntini et al. (2012) *PLoS One* 7:e34272.
[30] Vu et al. (2012) *Sci Rep* 2:341.

[31] Faleri et al. (2013) *FASEB J* fj. 13-239012.
[32] Johnson (2013) *Arch Biochem Biophys* 531:100-9.
[33] Bruylants et al. (2005) *Current Medicinal Chemistry* 12:2011-20.
[34] Veggi et al. (2012) *Biochemistry* 51:9384-93.
[35] WO2014/030003.
[36] Jongerius et al. (2013) *PLoS Pathog* 9(8): e1003528.
[37] Pizza et al. (2000) *Science* 287:1816-1820.
[38] WO2007/028408.
[39] http://pubmlst.org/neisseria/
[40] Budroni et al. (2011) *PNAS USA* 108:4494-99.
[41] Goldschneider et al. (1969) *J. Exp. Med.* 129:1307-26.
[42] Santos et al. (2001) *Clinical and Diagnostic Laboratory Immunology* 8:616-23.
[43] Frasch et al. (2009) *Vaccine* 27S:B112-6.
[44] Gennaro (2000) *Remington: The Science and Practice of Pharmacy.* 20th edition, ISBN: 0683306472.
[45] WO03/009869.
[46] *Vaccine Design* . . . (1995) eds. Powell & Newman. ISBN: 030644867X. Plenum.
[47] Tettelin et al. (2000) *Science* 287:1809-1815.
[48] WO00/66741.
[49] Martin et al. (1997) *J Exp Med* 185(7):1173-83.
[50] WO96/29412.
[51] Perkins-Balding et al. (2003) *Microbiology* 149:3423-35.
[52] WO01/55182.
[53] WO01/38350.
[54] WO00/23595.
[55] Giuliani et al. (2006) *Proc Natl Acad Sci USA.* 103: 10834-9.
[56] WO2004/032958.
[57] Costantino et al. (1992) *Vaccine* 10:691-698.
[58] Costantino et al. (1999) *Vaccine* 17:1251-1263.
[59] WO03/007985.
[60] Watson (2000) *Pediatr Infect Dis J* 19:331-332.
[61] Rubin (2000) *Pediatr Clin North Am* 47:269-285, v.
[62] Jedrzejas (2001) *Microbiol Mol Biol Rev* 65:187-207.
[63] Bell (2000) *Pediatr Infect Dis J* 19:1187-1188.
[64] Iwarson (1995) *APMIS* 103:321-326.
[65] Gerlich et al. (1990) *Vaccine* 8 Suppl:S63-68 & 79-80.
[66] *Vaccines* (1988) eds. Plotkin & Mortimer. ISBN 0-7216-1946-0.
[67] Del Guidice et al. (1998) *Molecular Aspects of Medicine* 19:1-70.
[68] Gustafsson et al. (1996) *N. Engl. J. Med.* 334:349-355.
[69] Rappuoli et al. (1991) *TIBTECH* 9:232-238.
[70] Sutter et al. (2000) *Pediatr Clin North Am* 47:287-308.
[71] Zimmerman & Spann (1999) *Am Fam Physician* 59:113-118, 125-126.
[72] McMichael (2000) *Vaccine* 19 Suppl 1:S101-107.
[73] Schuchat (1999) *Lancet* 353(9146):51-6.
[74] WO02/34771.
[75] Dale (1999) *Infect Dis Clin North Am* 13:227-43, viii.
[76] Ferretti et al. (2001) *PNAS USA* 98: 4658-4663.
[77] Kuroda et al. (2001) *Lancet* 357(9264):1225-1240; see also pages 1218-1219.
[78] Jones (2001) *Curr Opin Investig Drugs* 2:47-49.
[79] Ravenscroft et al. (1999) *Vaccine* 17:2802-2816.
[80] WO03/080678.
[81] *Research Disclosure,* 453077 (January 2002).
[82] EP-A-0372501.
[83] EP-A-0378881.
[84] EP-A-0427347.
[85] WO93/17712.
[86] WO94/03208.
[87] WO98/58668.
[88] EP-A-0471177.
[89] WO91/01146.
[90] Falugi et al. (2001) *Eur J Immunol* 31:3816-3824.
[91] Baraldo et al. (2004) *Infect Immun* 72(8):4884-7.
[92] EP-A-0594610.
[93] Ruan et al. (1990) *J Immunol* 145:3379-3384.
[94] WO00/56360.
[95] Kuo et al. (1995) *Infect Immun* 63:2706-13.
[96] Michon et al. (1998) *Vaccine.* 16:1732-41.
[97] WO02/091998.
[98] WO01/72337.
[99] WO00/61761.
[100] WO00/33882.
[101] Lees et al. (1996) *Vaccine* 14:190-198.
[102] WO95/08348.
[103] U.S. Pat. No. 4,882,317
[104] U.S. Pat. No. 4,695,624
[105] Porro et al. (1985) *Mol Immunol* 22:907-919.s
[106] EP-A-0208375
[107] WO00/10599
[108] Gever et al. *Med. Microbiol. Immunol,* 165: 171-288 (1979).
[109] U.S. Pat. No. 4,057,685.
[110] U.S. Pat. Nos. 4,673,574; 4,761,283; 4,808,700.
[111] U.S. Pat. No. 4,459,286.
[112] U.S. Pat. No. 4,965,338.
[113] U.S. Pat. No. 4,663,160.
[114] U.S. Pat. No. 4,761,283
[115] U.S. Pat. No. 4,356,170
[116] WO02/09643.
[117] Katial et al. (2002) *Infect Immun* 70:702-707.
[118] WO01/52885.
[119] European patent 0301992.
[120] Bjune et al. (1991) *Lancet* 338(8775):1093-1096.
[121] Fukasawa et al. (1999) *Vaccine* 17:2951-2958.
[122] WO02/09746.
[123] Rosenqvist et al. (1998) *Dev. Biol. Stand.* 92:323-333.
[124] WO01/09350.
[125] European patent 0449958.
[126] EP-A-0996712.
[127] EP-A-0680512.
[128] WO02/062378.
[129] WO99/59625.
[130] U.S. Pat. No. 6,180,111.
[131] WO01/34642.
[132] WO03/051379.
[133] U.S. Pat. No. 6,558,677.
[134] WO2004/019977.
[135] WO02/062380.
[136] WO00/25811.
[137] Peeters et al. (1996) *Vaccine* 14:1008-1015.
[138] Vermont et al. (2003) *Infect Immun* 71:1650-1655.
[139] WO2006/081259.
[140] European patent 0011243.
[141] Fredriksen et al. (1991) *NIPH Ann.* 14(2):67-80.
[142] WO01/91788.
[143] WO2005/004908.
[144] WO98/56901.
[145] Claassen et al. (1996) 14(10):1001-8.
[146] WO99/10497.
[147] Steeghs et al. (2001) *The EMBO Journal* 20:6937-6945.
[148] Fisseha et al. (2005) *Infect Immun* 73:4070-80.
[149] WO2004/015099.
[150] WO2004/014417.
[151] WO2004/046177.
[152] WO2006/046143.

[153] Adu-Bobie et al. (2004) *Infect Immun* 72:1914-19.
[154] WO2011/036562.
[155] Koeberling et al. (2014) *Vaccine* 32:2688-95.
[156] WO2013/033398.
[157] WO2013/113917.
[158] Needleman & Wunsch (1970) *J Mol. Biol.* 48, 443-453.
[159] Rice et al. (2000) *Trends Genet* 16:276-277.
[160] WO01/64920.
[161] WO03/020756.
[162] WO2004/048404.
[163] WO2004/094596.
[164] WO2006/024954.
[165] WO2007/060548.
[166] WO2009/104097.
[167] WO2013/132452.
[168] Krissinel & Henrick (2007) *J Mol. Biol.* 372:774-97.

TABLE 1

| # | Residue(s)* | Mutation(s) | Notes | SEQ ID NO | Chym ** | Tm1 °C. | Tm2 °C. | Mon *** |
|---|---|---|---|---|---|---|---|---|
| 1 | H239 + E240 | R, H | Interface between N- and C-terminal domains. The aim is to mimic v1. An additional DSC transition was observed at 100.3° C., and some aggregation was detected. | 18 | Yes | N/A | 83.5 | 34.29 |
| 2 | S32 | V | N-terminal domain. Hydrophilic S32 side chain points into hydrophobic cavity. The aim is to increase hydrophobicity and stabilise the cavity. | 19 | Yes | 57.0 | 84.2 | 80.38 |
| 3 | S32 + L123 | V, R | Mutants #2 + #4 | 20 | Yes |

```
                65                  70                  75                  80
Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
            115                 120                 125

Gln Thr Glu Gln Ile Gln Asp Ser Glu His Ser Gly Lys Met Val Ala
        130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
        195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
                245                 250                 255

Ala Glu Val Lys Thr Val Asn Gly Ile Arg His Ile Gly Leu Ala Ala
            260                 265                 270

Lys Gln

<210> SEQ ID NO 2
<211> LENGTH: 273
<212> TYPE: PRT
<213> ORGANISM: Neisseria meningitidis

<400> SEQUENCE: 2

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
```

```
            165                 170                 175
Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 3
<211> LENGTH: 281
<212> TYPE: PRT
<213> ORGANISM: Neisseria meningitidis

<400> SEQUENCE: 3

Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
```

His Glu Ile Gly Ile Ala Gly Lys Gln
            275                 280

<210> SEQ ID NO 4
<211> LENGTH: 254
<212> TYPE: PRT
<213> ORGANISM: Neisseria meningitidis

<400> SEQUENCE: 4

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 5
<211> LENGTH: 247
<212> TYPE: PRT
<213> ORGANISM: Neisseria meningitidis

<400> SEQUENCE: 5

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp

```
                50                  55                  60
Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 6
<211> LENGTH: 488
<212> TYPE: PRT
<213> ORGANISM: Neisseria meningitidis

<400> SEQUENCE: 6

Met Phe Lys Arg Ser Val Ile Ala Met Ala Cys Ile Phe Ala Leu Ser
 1               5                  10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
        50                  55                  60

Ser Ala Gln Gly Ser Gln Asp Met Ala Ala Val Ser Glu Glu Asn Thr
 65                  70                  75                  80

Gly Asn Gly Gly Ala Val Thr Ala Asp Asn Pro Lys Asn Glu Asp Glu
                 85                  90                  95

Val Ala Gln Asn Asp Met Pro Gln Asn Ala Ala Gly Thr Asp Ser Ser
                100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
        130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175
```

```
Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
            245                 250                 255

Asn Tyr Lys Lys Asp Gly Lys Asn Asp Lys Phe Val Gly Leu Val Ala
        260                 265                 270

Asp Ser Val Gln Met Lys Gly Ile Asn Gln Tyr Ile Ile Phe Tyr Lys
    275                 280                 285

Pro Lys Pro Thr Ser Phe Ala Arg Phe Arg Arg Ser Ala Arg Ser Arg
290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
            325                 330                 335

Asn Ile Phe Ala Pro Glu Gly Asn Tyr Arg Tyr Leu Thr Tyr Gly Ala
        340                 345                 350

Glu Lys Leu Pro Gly Gly Ser Tyr Ala Leu Arg Val Gln Gly Glu Pro
    355                 360                 365

Ala Lys Gly Glu Met Leu Ala Gly Ala Val Tyr Asn Gly Glu Val
370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
            405                 410                 415

Asp Ser Gly Asp Asp Leu His Met Gly Thr Gln Lys Phe Lys Ala Ala
        420                 425                 430

Ile Asp Gly Asn Gly Phe Lys Gly Thr Trp Thr Glu Asn Gly Ser Gly
    435                 440                 445

Asp Val Ser Gly Lys Phe Tyr Gly Pro Ala Gly Glu Glu Val Ala Gly
450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
            485

<210> SEQ ID NO 7
<211> LENGTH: 364
<212> TYPE: PRT
<213> ORGANISM: Neisseria meningitidis

<400> SEQUENCE: 7

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
            20                  25                  30

Lys Lys Ala Ala Thr Val Ala Ile Val Ala Ala Tyr Asn Asn Gly Gln
        35                  40                  45

Glu Ile Asn Gly Phe Lys Ala Gly Glu Thr Ile Tyr Asp Ile Gly Glu
    50                  55                  60
```

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
130                 135                 140

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
                165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
        195                 200                 205

Lys Gln Thr Ala Glu Glu Thr Lys Gln Asn Val Asp Ala Lys Val Lys
210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
            260                 265                 270

Ala Arg Ile Asp Ser Leu Asp Lys Asn Val Ala Asn Leu Arg Lys Glu
        275                 280                 285

Thr Arg Gln Gly Leu Ala Glu Gln Ala Ala Leu Ser Gly Leu Phe Gln
290                 295                 300

Pro Tyr Asn Val Gly Arg Phe Asn Val Thr Ala Ala Val Gly Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 8
<211> LENGTH: 174
<212> TYPE: PRT
<213> ORGANISM: Neisseria meningitidis

<400> SEQUENCE: 8

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
            20                  25                  30

His Ala Lys Ala Ser Ser Ser Leu Gly Ser Ala Lys Gly Phe Ser Pro
        35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu

-continued

```
                65                  70                  75                  80
        Tyr Ser Ile Gly Ala Ser Ala Ile Tyr Asp Phe Asp Thr Gln Ser Pro
                        85                  90                  95

Val Lys Pro Tyr Leu Gly Ala Arg Leu Ser Leu Asn Arg Ala Ser Val
                       100                 105                 110

Asp Leu Gly Gly Ser Asp Ser Phe Ser Gln Thr Ser Ile Gly Leu Gly
                       115                 120                 125

Val Leu Thr Gly Val Ser Tyr Ala Val Thr Pro Asn Val Asp Leu Asp
                       130                 135                 140

Ala Gly Tyr Arg Tyr Asn Tyr Ile Gly Lys Val Asn Thr Val Lys Asn
        145                 150                 155                 160

Val Arg Ser Gly Glu Leu Ser Ala Gly Val Arg Val Lys Phe
                       165                 170

<210> SEQ ID NO 9
<211> LENGTH: 792
<212> TYPE: PRT
<213> ORGANISM: Neisseria meningitidis

<400> SEQUENCE: 9

Met Lys Pro Leu Gln Met Leu Pro Ile Ala Ala Leu Val Gly Ser Ile
        1               5                   10                  15

Phe Gly Asn Pro Val Leu Ala Ala Asp Glu Ala Ala Thr Glu Thr Thr
                        20                  25                  30

Pro Val Lys Ala Glu Ile Lys Ala Val Arg Val Lys Gly Gln Arg Asn
                        35                  40                  45

Ala Pro Ala Ala Val Glu Arg Val Asn Leu Asn Arg Ile Lys Gln Glu
                    50                  55                  60

Met Ile Arg Asp Asn Lys Asp Leu Val Arg Tyr Ser Thr Asp Val Gly
        65                  70                  75                  80

Leu Ser Asp Ser Gly Arg His Gln Lys Gly Phe Ala Val Arg Gly Val
                        85                  90                  95

Glu Gly Asn Arg Val Gly Val Ser Ile Asp Gly Val Asn Leu Pro Asp
                       100                 105                 110

Ser Glu Glu Asn Ser Leu Tyr Ala Arg Tyr Gly Asn Phe Asn Ser Ser
                       115                 120                 125

Arg Leu Ser Ile Asp Pro Glu Leu Val Arg Asn Ile Glu Ile Val Lys
                       130                 135                 140

Gly Ala Asp Ser Phe Asn Thr Gly Ser Gly Ala Leu Gly Gly Gly Val
        145                 150                 155                 160

Asn Tyr Gln Thr Leu Gln Gly Arg Asp Leu Leu Asp Asp Arg Gln
                       165                 170                 175

Phe Gly Val Met Met Lys Asn Gly Tyr Ser Thr Arg Asn Arg Glu Trp
                       180                 185                 190

Thr Asn Thr Leu Gly Phe Gly Val Ser Asn Asp Arg Val Asp Ala Ala
                       195                 200                 205

Leu Leu Tyr Ser Gln Arg Arg Gly His Glu Thr Glu Ser Ala Gly Asn
                       210                 215                 220

Arg Gly Tyr Ala Val Glu Gly Glu Gly Ser Gly Ala Asn Ile Arg Gly
        225                 230                 235                 240

Ser Ala Arg Gly Ile Pro Asp Ser Ser Lys His Lys Tyr Asn His His
                       245                 250                 255

Ala Leu Gly Lys Ile Ala Tyr Gln Ile Asn Asp Asn His Arg Ile Gly
                       260                 265                 270
```

```
Ala Ser Leu Asn Gly Gln Gln Gly His Asn Tyr Thr Val Glu Glu Ser
            275                 280                 285

Tyr Asn Leu Thr Ala Ser Ser Trp Arg Glu Ala Asp Asp Val Asn Arg
            290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
            325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met
            355                 360                 365

Asp Thr Arg Phe Lys Arg Phe Thr Leu Arg Leu Asp Ser His Pro Leu
        370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Asp Tyr Tyr Phe Ser Gly
                405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
        435                 440                 445

Ser Ser Arg Ala Gly Ile Arg Tyr Asp His Thr Lys Met Thr Pro Gln
        450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
            485                 490                 495

Asn Gln Ala Trp Arg Val Gly Tyr Asp Ile Thr Ser Gly Tyr Arg Val
            500                 505                 510

Pro Asn Ala Ser Glu Val Tyr Phe Thr Tyr Asn His Gly Ser Gly Asn
            515                 520                 525

Trp Leu Pro Asn Pro Asn Leu Lys Ala Glu Arg Ser Thr Thr His Thr
530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Glu Gln Lys Leu Thr
            565                 570                 575

Thr Ser Gly Thr Pro Gly Cys Thr Glu Glu Asn Ala Tyr Tyr Gly Ile
            580                 585                 590

Cys Ser Asp Pro Tyr Lys Glu Lys Leu Asp Trp Gln Met Lys Asn Ile
            595                 600                 605

Asp Lys Ala Arg Ile Arg Gly Ile Glu Leu Thr Gly Arg Leu Asn Val
            610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
            645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
            675                 680                 685

Val Lys Asp Ala Gln Tyr Thr Val Tyr Glu Asn Lys Gly Trp Gly Thr
```

```
            690                 695                 700
Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
                740                 745                 750

Asp Ser Leu Arg Gly Leu Tyr Ser Tyr Ser Thr Thr Asn Ala Val Asp
            755                 760                 765

Arg Asp Gly Lys Gly Leu Asp Arg Tyr Arg Ala Pro Gly Arg Asn Tyr
770                 775                 780

Ala Val Ser Leu Glu Trp Lys Phe
785                 790

<210> SEQ ID NO 10
<211> LENGTH: 591
<212> TYPE: PRT
<213> ORGANISM: Neisseria meningitidis

<400> SEQUENCE: 10

Met Asn Lys Ile Tyr Arg Ile Ile Trp Asn Ser Ala Leu Asn Ala Trp
1               5                   10                  15

Val Val Ser Glu Leu Thr Arg Asn His Thr Lys Arg Ala Ser Ala
                20                  25                  30

Thr Val Lys Thr Ala Val Leu Ala Thr Leu Phe Ala Thr Val Gln
                35                  40                  45

Ala Ser Ala Asn Asn Glu Glu Gln Glu Glu Asp Leu Tyr Leu Asp Pro
50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
                195                 200                 205

Lys Lys Arg Ala Ala Ser Val Lys Asp Val Leu Asn Ala Gly Trp Asn
                210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270
```

```
Lys Ile Gly Ala Lys Thr Ser Val Ile Lys Glu Lys Asp Gly Lys Leu
            275                 280                 285

Val Thr Gly Lys Asp Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
            325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Gln Gly Asn Ile
            355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
            450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
            485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590

<210> SEQ ID NO 11
<211> LENGTH: 1457
<212> TYPE: PRT
<213> ORGANISM: Neisseria meningitidis

<400> SEQUENCE: 11

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60
```

```
Ala Val Gly Ala Lys Asp Ile Glu Val Tyr Asn Lys Lys Gly Glu Leu
 65                  70                  75                  80

Val Gly Lys Ser Met Thr Lys Ala Pro Met Ile Asp Phe Ser Val Val
                 85                  90                  95

Ser Arg Asn Gly Val Ala Ala Leu Val Gly Asp Gln Tyr Ile Val Ser
                100                 105                 110

Val Ala His Asn Gly Gly Tyr Asn Asn Val Asp Phe Gly Ala Glu Gly
                115                 120                 125

Arg Asn Pro Asp Gln His Arg Phe Thr Tyr Lys Ile Val Lys Arg Asn
130                 135                 140

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
                180                 185                 190

Asp Arg Val Arg Ile Gly Ala Gly Arg Gln Tyr Trp Arg Ser Asp Glu
                195                 200                 205

Asp Glu Pro Asn Asn Arg Glu Ser Ser Tyr His Ile Ala Ser Ala Tyr
210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
                260                 265                 270

Ile Tyr Asp Ala Gln Lys Gln Lys Trp Leu Ile Asn Gly Val Leu Gln
                275                 280                 285

Thr Gly Asn Pro Tyr Ile Gly Lys Ser Asn Gly Phe Gln Leu Val Arg
                290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
                340                 345                 350

Asn Arg Leu Lys Thr Arg Thr Val Gln Leu Phe Asn Val Ser Leu Ser
                355                 360                 365

Glu Thr Ala Arg Glu Pro Val Tyr His Ala Ala Gly Gly Val Asn Ser
                370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
                420                 425                 430

Thr Trp Gln Gly Ala Gly Val His Ile Ser Glu Asp Ser Thr Val Thr
                435                 440                 445

Trp Lys Val Asn Gly Val Ala Asn Asp Arg Leu Ser Lys Ile Gly Lys
                450                 455                 460

Gly Thr Leu His Val Gln Ala Lys Gly Glu Asn Gln Gly Ser Ile Ser
465                 470                 475                 480
```

-continued

Val Gly Asp Gly Thr Val Ile Leu Asp Gln Gln Ala Asp Asp Lys Gly
                        485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
            515                 520                 525

Gly Phe Arg Gly Gly Arg Leu Asp Leu Asn Gly His Ser Leu Ser Phe
            530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
            595                 600                 605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
            660                 665                 670

Asn Asp Trp Ile Asn Arg Thr Phe Lys Ala Glu Asn Phe Gln Ile Lys
            675                 680                 685

Gly Gly Gln Ala Val Val Ser Arg Asn Val Ala Lys Val Lys Gly Asp
            690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Asp Leu Ala Asp His Ala His Leu
            755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
            850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu

```
                900             905             910
Asn Ser Ala Tyr Arg His Asp Ala Ala Gly Ala Gln Thr Gly Ser Ala
        915                 920                 925
Thr Asp Ala Pro Arg Arg Ser Arg Ser Arg Ser Arg Ser Leu Leu
    930                 935                 940
Ser Val Thr Pro Pro Thr Ser Val Glu Ser Arg Phe Asn Thr Leu Thr
945                 950                 955                 960
Val Asn Gly Lys Leu Asn Gly Gln Gly Thr Phe Arg Phe Met Ser Glu
                965                 970                 975
Leu Phe Gly Tyr Arg Ser Asp Lys Leu Lys Leu Ala Glu Ser Ser Glu
            980                 985                 990
Gly Thr Tyr Thr Leu Ala Val Asn Asn Thr Gly Asn Glu Pro Ala Ser
        995                 1000                1005
Leu Glu Gln Leu Thr Val Val Glu Gly Lys Asn Lys Pro Leu Ser
    1010                1015                1020
Glu Asn Leu Asn Phe Thr Leu Gln Asn Glu His Val Asp Ala Gly Ala
1025                1030                1035                1040
Trp Arg Tyr Gln Leu Ile Arg Lys Asp Gly Glu Phe Arg Leu His Asn
            1045                1050                1055
Pro Val Lys Glu Gln Glu Leu Ser Asp Lys Leu Gly Lys Ala Glu Ala
            1060                1065                1070
Lys Lys Gln Ala Glu Lys Asp Asn Ala Gln Ser Leu Asp Ala Leu Ile
        1075                1080                1085
Ala Ala Gly Arg Asp Ala Val Glu Lys Thr Glu Ser Val Ala Glu Pro
    1090                1095                1100
Ala Arg Gln Ala Gly Gly Glu Asn Val Gly Ile Met Gln Ala Glu Glu
1105                1110                1115                1120
Glu Lys Lys Arg Val Gln Ala Asp Lys Asp Thr Ala Leu Ala Lys Gln
            1125                1130                1135
Arg Glu Ala Glu Thr Arg Pro Ala Thr Thr Ala Phe Pro Arg Ala Arg
            1140                1145                1150
Arg Ala Arg Arg Asp Leu Pro Gln Leu Gln Pro Gln Pro Gln
        1155                1160                1165
Pro Gln Arg Asp Leu Ile Ser Arg Tyr Ala Asn Ser Gly Leu Ser Glu
    1170                1175                1180
Phe Ser Ala Thr Leu Asn Ser Val Phe Ala Val Gln Asp Glu Leu Asp
1185                1190                1195                1200
Arg Val Phe Ala Glu Asp Arg Arg Asn Ala Val Trp Thr Ser Gly Ile
            1205                1210                1215
Arg Asp Thr Lys His Tyr Arg Ser Gln Asp Phe Arg Ala Tyr Arg Gln
            1220                1225                1230
Gln Thr Asp Leu Arg Gln Ile Gly Met Gln Lys Asn Leu Gly Ser Gly
        1235                1240                1245
Arg Val Gly Ile Leu Phe Ser His Asn Arg Thr Glu Asn Thr Phe Asp
    1250                1255                1260
Asp Gly Ile Gly Asn Ser Ala Arg Leu Ala His Gly Ala Val Phe Gly
1265                1270                1275                1280
Gln Tyr Gly Ile Asp Arg Phe Tyr Ile Gly Ile Ser Ala Gly Ala Gly
            1285                1290                1295
Phe Ser Ser Gly Ser Leu Ser Asp Gly Ile Gly Gly Lys Ile Arg Arg
        1300                1305                1310
Arg Val Leu His Tyr Gly Ile Gln Ala Arg Tyr Arg Ala Gly Phe Gly
    1315                1320                1325
```

```
Gly Phe Gly Ile Glu Pro His Ile Gly Ala Thr Arg Tyr Phe Val Gln
        1330                1335                1340

Lys Ala Asp Tyr Arg Tyr Glu Asn Val Asn Ile Ala Thr Pro Gly Leu
1345                1350                1355                1360

Ala Phe Asn Arg Tyr Arg Ala Gly Ile Lys Ala Asp Tyr Ser Phe Lys
                1365                1370                1375

Pro Ala Gln His Ile Ser Ile Thr Pro Tyr Leu Ser Leu Ser Tyr Thr
            1380                1385                1390

Asp Ala Ala Ser Gly Lys Val Arg Thr Arg Val Asn Thr Ala Val Leu
        1395                1400                1405

Ala Gln Asp Phe Gly Lys Thr Arg Ser Ala Glu Trp Gly Val Asn Ala
    1410                1415                1420

Glu Ile Lys Gly Phe Thr Leu Ser Leu His Ala Ala Ala Lys Gly
1425                1430                1435                1440

Pro Gln Leu Glu Ala Gln His Ser Ala Gly Ile Lys Leu Gly Tyr Arg
                1445                1450                1455

Trp

<210> SEQ ID NO 12
<211> LENGTH: 797
<212> TYPE: PRT
<213> ORGANISM: Neisseria meningitidis

<400> SEQUENCE: 12

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
50              55                  60

Leu Tyr Ala Thr Gly Phe Phe Asp Asp Val Arg Val Glu Thr Ala Asp
65              70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240
```

```
Asp Thr Asp Ile Gln Thr Asn Glu Asp Lys Thr Lys Gln Thr Ile Lys
                245                 250                 255
Ile Thr Val His Glu Gly Gly Arg Phe Arg Trp Gly Lys Val Ser Ile
            260                 265                 270
Glu Gly Asp Thr Asn Glu Val Pro Lys Ala Glu Leu Glu Lys Leu Leu
        275                 280                 285
Thr Met Lys Pro Gly Lys Trp Tyr Glu Arg Gln Gln Met Thr Ala Val
    290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Glu Thr Lys Thr Val Asp
                325                 330                 335
Phe Val Leu His Ile Glu Pro Gly Arg Lys Ile Tyr Val Asn Glu Ile
            340                 345                 350
His Ile Thr Gly Asn Asn Lys Thr Arg Asp Glu Val Val Arg Arg Glu
        355                 360                 365
Leu Arg Gln Met Glu Ser Ala Pro Tyr Asp Thr Ser Lys Leu Gln Arg
    370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
        435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Thr Ala Gly
            500                 505                 510
Ala Gly Ile Arg Met Ser Val Pro Val Thr Glu Tyr Asp Arg Val Asn
        515                 520                 525
Phe Gly Leu Val Ala Glu His Leu Thr Val Asn Thr Tyr Asn Lys Ala
    530                 535                 540
Pro Lys His Tyr Ala Asp Phe Ile Lys Lys Tyr Gly Lys Thr Asp Gly
545                 550                 555                 560
Thr Asp Gly Ser Phe Lys Gly Trp Leu Tyr Lys Gly Thr Val Gly Trp
                565                 570                 575
Gly Arg Asn Lys Thr Asp Ser Ala Leu Trp Pro Thr Arg Gly Tyr Leu
            580                 585                 590
Thr Gly Val Asn Ala Glu Ile Ala Leu Pro Gly Ser Lys Leu Gln Tyr
        595                 600                 605
Tyr Ser Ala Thr His Asn Gln Thr Trp Phe Pro Leu Ser Lys Thr
    610                 615                 620
Phe Thr Leu Met Leu Gly Gly Glu Val Gly Ile Ala Gly Gly Tyr Gly
625                 630                 635                 640
Arg Thr Lys Glu Ile Pro Phe Phe Glu Asn Phe Tyr Gly Gly Gly Leu
                645                 650                 655
```

```
Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
            725                 730                 735

Asn Ile Tyr Gly Ala Gly Asn Thr His Lys Ser Thr Phe Thr Asn Glu
        740                 745                 750

Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Lys Pro Glu Asp
    770                 775                 780

Glu Ile Gln Arg Phe Gln Phe Gln Leu Gly Thr Thr Phe
785                 790                 795
```

<210> SEQ ID NO 13
<211> LENGTH: 180
<212> TYPE: PRT
<213> ORGANISM: Neisseria meningitidis

<400> SEQUENCE: 13

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
            85                  90                  95

Ile Thr Val Ala Ser Leu Pro Arg Thr Ala Gly Asp Ile Ala Gly Asp
        100                 105                 110

Thr Trp Asn Thr Ser Lys Val Arg Ala Thr Leu Leu Gly Ile Ser Pro
    115                 120                 125

Ala Thr Arg Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
            165                 170                 175

Tyr Val Gln Arg
            180
```

<210> SEQ ID NO 14
<211> LENGTH: 644
<212> TYPE: PRT
<213> ORGANISM: Neisseria meningitidis

<400> SEQUENCE: 14

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
                100                 105                 110

Gly Glu Ser Glu Gln Pro Ala Asn Gln Pro Asp Met Ala Asn Thr Ala
            115                 120                 125

Asp Gly Met Gln Gly Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
                180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
        210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
        340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Gly Asp Val
```

```
                420             425             430
Ser Gly Lys Phe Tyr Gly Pro Ala Gly Glu Val Ala Gly Lys Tyr
            435             440             445
Ser Tyr Arg Pro Thr Asp Ala Glu Lys Gly Gly Phe Gly Val Phe Ala
450             455             460
Gly Lys Lys Glu Gln Asp Gly Ser Gly Gly Gly Ala Thr Tyr Lys
465             470             475             480
Val Asp Glu Tyr His Ala Asn Ala Arg Phe Ala Ile Asp His Phe Asn
            485             490             495
Thr Ser Thr Asn Val Gly Gly Phe Tyr Gly Leu Thr Gly Ser Val Glu
            500             505             510
Phe Asp Gln Ala Lys Arg Asp Gly Lys Ile Asp Ile Thr Ile Pro Val
            515             520             525
Ala Asn Leu Gln Ser Gly Ser Gln His Phe Thr Asp His Leu Lys Ser
            530             535             540
Ala Asp Ile Phe Asp Ala Ala Gln Tyr Pro Asp Ile Arg Phe Val Ser
545             550             555             560
Thr Lys Phe Asn Phe Asn Gly Lys Lys Leu Val Ser Val Asp Gly Asn
            565             570             575
Leu Thr Met His Gly Lys Thr Ala Pro Val Lys Leu Lys Ala Glu Lys
            580             585             590
Phe Asn Cys Tyr Gln Ser Pro Met Ala Lys Thr Glu Val Cys Gly Gly
            595             600             605
Asp Phe Ser Thr Thr Ile Asp Arg Thr Lys Trp Gly Val Asp Tyr Leu
            610             615             620
Val Asn Val Gly Met Thr Lys Ser Val Arg Ile Asp Ile Gln Ile Glu
625             630             635             640
Ala Ala Lys Gln

<210> SEQ ID NO 15
<211> LENGTH: 327
<212> TYPE: PRT
<213> ORGANISM: Neisseria meningitidis

<400> SEQUENCE: 15

Ala Thr Asn Asp Asp Val Lys Lys Ala Ala Thr Val Ala Ile Ala
1               5               10              15
Ala Ala Tyr Asn Asn Gly Gln Glu Ile Asn Gly Phe Lys Ala Gly Glu
                20              25              30
Thr Ile Tyr Asp Ile Asp Glu Asp Gly Thr Ile Thr Lys Lys Asp Ala
            35              40              45
Thr Ala Ala Asp Val Glu Ala Asp Asp Phe Lys Gly Leu Gly Leu Lys
50              55              60
Lys Val Val Thr Asn Leu Thr Lys Thr Val Asn Glu Asn Lys Gln Asn
65              70              75              80
Val Asp Ala Lys Val Lys Ala Ala Glu Ser Glu Ile Glu Lys Leu Thr
                85              90              95
Thr Lys Leu Ala Asp Thr Asp Ala Ala Leu Ala Asp Thr Asp Ala Ala
            100             105             110
Leu Asp Ala Thr Thr Asn Ala Leu Asn Lys Leu Gly Glu Asn Ile Thr
            115             120             125
Thr Phe Ala Glu Glu Thr Lys Thr Asn Ile Val Lys Ile Asp Glu Lys
            130             135             140
Leu Glu Ala Val Ala Asp Thr Val Asp Lys His Ala Glu Ala Phe Asn
```

```
                145                 150                 155                 160
        Asp Ile Ala Asp Ser Leu Asp Glu Thr Asn Thr Lys Ala Asp Glu Ala
                        165                 170                 175

Val Lys Thr Ala Asn Glu Ala Lys Gln Thr Ala Glu Glu Thr Lys Gln
                        180                 185                 190

Asn Val Asp Ala Lys Val Lys Ala Glu Thr Ala Ala Gly Lys Ala
                        195                 200                 205

Glu Ala Ala Ala Gly Thr Ala Asn Thr Ala Ala Asp Lys Ala Glu Ala
                210                 215                 220

Val Ala Ala Lys Val Thr Asp Ile Lys Ala Asp Ile Ala Thr Asn Lys
        225                 230                 235                 240

Asp Asn Ile Ala Lys Lys Ala Asn Ser Ala Asp Val Tyr Thr Arg Glu
                        245                 250                 255

Glu Ser Asp Ser Lys Phe Val Arg Ile Asp Gly Leu Asn Ala Thr Thr
                        260                 265                 270

Glu Lys Leu Asp Thr Arg Leu Ala Ser Ala Glu Lys Ser Ile Ala Asp
                        275                 280                 285

His Asp Thr Arg Leu Asn Gly Leu Asp Lys Thr Val Ser Asp Leu Arg
                        290                 295                 300

Lys Glu Thr Arg Gln Gly Leu Ala Glu Gln Ala Ala Leu Ser Gly Leu
        305                 310                 315                 320

Phe Gln Pro Tyr Asn Val Gly
                        325

<210> SEQ ID NO 16
<211> LENGTH: 248
<212> TYPE: PRT
<213> ORGANISM: Neisseria meningitidis

<400> SEQUENCE: 16

Val Ala Ala Asp Ile Gly Ala Gly Leu Ala Asp Ala Leu Thr Ala Pro
        1               5                   10                  15

Leu Asp His Lys Asp Lys Gly Leu Gln Ser Leu Thr Leu Asp Gln Ser
                        20                  25                  30

Val Arg Lys Asn Glu Lys Leu Lys Leu Ala Ala Gln Gly Ala Glu Lys
                        35                  40                  45

Thr Tyr Gly Asn Gly Asp Ser Leu Asn Thr Gly Lys Leu Lys Asn Asp
                50                  55                  60

Lys Val Ser Arg Phe Asp Phe Ile Arg Gln Ile Glu Val Asp Gly Gln
        65                  70                  75                  80

Leu Ile Thr Leu Glu Ser Gly Glu Phe Gln Val Tyr Lys Gln Ser His
                        85                  90                  95

Ser Ala Leu Thr Ala Phe Gln Thr Glu Gln Ile Gln Asp Ser Glu His
                        100                 105                 110

Ser Gly Lys Met Val Ala Lys Arg Gln Phe Arg Ile Gly Asp Ile Ala
                        115                 120                 125

Gly Glu His Thr Ser Phe Asp Lys Leu Pro Glu Gly Gly Arg Ala Thr
                        130                 135                 140

Tyr Arg Gly Thr Ala Phe Gly Ser Asp Ala Gly Gly Lys Leu Thr
        145                 150                 155                 160

Tyr Thr Ile Asp Phe Ala Ala Lys Gln Gly Asn Gly Lys Ile Glu His
                        165                 170                 175

Leu Lys Ser Pro Glu Leu Asn Val Asp Leu Ala Ala Ala Asp Ile Lys
                        180                 185                 190
```

Pro Asp Gly Lys Arg His Ala Val Ile Ser Gly Ser Val Leu Tyr Asn
            195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 17
<211> LENGTH: 250
<212> TYPE: PRT
<213> ORGANISM: Neisseria meningitidis

<400> SEQUENCE: 17

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 18
<211> LENGTH: 273
<212> TYPE: PRT
<213> ORGANISM: Neisseria meningitidis

<400> SEQUENCE: 18

Met Asn Arg Thr Ala Phe Cys Cys Leu Ser Leu Thr Ala Ala Leu Ile
1               5                   10                  15

```
Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val Arg His Ile Gly Ile Ala Gly Lys
            260                 265                 270

Gln

<210> SEQ ID NO 19
<211> LENGTH: 273
<212> TYPE: PRT
<213> ORGANISM: Neisseria meningitidis

<400> SEQUENCE: 19

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110
```

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val Arg His Ile Gly Ile Ala Gly Lys
            260                 265                 270

Gln

<210> SEQ ID NO 20
<211> LENGTH: 273
<212> TYPE: PRT
<213> ORGANISM: Neisseria meningitidis

<400> SEQUENCE: 20

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Val Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Arg Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 21
<211> LENGTH: 273
<212> TYPE: PRT
<213> ORGANISM: Neisseria meningitidis

<400> SEQUENCE: 21

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Arg Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 22
<211> LENGTH: 273
<212> TYPE: PRT

<213> ORGANISM: Neisseria meningitidis

<400> SEQUENCE: 22

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Gly Asp Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 23
<211> LENGTH: 273
<212> TYPE: PRT
<213> ORGANISM: Neisseria meningitidis

<400> SEQUENCE: 23

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

```
Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Thr Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Gly Asp Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 24
<211> LENGTH: 273
<212> TYPE: PRT
<213> ORGANISM: Neisseria meningitidis

<400> SEQUENCE: 24

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ser Asp Ser Leu Ile Asn
130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175
```

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
            210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 25
<211> LENGTH: 273
<212> TYPE: PRT
<213> ORGANISM: Neisseria meningitidis

<400> SEQUENCE: 25

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Cys Arg Lys Asn Glu Lys
    50                  55                  60

Cys Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
            130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
            210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 26
<211> LENGTH: 273
<212> TYPE: PRT
<213> ORGANISM: Neisseria meningitidis

<400> SEQUENCE: 26

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Ser Val Arg Lys Asn Glu Lys
    50                  55                  60

Leu Lys Cys Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Cys Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270
```
Gln

<210> SEQ ID NO 27
<211> LENGTH: 273
<212> TYPE: PRT
<213> ORGANISM: Neisseria meningitidis

<400> SEQUENCE: 27

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
```

```
              35                  40                  45
Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Cys Leu Val Ser Gly Leu Gly Glu His Thr Ala Phe
145                 150                 155                 160

Asn Gln Leu Pro Asp Gly Lys Ala Glu Tyr His Gly Lys Ala Phe Ser
                165                 170                 175

Cys Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 28
<211> LENGTH: 273
<212> TYPE: PRT
<213> ORGANISM: Neisseria meningitidis

<400> SEQUENCE: 28

Met Asn Arg Thr Ala Phe Cys Cys Leu Ser Leu Thr Ala Ala Leu Ile
 1               5                  10                  15

Leu Thr Ala Cys Ser Ser Gly Gly Gly Val Ala Ala Asp Ile Gly
                 20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Thr Ala Leu
        115                 120                 125

Gln Ile Glu Lys Ile Asn Asn Pro Asp Lys Ile Asp Ser Leu Ile Asn
```

Gln Arg Ser Phe Leu Val Gly Asp Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val Arg His Ile Gly Ile Ala Gly Lys
            260                 265                 270

Gln

<210> SEQ ID NO 29
<211> LENGTH: 273
<212> TYPE: PRT
<213> ORGANISM: Neisseria meningitidis

<400> SEQUENCE: 29

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Arg Ile Gly Asp Ile Ala Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr

```
                225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
                260                 265                 270

Gln

<210> SEQ ID NO 30
<211> LENGTH: 273
<212> TYPE: PRT
<213> ORGANISM: Neisseria meningitidis

<400> SEQUENCE: 30

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Thr Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
                180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
        210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
                260                 265                 270

Gln

<210> SEQ ID NO 31
<211> LENGTH: 273
<212> TYPE: PRT
<213> ORGANISM: Neisseria meningitidis

<400> SEQUENCE: 31
```

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
    50                  55                  60

Leu Lys Cys Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
    210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln
```

<210> SEQ ID NO 32
<211> LENGTH: 273
<212> TYPE: PRT
<213> ORGANISM: Neisseria meningitidis

<400> SEQUENCE: 32

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95
```

```
Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Cys Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 33
<211> LENGTH: 273
<212> TYPE: PRT
<213> ORGANISM: Neisseria meningitidis

<400> SEQUENCE: 33

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Val Val Arg Lys Asn Glu Lys
50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
                100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Leu Val Thr Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190
```

```
Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
        210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
            245                 250                 255

Thr Val Lys Ile Gly Glu Lys Val His Glu Ile Gly Ile Ala Gly Lys
            260                 265                 270

Gln
```

<210> SEQ ID NO 34
<211> LENGTH: 273
<212> TYPE: PRT
<213> ORGANISM: Neisseria meningitidis

<400> SEQUENCE: 34

```
Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Val Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
    130                 135                 140

Gln Arg Ser Phe Arg Val Thr Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
        210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
            245                 250                 255

Thr Val Lys Ile Gly Glu Lys Val His Glu Ile Gly Ile Ala Gly Lys
            260                 265                 270

Gln
```

<210> SEQ ID NO 35
<211> LENGTH: 273
<212> TYPE: PRT
<213> ORGANISM: Neisseria meningitidis

<400> SEQUENCE: 35

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Val Val Arg Lys Asn Glu Lys
    50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Leu Val Gly Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 36
<211> LENGTH: 273
<212> TYPE: PRT
<213> ORGANISM: Neisseria meningitidis

<400> SEQUENCE: 36

Met Asn Arg Thr Ala Phe Cys Cys Leu Ser Leu Thr Ala Ala Leu Ile
1               5                   10                  15

Leu Thr Ala Cys Ser Ser Gly Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Val Val Arg Lys Asn Glu Lys
    50                  55                  60

-continued

```
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
130                 135                 140

Gln Arg Ser Phe Arg Val Gly Leu Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 37
<211> LENGTH: 11
<212> TYPE: PRT
<213> ORGANISM: Artificial Sequence
<220> FEATURE:
<223> OTHER INFORMATION: N-terminal sequence

<400> SEQUENCE: 37

Gly Pro Asp Ser Asp Arg Leu Gln Gln Arg Arg
1               5                   10

<210> SEQ ID NO 38
<211> LENGTH: 7
<212> TYPE: PRT
<213> ORGANISM: Artificial Sequence
<220> FEATURE:
<223> OTHER INFORMATION: N-terminal sequence

<400> SEQUENCE: 38

Gly Ser Lys Asp Ile Ser Ser
1               5

<210> SEQ ID NO 39
<211> LENGTH: 11
<212> TYPE: PRT
<213> ORGANISM: Artificial Sequence
<220> FEATURE:
<223> OTHER INFORMATION: N-terminal sequence

<400> SEQUENCE: 39

Gly Ser Lys Asp Ile Ser Ser Gly Gly Gly Gly
```

<210> SEQ ID NO 40
<211> LENGTH: 262
<212> TYPE: PRT
<213> ORGANISM: Neisseria meningitidis

<400> SEQUENCE: 40

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 41
<211> LENGTH: 250
<212> TYPE: PRT
<213> ORGANISM: Neisseria meningitidis

<400> SEQUENCE: 41

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu

```
                   50                  55                  60
Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                     85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 42
<211> LENGTH: 250
<212> TYPE: PRT
<213> ORGANISM: Neisseria meningitidis

<400> SEQUENCE: 42

Val Ala Ala Asp Ile Gly Thr Gly Leu Ala Asp Ala Leu Thr Ala Pro
 1               5                  10                  15

Leu Asp His Lys Asp Lys Gly Leu Lys Ser Leu Thr Leu Glu Asp Val
                 20                  25                  30

Ile Pro Gln Asn Gly Thr Leu Thr Leu Ser Ala Gln Gly Ala Glu Lys
             35                  40                  45

Thr Phe Lys Ala Gly Asp Lys Asp Asn Ser Leu Asn Thr Gly Lys Leu
 50                  55                  60

Lys Asn Asp Lys Ile Ser Arg Phe Asp Phe Val Gln Lys Ile Glu Val
 65                  70                  75                  80

Asp Gly Gln Thr Ile Thr Leu Ala Ser Gly Glu Phe Gln Ile Tyr Lys
                     85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Leu Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175
```

```
Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 43
<211> LENGTH: 250
<212> TYPE: PRT
<213> ORGANISM: Neisseria meningitidis

<400> SEQUENCE: 43

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 44
<211> LENGTH: 250
<212> TYPE: PRT
<213> ORGANISM: Neisseria meningitidis

<400> SEQUENCE: 44
```

Val Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
            85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
            115                 120                 125

Gly Leu Gly Gly Glu His Thr Ala Phe Asn Gln Leu Pro Gly Gly Lys
130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
            165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
            245                 250

<210> SEQ ID NO 45
<211> LENGTH: 247
<212> TYPE: PRT
<213> ORGANISM: Neisseria meningitidis

<400> SEQUENCE: 45

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
            85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 46
<211> LENGTH: 255
<212> TYPE: PRT
<213> ORGANISM: Neisseria meningitidis

<400> SEQUENCE: 46

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln

<210> SEQ ID NO 47
<211> LENGTH: 757
<212> TYPE: PRT
<213> ORGANISM: Artificial Sequence
<220> FEATURE:
<223> OTHER INFORMATION: v2-v3-v1 mutant fusion

<400> SEQUENCE: 47

```
Val Ala Ala Asp Ile Gly Ala Gly Leu Ala Asp Ala Leu Thr Ala Pro
1               5

```
            355                 360                 365
Thr Asp Ser Leu Ile Asn Gln Arg Ser Phe Arg Val Ser Gly Leu Gly
        370                 375                 380
Gly Glu His Thr Ala Phe Asn Gln Leu Pro Gly Gly Lys Ala Glu Tyr
385                 390                 395                 400
His Gly Lys Ala Phe Ser Ser Asp Asp Pro Asn Gly Arg Leu His Tyr
                405                 410                 415
Ser Ile Asp Phe Thr Lys Lys Gln Gly Tyr Gly Arg Ile Glu His Leu
            420                 425                 430
Lys Thr Leu Glu Gln Asn Val Glu Leu Ala Ala Ala Glu Leu Lys Ala
        435                 440                 445
Asp Glu Lys Ser His Ala Val Ile Leu Gly Asp Thr Arg Tyr Gly Ser
    450                 455                 460
Glu Glu Lys Gly Thr Tyr His Leu Ala Leu Phe Gly Asp Arg Ala Gln
465                 470                 475                 480
Glu Ile Ala Gly Ser Ala Thr Val Lys Ile Gly Glu Lys Val His Glu
                485                 490                 495
Ile Gly Ile Ala Gly Lys Gln Gly Ser Gly Gly Gly Val Ala Ala
            500                 505                 510
Asp Ile Gly Ala Gly Leu Ala Asp Ala Leu Thr Ala Pro Leu Asp His
        515                 520                 525
Lys Asp Lys Gly Leu Gln Ser Leu Thr Leu Asp Gln Ser Val Ser Lys
    530                 535                 540
Asn Glu Lys Leu Lys Leu Ala Ala Gln Gly Ala Glu Lys Thr Tyr Gly
545                 550                 555                 560
Asn Gly Asp Ser Leu Asn Thr Gly Lys Leu Lys Asn Asp Lys Val Ser
                565                 570                 575
Arg Phe Asp Phe Ile Arg Gln Ile Glu Val Asp Gly Gln Leu Ile Thr
            580                 585                 590
Leu Glu Ser Gly Glu Phe Gln Val Tyr Lys Gln Ser His Ser Ala Leu
        595                 600                 605
Thr Ala Phe Gln Thr Glu Gln Ile Gln Asp Ser Glu His Ser Gly Lys
    610                 615                 620
Met Val Ala Lys Arg Gln Phe Arg Ile Gly Asp Ile Ala Gly Glu His
625                 630                 635                 640
Thr Ser Phe Asp Lys Leu Pro Glu Gly Gly Arg Ala Thr Tyr Arg Gly
                645                 650                 655
Thr Ala Phe Gly Ser Asp Asp Ala Gly Gly Lys Leu Thr Tyr Thr Ile
            660                 665                 670
Asp Phe Ala Ala Lys Gln Gly Asn Gly Lys Ile Glu His Leu Lys Ser
        675                 680                 685
Pro Glu Leu Asn Val Asp Leu Ala Ala Asp Ile Lys Pro Asp Gly
    690                 695                 700
Lys Arg His Ala Val Ile Ser Gly Ser Val Leu Tyr Asn Gln Ala Glu
705                 710                 715                 720
Lys Gly Ser Tyr Ser Leu Gly Ile Phe Gly Gly Lys Ala Gln Glu Val
                725                 730                 735
Ala Gly Ser Ala Glu Val Lys Thr Val Asn Gly Ile Arg His Ile Gly
            740                 745                 750
Leu Ala Ala Lys Gln
            755

<210> SEQ ID NO 48
```

```
<211> LENGTH: 769
<212> TYPE: PRT
<213> ORGANISM: Artificial Sequence
<220> FEATURE:
<223> OTHER INFORMATION: v2-v3-v1 mutant fusion

<400> SEQUENCE: 48
```

Met Gly Pro Asp Ser Asp Arg Leu Gln Gln Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Val Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Arg Val Ser Gly Leu Gly Gly Glu His Thr
130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Val Ala Ala Asp Ile Gly Thr
            260                 265                 270

Gly Leu Ala Asp Ala Leu Thr Ala Pro Leu Asp His Lys Asp Lys Gly
        275                 280                 285

Leu Lys Ser Leu Thr Leu Glu Asp Val Ile Pro Gln Asn Gly Thr Leu
290                 295                 300

Thr Leu Ser Ala Gln Gly Ala Glu Lys Thr Phe Lys Ala Gly Asp Lys
305                 310                 315                 320

Asp Asn Ser Leu Asn Thr Gly Lys Leu Lys Asn Asp Lys Ile Ser Arg
                325                 330                 335

Phe Asp Phe Val Gln Lys Ile Glu Val Asp Gly Gln Thr Ile Thr Leu
            340                 345                 350

Ala Ser Gly Glu Phe Gln Ile Tyr Lys Gln Asn His Ser Ala Val Val
        355                 360                 365

Ala Leu Gln Ile Glu Lys Ile Asn Asn Pro Asp Lys Thr Asp Ser Leu
370                 375                 380

```
Ile Asn Gln Arg Ser Phe Arg Val Ser Gly Leu Gly Glu His Thr
385                 390                 395                 400

Ala Phe Asn Gln Leu Pro Gly Gly Lys Ala Glu Tyr His Gly Lys Ala
            405                 410                 415

Phe Ser Ser Asp Asp Pro Asn Gly Arg Leu His Tyr Ser Ile Asp Phe
            420                 425                 430

Thr Lys Lys Gln Gly Tyr Gly Arg Ile Glu His Leu Lys Thr Leu Glu
            435                 440                 445

Gln Asn Val Glu Leu Ala Ala Glu Leu Lys Ala Asp Glu Lys Ser
450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
                485                 490                 495

Ser Ala Thr Val Lys Ile Gly Glu Lys Val His Glu Ile Gly Ile Ala
            500                 505                 510

Gly Lys Gln Gly Ser Gly Gly Gly Val Ala Ala Asp Ile Gly Ala
        515                 520                 525

Gly Leu Ala Asp Ala Leu Thr Ala Pro Leu Asp His Lys Asp Lys Gly
530                 535                 540

Leu Gln Ser Leu Thr Leu Asp Gln Ser Val Ser Lys Asn Glu Lys Leu
545                 550                 555                 560

Lys Leu Ala Ala Gln Gly Ala Glu Lys Thr Tyr Gly Asn Gly Asp Ser
            565                 570                 575

Leu Asn Thr Gly Lys Leu Lys Asn Asp Lys Val Ser Arg Phe Asp Phe
            580                 585                 590

Ile Arg Gln Ile Glu Val Asp Gly Gln Leu Ile Thr Leu Glu Ser Gly
            595                 600                 605

Glu Phe Gln Val Tyr Lys Gln Ser His Ser Ala Leu Thr Ala Phe Gln
            610                 615                 620

Thr Glu Gln Ile Gln Asp Ser Glu His Ser Gly Lys Met Val Ala Lys
625                 630                 635                 640

Arg Gln Phe Arg Ile Gly Asp Ile Ala Gly Glu His Thr Ser Phe Asp
                645                 650                 655

Lys Leu Pro Glu Gly Gly Arg Ala Thr Tyr Arg Gly Thr Ala Phe Gly
            660                 665                 670

Ser Asp Asp Ala Gly Gly Lys Leu Thr Tyr Thr Ile Asp Phe Ala Ala
            675                 680                 685

Lys Gln Gly Asn Gly Lys Ile Glu His Leu Lys Ser Pro Glu Leu Asn
            690                 695                 700

Val Asp Leu Ala Ala Asp Ile Lys Pro Asp Gly Lys Arg His Ala
705                 710                 715                 720

Val Ile Ser Gly Ser Val Leu Tyr Asn Gln Ala Glu Lys Gly Ser Tyr
                725                 730                 735

Ser Leu Gly Ile Phe Gly Gly Lys Ala Gln Glu Val Ala Gly Ser Ala
            740                 745                 750

Glu Val Lys Thr Val Asn Gly Ile Arg His Ile Gly Leu Ala Ala Lys
            755                 760                 765

Gln

<210> SEQ ID NO 49
<211> LENGTH: 248
<212> TYPE: PRT
```

<213> ORGANISM: Neisseria meningitidis

<400> SEQUENCE: 49

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Ser Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 50
<211> LENGTH: 6
<212> TYPE: PRT
<213> ORGANISM: Artificial Sequence
<220> FEATURE:
<223> OTHER INFORMATION: Linker

<400> SEQUENCE: 50

Gly Ser Gly Gly Gly Gly
1               5

<210> SEQ ID NO 51
<211> LENGTH: 247
<212> TYPE: PRT
<213> ORGANISM: Neisseria meningitidis

<400> SEQUENCE: 51

Val Ala Ala Asp Ile Gly Ala Arg Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
            115                 120                 125

Gly Glu His Thr Ala Phe Asn Gln Leu Pro Asp Gly Lys Ala Glu Tyr
130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 52
<211> LENGTH: 248
<212> TYPE: PRT
<213> ORGANISM: Neisseria meningitidis

<400> SEQUENCE: 52

Val Ala Ala Asp Ile Gly Ala Gly Leu Ala Asp Ala Leu Thr Ala Pro
 1               5                  10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
         35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Lys
 65                  70                  75                  80

Leu Ile Thr Leu Glu Ser Gly Glu Phe Gln Val Tyr Lys Gln Ser His
                 85                  90                  95

Ser Ala Leu Thr Ala Leu Gln Thr Glu Gln Val Gln Asp Ser Glu Asp
                100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Lys Gly Gly Ser Ala Thr
130                 135                 140

Tyr Arg Gly Thr Ala Phe Gly Ser Asp Asp Ala Gly Gly Lys Leu Thr
145                 150                 155                 160

```
Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Glu Leu Lys
            180                 185                 190

Ala Asp Glu Lys Ser His Ala Val Ile Leu Gly Asp Thr Arg Tyr Gly
        195                 200                 205

Gly Glu Glu Lys Gly Thr Tyr His Leu Ala Leu Phe Gly Asp Arg Ala
    210                 215                 220

Gln Glu Ile Ala Gly Ser Ala Thr Val Lys Ile Arg Glu Lys Val His
225                 230                 235                 240

Glu Ile Gly Ile Ala Gly Lys Gln
                245
```

<210> SEQ ID NO 53
<211> LENGTH: 250
<212> TYPE: PRT
<213> ORGANISM: Neisseria meningitidis

<400> SEQUENCE: 53

```
Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250
```

<210> SEQ ID NO 54
<211> LENGTH: 273
<212> TYPE: PRT

<213> ORGANISM: Neisseria meningitidis

<400> SEQUENCE: 54

| Met | Asn | Arg | Thr | Ala | Ph

-continued

```
Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 56
<211> LENGTH: 247
<212> TYPE: PRT
<213> ORGANISM: Neisseria meningitidis

<400> SEQUENCE: 56

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
```

```
            195                 200                 205
Glu Glu Lys Gly Thr Tyr His Leu Ala Leu Phe Gly Asp Arg Ala Gln
    210                 215                 220
Glu Ile Ala Gly Ser Ala Thr Val Lys Ile Gly Glu Lys Val His Ala
225                 230                 235                 240
Ile Gly Ile Ala Gly Lys Gln
                245

<210> SEQ ID NO 57
<211> LENGTH: 247
<212> TYPE: PRT
<213> ORGANISM: Neisseria meningitidis

<400> SEQUENCE: 57

Val Ala Ala Asp Ile Gly Ala Gly Leu Ala Asp Ala Leu Thr Ala Pro
1               5                   10                  15
Leu Asp His Lys Asp Lys Ser Leu Gln Ser Leu Thr Leu Asp Gln Val
                20                  25                  30
Val Arg Lys Asn Glu Lys Leu Lys Leu Ala Ala Gln Gly Ala Glu Lys
            35                  40                  45
Thr Tyr Gly Asn Gly Asp Ser Leu Asn Thr Gly Lys Leu Lys Asn Asp
    50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Ile Tyr Lys Gln Asp His
                85                  90                  95
Ser Ala Val Val Ala Leu Gln Ile Glu Lys Ile Asn Asn Pro Asp Lys
            100                 105                 110
Ile Asp Ser Leu Ile Asn Gln Arg Ser Phe Arg Val Ser Gly Leu Gly
        115                 120                 125
Gly Glu His Thr Ala Phe Asn Gln Leu Pro Asp Gly Lys Ala Glu Tyr
    130                 135                 140
His Gly Lys Ala Phe Ser Ser Asp Asp Ala Gly Gly Lys Leu Thr Tyr
145                 150                 155                 160
Thr Ile Asp Phe Ala Ala Lys Gln Gly His Gly Lys Ile Glu His Leu
                165                 170                 175
Lys Thr Pro Glu Gln Asn Val Glu Leu Ala Ala Ala Glu Leu Lys Ala
            180                 185                 190
Asp Glu Lys Ser His Ala Val Ile Leu Gly Asp Thr Arg Tyr Gly Ser
        195                 200                 205
Glu Glu Lys Gly Thr Tyr His Leu Ala Leu Phe Gly Asp Arg Ala Gln
    210                 215                 220
Glu Ile Ala Gly Ser Ala Thr Val Lys Ile Gly Glu Lys Val His Ala
225                 230                 235                 240
Ile Gly Ile Ala Gly Lys Gln
                245

<210> SEQ ID NO 58
<211> LENGTH: 247
<212> TYPE: PRT
<213> ORGANISM: Neisseria meningitidis

<400> SEQUENCE: 58

Val Ala Ala Asp Ile Gly Ala Gly Leu Ala Asp Ala Leu Thr Ala Pro
1               5                   10                  15
Leu Asp His Lys Asp Lys Ser Leu Gln Ser Leu Thr Leu Asp Gln Val
```

```
            20                  25                  30
Val Arg Lys Asn Glu Lys Leu Lys Leu Ala Ala Gln Gly Ala Glu Lys
             35                  40                  45

Thr Tyr Gly Asn Gly Asp Ser Leu Asn Thr Gly Lys Leu Lys Asn Asp
 50                  55                  60

Lys Val Ser Arg Phe Asp Phe Ile Arg Gln Ile Glu Val Asp Gly Gln
 65                  70                  75                  80

Leu Ile Thr Leu Glu Ser Gly Glu Phe Gln Ile Tyr Lys Gln Asp His
                 85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Ile Gly Asp Ile Ala
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Lys Val His Glu
225                 230                 235                 240

Ile Gly Ile Ala Gly Lys Gln
                245

<210> SEQ ID NO 59
<211> LENGTH: 254
<212> TYPE: PRT
<213> ORGANISM: Neisseria meningitidis

<400> SEQUENCE: 59

Cys Ser Ser Gly Gly Gly Val Ala Ala Asp Ile Gly Ala Arg Leu
 1                   5                  10                  15

Ala Asp Ala Leu Thr Ala Pro Leu Asp His Lys Asp Lys Ser Leu Gln
             20                  25                  30

Ser Leu Thr Leu Asp Gln Ser Val Arg Lys Asn Glu Lys Leu Lys Leu
             35                  40                  45

Ala Ala Gln Gly Ala Glu Lys Thr Tyr Gly Asn Gly Asp Ser Leu Asn
 50                  55                  60

Thr Gly Lys Leu Lys Asn Asp Lys Val Ser Arg Phe Asp Phe Ile Arg
 65                  70                  75                  80

Gln Ile Glu Val Asp Gly Gln Leu Ile Thr Leu Glu Ser Gly Glu Phe
                 85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
            115                 120                 125

Phe Arg Val Ser Gly Leu Gly Gly Glu His Thr Ala Phe Asn Gln Leu
        130                 135                 140
```

```
Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 60
<211> LENGTH: 254
<212> TYPE: PRT
<213> ORGANISM: Neisseria meningitidis

<400> SEQUENCE: 60

```
Cys Ser Ser Gly Gly Gly Val Ala Ala Asp Ile Gly Ala Arg Leu
1               5                   10                  15

Ala Asp Ala Leu Thr Ala Pro Leu Asp His Lys Asp Lys Ser Leu Gln
                20                  25                  30

Ser Leu Thr Leu Asp Gln Val Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Arg Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 61

```
<211> LENGTH: 250
<212> TYPE: PRT
<213> ORGANISM: Neisseria meningitidis

<400> SEQUENCE: 61

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Arg Val Ser
            115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250
```

The invention claimed is:

1. A mutant v2 fHbp polypeptide comprising an amino acid sequence having at least 90% sequence identity to SEQ ID NO: 5 and containing an amino acid residue corresponding to residue S32 of SEQ ID NO:5 that has been substituted with any other amino acid, and further comprising a substitution at a position corresponding to L123 of SEQ ID NO:5.

2. The polypeptide of claim 1, comprising:
   (a) a sequence that differs from SEQ ID NO: 5 only by substitution at the position corresponding to S32 and at a position corresponding to L123; or
   (b) a sequence that differs from SEQ ID NO: 5 only by substitutions of S32V and L123R.

3. The polypeptide of claim 1, having a sequence comprising:
   substitutions S32V and L123R.

4. The polypeptide of claim 1, further comprising a sequence change relative to SEQ ID NO:5 where said sequence change disrupts the polypeptide's ability to bind to human factor H.

5. A polypeptide comprising a sequence selected from:
   (a) SEQ ID NO: 45,
   (b) SEQ ID NO:45 with 1, 2, 3, 4, or 5 single amino acid substitutions, deletions and/or insertions at positions other than residue V32 and R123, wherein the polypeptide can elicit antibodies which bind to a meningococcal fHbp polypeptide consisting of the amino acid sequence of SEQ ID NO: 2; and
   (c) a fHbp v2 amino acid sequence, wherein the v2 amino acid sequence is identical to a v2 wild-type amino acid sequence except for a mutation at the amino acid position corresponding to Leu-123 of SEQ ID NO: 5, provided that the mutation is not a substitution to alanine.

6. An immunogenic composition comprising a polypeptide of claim 1.

7. The composition of claim 6, further comprising a second polypeptide that, when administered to a mammal, elicits an antibody response that is bactericidal against meningococcus.

8. The composition of claim 6, further comprising a conjugated capsular saccharide selected from (i) a conjugated capsular saccharide from *N. meningitidis* serogroup A, C, W135 or Y, and (ii) a conjugated capsular saccharide from *S. pneumoniae*.

9. A method for raising an antibody response in a mammal, comprising administering an immunogenic composition of claim 6 to said mammal.

10. The polypeptide of claim 2, comprising a sequence that differs from SEQ ID NO: 5 only by substitutions of S32V and L123R.

11. The polypeptide of claim 5 where said sequence change that disrupts the polypeptide's ability to bind to human factor H is selected from a substitution at one or more of residues R73, D203, E210, G228, S121, F122, A192, E194, V199, I200, L201, T213, H215, F219, T231, and E240.

12. An immunogenic composition comprising a polypeptide of claim 5.

* * * * *